United States Patent
Hanson et al.

(10) Patent No.: US 10,202,602 B2
(45) Date of Patent: *Feb. 12, 2019

(54) OLIGONUCLEOTIDE ANALOGUES HAVING MODIFIED INTERSUBUNIT LINKAGES AND/OR TERMINAL GROUPS

(71) Applicant: Sarepta Therapeutics, Inc., Corvallis, OR (US)

(72) Inventors: Gunnar J. Hanson, Bothell, WA (US); Alexander Charles Rudolph, Snoqualmie, WA (US); Bao Zhong Cai, Corvallis, OR (US); Ming Zhou, Coppell, TX (US); Dwight D. Weller, Corvallis, OR (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/247,584

(22) Filed: Aug. 25, 2016

(65) Prior Publication Data

US 2017/0198287 A1    Jul. 13, 2017

Related U.S. Application Data

(63) Continuation of application No. 14/298,655, filed on Jun. 6, 2014, now Pat. No. 9,469,664, which is a continuation of application No. 13/118,298, filed on May 27, 2011, now Pat. No. 8,779,128.

(60) Provisional application No. 61/386,428, filed on Sep. 24, 2010, provisional application No. 61/361,878, filed on Jul. 6, 2010, provisional application No. 61/349,783, filed on May 28, 2010.

(51) Int. Cl.

| | |
|---|---|
| *C12N 15/113* | (2010.01) |
| *C07F 9/59* | (2006.01) |
| *C07F 9/572* | (2006.01) |
| *C07F 9/6558* | (2006.01) |
| *C07F 9/6561* | (2006.01) |
| *C07F 9/6584* | (2006.01) |
| *C07H 21/00* | (2006.01) |
| *A61K 31/496* | (2006.01) |
| *A61K 31/5377* | (2006.01) |
| *C07D 265/30* | (2006.01) |
| *C07D 295/108* | (2006.01) |
| *C07F 9/22* | (2006.01) |
| *C07F 9/26* | (2006.01) |
| *C07F 9/6544* | (2006.01) |

(52) U.S. Cl.
CPC .......... *C12N 15/113* (2013.01); *A61K 31/496* (2013.01); *A61K 31/5377* (2013.01); *C07D 265/30* (2013.01); *C07D 295/108* (2013.01); *C07F 9/222* (2013.01); *C07F 9/26* (2013.01); *C07F 9/572* (2013.01); *C07F 9/59* (2013.01); *C07F 9/6544* (2013.01); *C07F 9/6561* (2013.01); *C07F 9/65583* (2013.01); *C07F 9/65846* (2013.01); *C07H 21/00* (2013.01); *C12N 15/1131* (2013.01); *C12N 2310/11* (2013.01); *C12N 2310/3233* (2013.01); *C12N 2310/3513* (2013.01)

(58) Field of Classification Search
CPC .......................... C12N 15/113; C12N 15/1131
See application file for complete search history.

(56) References Cited

U.S. PATENT DOCUMENTS

| | | |
|---|---|---|
| 5,034,506 A | 7/1991 | Summerton et al. |
| 5,138,045 A | 8/1992 | Cook et al. |
| 5,142,047 A | 8/1992 | Summerton et al. |
| 5,166,315 A | 11/1992 | Summerton et al. |
| 5,185,444 A | 2/1993 | Summerton et al. |
| 5,212,295 A | 5/1993 | Cook |
| 5,217,866 A | 6/1993 | Summerton et al. |
| 5,218,105 A | 6/1993 | Cook et al. |
| 5,223,168 A | 6/1993 | Holt |
| 5,378,825 A | 1/1995 | Cook et al. |
| 5,386,023 A | 1/1995 | Sanghvi et al. |
| 5,457,191 A | 10/1995 | Cook et al. |
| 5,459,255 A | 10/1995 | Cook et al. |
| 5,506,337 A | 4/1996 | Summerton et al. |
| 5,506,351 A | 4/1996 | McGee |
| 5,521,063 A | 5/1996 | Summerton et al. |
| 5,521,302 A | 5/1996 | Cook |
| 5,539,082 A | 7/1996 | Nielsen et al. |
| 5,541,307 A | 7/1996 | Cook et al. |
| 5,554,746 A | 9/1996 | Ravikumar et al. |
| 5,571,902 A | 11/1996 | Ravikumar et al. |
| 5,576,302 A | 11/1996 | Cook et al. |
| 5,578,718 A | 11/1996 | Cook et al. |
| 5,580,767 A | 12/1996 | Cowsert et al. |
| 5,587,361 A | 12/1996 | Cook et al. |
| 5,587,469 A | 12/1996 | Cook et al. |
| 5,587,470 A | 12/1996 | Cook et al. |
| 5,599,797 A | 2/1997 | Cook et al. |
| 5,602,240 A | 2/1997 | De Mesmaeker et al. |
| 5,608,046 A | 3/1997 | Cook et al. |
| 5,610,289 A | 3/1997 | Cook et al. |
| 5,698,685 A | 12/1997 | Summerton et al. |
| 5,702,891 A | 12/1997 | Kolberg et al. |

(Continued)

FOREIGN PATENT DOCUMENTS

| | | |
|---|---|---|
| JP | H05-504563 A | 7/1993 |
| JP | 2002-167441 A | 6/2002 |

(Continued)

OTHER PUBLICATIONS

Lu et al., "Therapeutic dendritic-cell vaccine for chronic HIV-1 infection," Nature Medicine /0(12):1359-1365, Dec. 2004.

(Continued)

Primary Examiner — Joseph R Kosack
(74) Attorney, Agent, or Firm — Brian C. Trinque; Lathrop Gage LLP

(57) ABSTRACT

Oligonucleotide analogs comprising modified intersubunit linkages and/or modified 3' and/or 5'-end groups are provided. The disclosed compounds are useful for the treatment of diseases where inhibition of protein expression or correction of aberrant mRNA splice products produces beneficial therapeutic effects.

21 Claims, 14 Drawing Sheets

Specification includes a Sequence Listing.

(56) References Cited

U.S. PATENT DOCUMENTS

| | | | |
|---|---|---|---|
| 5,734,039 A | 3/1998 | Calabretta et al. | |
| 5,749,847 A | 5/1998 | Zewert et al. | |
| 5,801,154 A | 9/1998 | Baracchini et al. | |
| 5,892,023 A | 4/1999 | Pirotzky et al. | |
| 5,955,318 A | 9/1999 | Simons et al. | |
| 6,030,954 A | 2/2000 | Wu et al. | |
| 6,060,456 A | 5/2000 | Arnold, Jr. et al. | |
| 6,133,246 A | 10/2000 | McKay et al. | |
| 6,174,868 B1 | 1/2001 | Anderson et al. | |
| 6,228,579 B1 | 5/2001 | Zyskind et al. | |
| 6,239,265 B1 | 5/2001 | Cook | |
| 6,245,747 B1 | 6/2001 | Porter et al. | |
| 6,262,241 B1 | 7/2001 | Cook et al. | |
| 6,306,993 B1 | 10/2001 | Rothbard et al. | |
| 6,365,351 B1 | 4/2002 | Iversen | |
| 6,391,542 B1 | 5/2002 | Anderson et al. | |
| 6,495,663 B1 | 12/2002 | Rothbard et al. | |
| 6,548,651 B1 | 4/2003 | Nielsen et al. | |
| 6,677,153 B2 | 1/2004 | Iversen | |
| 6,784,291 B2 | 8/2004 | Iversen et al. | |
| 6,828,105 B2 | 12/2004 | Stein et al. | |
| 6,841,542 B2 | 1/2005 | Bartelmez et al. | |
| 7,049,431 B2 | 5/2006 | Iversen | |
| 7,094,765 B1 | 8/2006 | Iversen et al. | |
| 7,115,374 B2 | 10/2006 | Linnen | |
| 7,402,574 B2 | 7/2008 | Iversen et al. | |
| 7,507,196 B2 | 3/2009 | Stein et al. | |
| 7,524,829 B2 | 4/2009 | Stein et al. | |
| 7,582,615 B2 | 9/2009 | Neuman et al. | |
| 7,625,873 B2 | 12/2009 | Geller et al. | |
| 7,790,694 B2 | 9/2010 | Geller et al. | |
| 7,807,801 B2 | 10/2010 | Iversen et al. | |
| 7,838,657 B2 | 11/2010 | Singh et al. | |
| 7,943,762 B2 | 5/2011 | Weller et al. | |
| 8,030,291 B2 | 10/2011 | Stein et al. | |
| 8,030,292 B2 | 10/2011 | Stein et al. | |
| 8,067,569 B2 | 11/2011 | Iversen et al. | |
| 8,076,476 B2 | 12/2011 | Reeves et al. | |
| 8,084,433 B2 | 12/2011 | Iversen et al. | |
| 8,129,352 B2 | 3/2012 | Iversen et al. | |
| 8,168,604 B2 | 5/2012 | Stein et al. | |
| 8,198,429 B2 | 6/2012 | Iversen et al. | |
| 8,299,206 B2 | 10/2012 | Fox et al. | |
| 8,329,668 B2 | 12/2012 | Stein et al. | |
| 8,741,863 B2 | 6/2014 | Moulton et al. | |
| 8,779,128 B2 * | 7/2014 | Hanson | C07F 9/5727 544/121 |
| 8,835,402 B2 | 9/2014 | Kole et al. | |
| 8,969,551 B2 | 3/2015 | Ueda | |
| 9,068,185 B2 | 6/2015 | Iversen | |
| 9,161,948 B2 | 10/2015 | Hanson | |
| 9,238,042 B2 | 1/2016 | Schnell et al. | |
| 9,278,987 B2 | 3/2016 | Hanson et al. | |
| 9,326,992 B2 | 5/2016 | Kole et al. | |
| 9,469,664 B2 | 10/2016 | Hanson et al. | |
| 2003/0095953 A1 | 5/2003 | Cabot et al. | |
| 2003/0166588 A1 | 9/2003 | Iversen et al. | |
| 2003/0171335 A1 | 9/2003 | Stein et al. | |
| 2003/0175767 A1 | 9/2003 | Davis et al. | |
| 2003/0224353 A1 | 12/2003 | Stein et al. | |
| 2004/0110296 A1 | 6/2004 | Vargeese et al. | |
| 2004/0161844 A1 | 8/2004 | Baker et al. | |
| 2004/0259108 A1 | 12/2004 | Linnen et al. | |
| 2005/0096291 A1 | 5/2005 | Iversen et al. | |
| 2005/0107312 A1 | 5/2005 | Keicher et al. | |
| 2005/0176661 A1 | 8/2005 | Vaillant et al. | |
| 2005/0234002 A1 | 10/2005 | Mourich et al. | |
| 2006/0104989 A1 | 5/2006 | Edwards et al. | |
| 2006/0148747 A1 | 7/2006 | Stein et al. | |
| 2006/0149046 A1 | 7/2006 | Arar | |
| 2006/0269911 A1 | 11/2006 | Iversen et al. | |
| 2007/0004661 A1 | 1/2007 | Stein et al. | |
| 2007/0021362 A1 | 1/2007 | Geller et al. | |
| 2007/0037763 A1 | 2/2007 | Stein et al. | |
| 2007/0066556 A1 | 3/2007 | Stein et al. | |
| 2007/0082336 A1 | 4/2007 | Johnsson et al. | |
| 2007/0265214 A1 | 11/2007 | Stein et al. | |
| 2008/0160225 A1 | 7/2008 | Lowe et al. | |
| 2008/0194463 A1 | 8/2008 | Weller et al. | |
| 2009/0082547 A1 | 3/2009 | Iversen et al. | |
| 2009/0088562 A1 | 4/2009 | Weller et al. | |
| 2009/0099066 A1 | 4/2009 | Moulton et al. | |
| 2009/0131624 A1 | 5/2009 | Reeves et al. | |
| 2009/0131632 A1 | 5/2009 | Fox et al. | |
| 2010/0016215 A1 | 1/2010 | Moulton et al. | |
| 2010/0105120 A1 | 4/2010 | Zebala | |
| 2010/0105865 A1 | 4/2010 | Telford et al. | |
| 2010/0130591 A1 | 5/2010 | Sazani et al. | |
| 2010/0137408 A1 | 6/2010 | Geller et al. | |
| 2010/0234280 A1 | 9/2010 | Geller et al. | |
| 2010/0234281 A1 | 9/2010 | Weller et al. | |
| 2011/0118334 A1 | 5/2011 | Iversen | |
| 2011/0224283 A1 | 9/2011 | Iversen | |
| 2011/0269665 A1 | 11/2011 | Kale | |
| 2012/0065169 A1 | 3/2012 | Hanson et al. | |
| 2012/0122769 A1 | 5/2012 | Iversen | |
| 2012/0289457 A1 | 11/2012 | Hanson | |
| 2013/0288369 A1 | 10/2013 | Iversen | |
| 2013/0289091 A1 | 10/2013 | Geller et al. | |
| 2014/0024698 A1 | 1/2014 | Kole et al. | |
| 2014/0213737 A1 | 7/2014 | Weller et al. | |
| 2014/0296321 A1 | 10/2014 | Iversen | |
| 2014/0330006 A1 | 11/2014 | Hanson et al. | |
| 2015/0080311 A1 | 3/2015 | Moulton et al. | |
| 2015/0080340 A1 | 3/2015 | Hanson | |
| 2015/0141321 A1 | 5/2015 | Kole et al. | |
| 2015/0368653 A1 | 12/2015 | Iversen | |
| 2016/0237426 A1 | 8/2016 | Hanson | |
| 2016/0376587 A1 | 12/2016 | Hanson et al. | |
| 2017/0051278 A1 | 2/2017 | Kole et al. | |

FOREIGN PATENT DOCUMENTS

| | | |
|---|---|---|
| JP | 2004-537517 A | 12/2004 |
| JP | 2008-509701 A | 4/2008 |
| JP | 2008-513012 A | 5/2008 |
| JP | 2010-505741 A | 2/2010 |
| WO | 1991/009033 A1 | 6/1991 |
| WO | 1993/001286 A2 | 1/1993 |
| WO | 1997/040854 A2 | 11/1997 |
| WO | 2001/049775 A2 | 7/2001 |
| WO | 2001/076636 A2 | 10/2001 |
| WO | 2002/079467 A2 | 10/2002 |
| WO | 2002/092617 A1 | 11/2002 |
| WO | 2002/094250 A2 | 11/2002 |
| WO | 2003/033657 A2 | 4/2003 |
| WO | 2004/097017 A2 | 11/2004 |
| WO | 2005/007805 A2 | 1/2005 |
| WO | 2005/030800 A2 | 4/2005 |
| WO | 2005/065268 A2 | 7/2005 |
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/085973 A2 | 8/2006 |
| WO | 2006/086667 A2 | 8/2006 |
| WO | 2006/121951 A2 | 11/2006 |
| WO | 2007/002390 A2 | 1/2007 |
| WO | 2007/009094 A2 | 1/2007 |
| WO | 2007/030576 A2 | 3/2007 |
| WO | 2007/030691 A2 | 3/2007 |
| WO | 2007/103529 A2 | 9/2007 |
| WO | 2008/018795 A1 | 2/2008 |
| WO | 2008/036127 A2 | 3/2008 |
| WO | 2008/036406 A1 | 3/2008 |
| WO | 2009/064471 A1 | 5/2009 |
| WO | 2010/048586 A1 | 4/2010 |
| WO | 2010/120820 A1 | 10/2010 |
| WO | 2010/148249 A1 | 12/2010 |

(56) References Cited

FOREIGN PATENT DOCUMENTS

| WO | 2011/060320 A1 | 5/2011 |
|---|---|---|
| WO | 2011/150408 A2 | 12/2011 |

OTHER PUBLICATIONS

Lutkenhaus et al., "Bacterial Cell Division and the Z Ring," Annu. Rev. Biochem. 66:93-116, 1997.
Manoharan, "Oligonucleotide Conjugates as Potential Antisense Drugs with Improved Uptake, Biodistribution, Targeted Delivery, and Mechanism of Action," Antisense & Nucleic Acid Drug Development 12:103-128, 2002.
Markoff, "5'- and 3'-Noncoding Regions in Flavivirus RNA," Advances in Virus Research 59:177228, 2003.
Mellbye et al., "Variations in amino acid composition of antisense peptide-phosphorodiamidate morpholino oligomer affect potency against *Escherichia coli* in vitro and in vivo," Antimicrob Agents Chemother. 53(2):525-530, 2009.
Mertes et al., "Synthesis of Carbonate Analogs of Dinucleosides. 3'-Thymidinyl 5'-Thymidinyl Carbonate, 3'-Thymidinyl 5'-(5-Fluoro-2'-Deoxyuridinyl) Carbonate, and 3'-(5-Fluoro-2'-deoxyuridinyl) 5'-Thymidinyl Carbonate," J. Med. Chem. 12(1):154-157, 1969.
Meyer et al., "Arenaviruses: Geonomic RNAs, Transcription and Replication," Curr. Top. Microbial. Immunol. 262:139-157, 2002.
Micklefield, "Backbone Modification of Nucleic Acids: Synthesis, Structure and Therapeutic Applications," Current Medicinal Chemistry 8:1157-1179, 2001.
Mitev et al., "Inhibition of Intracellular Growth of *Salmonella enteric* Serovar Typhimurium in Tissue Culture by Antisense Peptide-Phosphorodiamidate Morpholino Oligomer," Antimicrobial Agents and Chemotherapy 53(9):3700-3704, 2009.
Miyada et al., "[6] Oligonucleotide Hybridization Techniques," Methods in Enzymology 154:94-107, 1987.
Mohamadzadeh et al., "DDendritic cells: In the forefront of immunopathogenesis and vaccine development—A review," Journal of Immune Based Therapies and Vaccines 2(1):1-11, 2004.
Morcos, "Achieving Efficient Delivery of Morpholino Oligos in Cultured Cells," Genesis 30:94-102, 2001.
Moulton et al., "Cellular Uptake of Antisense Morpholino Oligomers Conjugated to Arginine-Rich Peptides," Bioconjugate Chemistry 15:290-299, 2004.
Moulton et al., "Delivery of Antisense Phosphorodiamidate Morpholino Oligomers by Arginine-Rich Peptides", in Proceedings of the 226th ACS National Meeting, Abstract No. 75, American Chemical Society, New York, NY, Sep. 7-11, 2003, 2 pages.
Moulton et al., "HIV Tat peptide enhances cellular delivery of antisense morpholino oligomers," Antisense Nucleic Acid Drug Dev. 13(1):31-43, 2003.
Moulton et al., "Morpholinos and their peptide conjugates: Therapeutic promise and challenge for Duchenne muscular dystrophy," Biochimica et Biophysica Acta 1798:2296-2303, 2010.
Moulton et al., "Peptide-assisted delivery of steric-blocking antisense oligomers," Current Opinion in Molecular Therapeutics 5(2):123-132, 2003.
Nekhotiaeva et al., "Inhibition of *Staphylococcus aureus* Gene Expression and Growth Using Antisense Peptide Nucleic Acids," Molecular Therapy 10(4):652-659, 2004.
Nelson et al., "Arginine-Rich Peptide Conjugation to Morpholino Oligomers: Effects on Antisense Activity and Specificity," Bioconjugate Chem. 16:959-966, 2005.
Neuman et al., "Antisense Morpholino-Oligomers Directed against the 5' End of the Genome Inhibit Coronavirus Proliferation and Growth," Journal of Virology 78(11):5891-5899, 2004.
Nielsen et al., "Sequence-selective recognition of DNA by strand displacement with a thymine-substituted polyamides," Science 254(5037):1497-1500, 1991.
Nielsen, "Peptide nucleic acids as antibacterial agents via the antisense principle," Exp. Opin. Invest. Drugs 10(2):331-341, 2001.
Nielsen, "Peptide nucleic acids: on the road to new gene therapeutic drugs," Pharmacol. Toxicol. 86(1):3-7, 2000.
Nikaido, "Transport across the bacterial outer membrane," J Bioenerg Biomembr 25(6):581-589, 1993.
Orabona et al., "CD28 induces immunostimulatory signals in dendritic cells via CD80 and CD86," Nature Immunology 5(11):1134-1142, 2004.
Orr et al., "Patent review: therapeutic applications for antisense oligonucleotides 1999-2000," Curr. Opin. Mol. Thera. 2(3):325-331., 2000.
O'Ryan et al., "Rotavirus, Enteric, Adenoviruses, Norwalk Virus, and Other Gastroenteritis Tract Viruses," Chapter 22, Specter et al., (Eds.) Clinical Virology Manual, Elsevier, New York,1992, pp. 361-396.
Palu et al. "In pursuit of new developments for gene therapy of human diseases," J Biotechnol. 68(1):1-13, 1999.
Pardigon et al., "Cellular Proteins Bind to the 3' End of Sindbis Virus Minus-Strand RNA," Journal of Virology 66(2):1007-1015, 1992.
Pardigon et al., "Multiple Binding Sites for Cellular Proteins in the 3' End of Sindbis Alphavirus Minus-Sense RNA," Journal of Virology 67(8):5003-5011, 1993.
Pari et al., "Potent antiviral activity of an antisense oligonucleotide complementary to the intron-exon boundary of human cytomegalovirus genes UL36 and UL37," Antimicrob Agents Chemother. 39(5): 1157-1161, 1995.
Partridge et al., "A Simple Method for Delivering Morpholino Antisense Oligos into the Cytoplasm of Cells," Antisense & Nucleic Acid Drug Dev. 6:169-175, 1996.
Paul, Aniko V., "Possible Unifying Mechanism of Picornavirus Genome Replication," B. L. Semler et al., (Eds.), Molecular Biology of Picornaviruses, ASM Press, Wastington, DC 2002, Chap. 19, pp. 227-246.
Peters et al., "An Introduction to Ebola: The Virus and the Disease," J. Infect. Dis. / 79(Suppl 1)ix-xvi, 1999.
Petersen et al., "Synthesis of thymidine dimers containing piperazine in the internucleoside linkage and their incorporation into oligodeoxynucleotides," Tetrahedron 51:2145-2154, 1995.
Polacco et al., "A mutant of *Escherichia coli* conditionally defective in the synthesis of halo-[acyl carrier protein]," J. Biol. Chem. 256(11):5750-5754, 1981.
Polyak et al., "5' termini of Pichinde arenavirus S RNAs and mRNAs contain nontemplated nucleotides," Journal of Virology 69(5):3211-3215, 1995.
Rahman et al., "Antibacterial Activity and Inhibition of Protein Synthesis in *Escherichia coli* by Antisense DNA Analogs," Antisense Research and Development /(4):319-327, 1991.
Raviprakash et al., "Inhibition of Dengue Virus by Novel, Modified Antisense Oligonucleotides," Journal of Virology 69(1):69-74, 1995.
Roehl et al., "Poliovirus infection enhances the formation of two ribonucleoprotein complexes at the 3' end of viral legative-strand RNA," J Virol. 69(5):2954-2961, 1995.
Roehl et al., "Processing of a Cellular Polypeptide by 3CD Proteinase is Required for Poliovirus Ribonucleoprotein Complex Formation," Journal of Virology 71(1):578-585, 1997.
Rothbard et al., "Arginine-Rich Molecular Transporters for Drug Delivery: Role of Backbone Spacing in Cellular Uptake," J. Med. Chem. 45:3612-3618, 2002.
Salomon et al., Complexities of CD28/B7: CTLA-4 costimulatory pathways in autoimmunity and transplantation, Annu Rev Immunol. 19:225-252, 2001.
Sanchez et al., "Sequence analysis of the Ebola virus genome: organization, genetic elements, and comparison with the genome of Marburg virus," Virus Research 29:215-240, 1993.
Sankar et al., "Antisense oligonucleotide inhibition of encephalomyocarditis virus RNA translation," Eur. J. Biochem. 184:39-45, 1989.
Sazani et al., "Systemically delivered antisense oligomers upregulate gene expression in mouse tissues," Nature Biotechnology 20:1228-1233, Dec. 2002.
Siprashvili et al., "Gene Transfer via Reversible Plasmid Condensation with Cysteine-Flanked, Internally Spaced Arginine-Rich Peptides," Human Gene Therapy 14:1225-1233, 2003.

(56) References Cited

OTHER PUBLICATIONS

Smith et al., "Antisense treatment of Caliciviridae: An emerging disease agent of animals and humans," Current Opinion in Molecular Therapeutics 4(2):177-184, 2002.
Smith et al., "Calicivirus Emergence from Ocean Reservoirs: Zoonotic and Interspecies Movements," Emerging Infectious Diseases 4(1):13-20, 1998.
Smith et al., "Secondary structure and hybridization accessibility of the hepatitis C virus negative strand RNA 5'-terminus," Journal of Viral Hepatitis 11:115-123, 2004.
Gee et al., "Assessment of High-Affinity Hybridization, RNase H Cleavage, and Covalent Linkage in Translation Arrest by Antisense Oligonucleotides," Antisense & Nucleic Acid Drug Development 8(2):103-111, 1998.
Geisbert et al., "Ebola virus: new insights into disease aetiopathology and possible therapeutic interventions," Expert Reviews in Molecular Medicine 6(20):1-24, Sep. 21, 2004.
Geisbert et al., "Treatment of Ebola virus infection with a recombinant inhibitor of factor VIIa/tissue factor: a study in rhesus monkeys," The Lancet 362(9400):1953-1958, Dec. 13, 2003.
Geller et al., "Antisense Antibacterial Method and Compound," Office Action, dated Sep. 29, 2010, U.S. Appl. No. 11/173,847, 25 pages.
Geller et al., "Antisense phosphorodiamidate morpholino oligomer inhibits viability of *Escherichia coli* in pure culture and in mouse peritonitis," Journal of Antimicrobial Chemotherapy 55:938-988, 2005.
Geller et al., "Inhibition of Gene Expression in *Escherichia coli* by Antisense Phosphorodiamidate Morpholino Oligomers," Antimicrobial Agents and Chemotherapy 47(10):3233-3239, Oct. 2003.
Geller et al., "Translocation of Pro-OmpA across Inner Membrane Vesicles of *Escherichia coli* Occurs in Two Consecutive Energetically Distinct Steps," The Journal of Biological Chemistry 264(28):16465-16469, 1989.
GenBank Accession No. AF074613, retrieved Jul. 15, 2010, from http11www.ncbi.nlm.nih.gov/nuccore/3822114. 45 pages.
GenBank Accession No. AJ007716, retrieved Jul. 15, 2010, from http:11www.ncbi.nlm.nih.gov/nuccore/4775309. 4 pages.
GenBank Accession No. X97542.1, retrieved Jul. 15, 2010, from http:11www.ncbi.nlm.nih.gov/nuccore/2244635. 4 pages.
GenBank Accession No. Y11275.1, retrieved Jul. 15, 2010, from http:11www.ncbi.nlm.nih.gov/nuccore/4127812. 4 pages.
GenBank Accession No. AB011549, retrieved Jul. 15, 2010, from http:11www.ncbi.nlm.nih.gov/nuccore/4589740. 35 pages.
Gerdes et al., "Experimental Determination and System Level Analysis of Essential Genes in *Escherichia coli* MG1655," Journal of Bacteriology 185(19):5673-5684, Oct. 2003.
Gilbert et al., "Sieve analysis: methods for assessing from vaccine trial data how vaccine efficacy varies with genotypic and phenotypic pathogen variation," J Clinical Epidemiology 54:68-85, 2001.
Gong et al., "Molecular Mechanisms in Morpholino-DNA Surface Hybridization," J. Am. Chem. Soc.132:9663-9671, 2010.
Good et al., "Antisense PNA Effects in *Escherichia coli* are limited by the outer-membrane LPS layer," Microbiology 149(Pt 10):2665-2670, 2000.
Good et al., "Bactericidal antisense effects of peptide-PNA conjugates," Nature Biotechnology 19(4):360-364, Apr. 2001.
Good et al., "Inhibition of translation and bacterial growth by peptide nucleic acid targeted to ribosomal RNA," Proc. Natl. Acad. Sci. USA 95(5):2073-2076, 1998.
Green et al., "Antisense Oligonucleotides: An Evolving Technology for the Modulation of Gene Expression in Human Disease," J. Am. Coll. Surg. 191:93-105, 2000.
Greenberg et al., "Antisense Phosphorodiamidate Morpholino Oligmers Targeted to an Essential Gene Inhibit Burkholderia cepacia Complex," The Journal of Infectious Diseases 201(12):18221830, Jun. 2010.
Gupta, "Molecular signaling in death receptor and mitochondrial pathways of apoptosis (Review)," International Journal of Oncology 22(1):15-20, 2003.
Hale et al., "Recruitment of ZipA to the Septal Ring of *Escherichia coli* is Dependent on FtsZ and Independent of FtsA," Journal of Bacteriology 181(1):167-176, Jan. 1999.
Hames et al. (eds.), "Nucleic acid hybridization: a practical approach," IRL Press, Oxford, England, pp. 107-108, 1985, 12 pages.
Hanecak et al., "Antisense Oligonucleotide Inhibition of Hepatitis C Virus Gene Expression in Transformed Hepatocytes," Journal of Virology 70(8):5203-5212, 1996.
He et al., "A Comparison of in Vitro and in Vivo Stability in Mice of Two Morpholino Duplexes Differing in Chain Length," Bioconjugate Chem. 14:1018-1023, 2003.
Holland, Morse (ed.), Emerging Viruses, Oxford University Press US, New York, 1993, Chap. 19, "Replication Error, Quasispecies Populations, and Extreme Evolution Rates of RNA Viruses," pp. 203-218, 18 pages.
Hudziak et al., "Antiproliferative Effects of Steric Blocking Phosphorodiamidate Morpholino Antisense Agents Directed against c-myc," Antisense & Nucleic Acid Drug Dev. 10:163-176, 2000.
Hudziak et al., "Resistance of Morpholino Phosphorodiamidate Oligomers to Enzymatic Degradation," Antisense & Nucleic Acid Drug Development 6:267-272, 1996.
Hunt et al., "Identification of *Burkholderia cenocepacia* Genes Required for Bacterial Survival in Vivo," Infection and Immunity 72(7):4010-4022, 2004.
International Search Report (US), dated Aug. 17, 2006, for PCT/US05/023553, 7 pages.
Iversen et al., "Antisense Antiviral Compound and Method for Treating ssRNA Viral Infection," Office Action, dated Oct. 19, 2010, U.S. Appl. No. 11/432,031, 25 pages.
Iversen et al., "Splice-Region Antisense Composition and Method," Office Action, dated Apr. 23, 2010, U.S. Appl. No. 11/433,214, 17 pages.
Iversen, "Methods and Compositions for Manipulating Translation of Protein Isoforms From Alternative Initiation of Start Sites," U.S. Appl. No. 14/232,858, filed Jan. 14, 2014, 166 pages.
Jackowski et al., "Ratio of active to inactive forms of acyl carrier protein in *Escherichia coli*," J. Biol. Chem. 258(24)15186-15191, 1983.
Jackson et al., "*Escherichia coli* 0157:H7 diarrhoea associated with well water and infected cattle on an Ontario farm," Epidemiol Infect 120(1):17-20, 1998.
Jaeger et al., "Improved predictions of secondary structures for RNA," Proc. Natl. Sci. USA 86:7706-7710, Oct. 1989.
Jahrling et al., "Evaluation of Immune Globulin and Recombiant Interferon-a2b for Treatment of Experimental Ebola Virus Infections," The Journal of Infectious Diseases 179(Suppl 1):S222-S234, 1999.
Jen et al., "Suppression of Gene Expression by Targeted Disruption of Messenger RNA: Available Options and Current Strategies," Stem Cells 18:307-319, 2000.
Johannes et al., "Identification of eukaryotic mRNAs that are translated at reduced cap binding complex elF4F concentrations using a cDNA microarray." PNAS 96(23):13118-13123, Nov. 9, 1999.
Jubin et al., "Hepatitis C Virus Internal Ribosome Entry Site (IRES) Stem Loop IIId Contains a Phylogenetically Conserved GGG Triplet Essential for Translation and IRES Folding," Journal of Virology 74(22):10430-10437, Nov. 2000.
Kang et al., "Stacking Interactions of ApA Analogues with Modified Backbones," Biopolymers 32:1351-1363, 1992.
Knudsen et al., "Antisense properties of duplex- and triplex-forming PNAs," Nucleic Acids Res 24(3):494-500, 1996.
Kole et al., "Compound and Method for Treating Myotonic Dystrophy," U.S. Appl. No. 14/038,314, filed Sep. 26, 2013, 31 pages.
Lappalainen et al., "Cationic liposomes mediated delivery of antisense oligonucleotides targeted to HPV 16 E7 mRNA in CaSki cells," Antiviral Research 23:119-130, 1994.
Lesnikowski et al., "Octa(thymidine methanephosphonats) of partially defined stereochemistry: synthesis and effect of chirality at phosphorous on binding to pentadecadeoxyriboadenylic acid," Nucleic Acids Research 18(8):2109-2115, 1990.

(56) References Cited

OTHER PUBLICATIONS

Li et al., "Folate-Mediated Targeting of Antisense Oligodeoxynucleotides to Ovarian Cancer Cells," Pharmaceutical Research 15(10):1540-1546, 1998.

Linkletter et al., "Solid-phase synthesis of oligopurine deoxynucleic guanidine (DNG) and analysis of binding with DNA oligomers," Nucleic Acids Research 29(11):2370-2376, 2001.

Linkletter et al., "Solid-phase Synthesis of Positively Charged Deoxynucleic Guanidine (DNG) Modified Oligonucleotides Containing Neutral Urea Linkages: Effect of Charge Deletions on Binding and Fidelity," Bioorganic & Medicinal Chemistry 8:1893-1901, 2000.

Loke et al., "Characterization of Oligonucleotide transport into living cells," Proc. NaNatl.Acad. Sci USA 86(10):3474-3478, May 1989.

Lopez de Quinto et al., "Involvement of the Aphthovirus RNA Region Located between the Two Functional AUGs in Start Codon Selection," Virology 255(2):324-336, 1999.

Agrawal et al., "Antisense therapeutics: is it as simple as complementary base recognition?," Molecular Med. Today 6:72-81, 2000.

Agrawal et al., "Oligodeoxynucleoside phosphoramidates and phosphorothioates as inhibitors of human immunodeficiency virus," Proc. Natl. Acad. Sci. USA 85:7079-7083, 1988.

Agrawal et al., "Site-specific excision from RNA by RNase H and mixed-phosphate-backbone oligodeoxynucleotides," Proc. Natl. Acad. Sci. USA 87:1401-1405, 1990.

Agrawal, "Antisense oligonucleotides: towards clinical trials," Tibtech 14(10):376-387, 1996.

Akhtar et al., "Interactions of antisense DNA oligonucleotide analogs with phospholipid membranes (liposomes)," Nucleic Acids Research 19(20)5551-5559, 1991.

Anderson et al., "Distribution of Equilibrative, Nitrobenzylthioinosine-Sensitive Nucleoside Transporters (ENT1) in Brain," Journal of Neurochemistry 73(2):867-873, 1999.

Anderson et al., "IInhibition of human cytomegalovirus immediate-early gene expression by an antisense oligonucleatide complementary to immediate-early RNA," Antimicrobial Agents and Chemotherapy 40(9):2004-2011, Sep. 1996.

Arya et al., "Triple-helix formation of DNA oligomers with methyithiourea-linked nucleosides (DNmt): A kinetic and thermodynamic analysis," Proc. Natl. Acad. Sci. USA 96:4384-4389, Apr. 1999.

Bailey et al., "Cationic oligonucleotides can mediate specific inhibition of gene expression in Xenopus oocytes," Nucleic Acids Research 26(21):4860-4867, 1998.

Banerjee et al., "Interaction of picomavirus 2C polypeptide with the viral negative-strand RNA," Journal of General Virology 82:2621-2627, 2001.

Banerjee et al., "Interaction of Poliovirus-Encoded 2C/2BC Polypeptides with the 3' Terminus Negative-Strand Cloverleaf Requires an Intact Stem-Loop b," Virology 280:41-51, 2001.

Banerjee et al., "Poliovirus-Encoded 2C Polypeptide Specifically Binds to the 3'-Terminal Sequences of Viral Negative-Strand RNA," Journal of Virology 71(12):9570-9578, 1997.

Banerjee et al., "Specific Interaction of Hepatitis C Virus Protease/Helicase NS3 with the 3'Terminal Sequences of Viral Positive- and Negative-Strand RNA," Journal of Virology 75(4):1708-1721, 2001.

Barawkar et al., "Synthesis, biophysical properties, and nuclease resistance properties of mixed backbone oligodeoxynucleotides containing cationic internucleoside guanidinium linkages: Deoxynucleic guanidine/DNA chimeras," Proc. Natl. Acad. Sci. USA 95:11047-11052, Sep. 1998.

Basler et al., "The Ebola virus VP35 protein functions as a type I IFN antagonist," PNAS 97(22):12289-12294, Oct. 24, 2000.

Blommers et al., "An approach to the structure determination of nucleic acid analogues hybridized to RNA. NMR studies of a duplex between 2'-OMe RNA and an oligonucleotide containing a single amide backbone modification," Nucleic Acids Research 22(20):4187-4194, 1994.

Bonham et al., "An assessment of the antisense properties of RNase H-competent and steric-blocking oligomers," Nucleic Acids Research 23(7):1197-1203, 1995.

Borio et al., "Hemorrhagic Fever Viruses as Biological Weapons: Medical and Public Health Management," JAMA 287(18):2391-2405, May 8, 2002.

Borriello et al., "Differential Expression of Alternate Mb7-2 Transcripts," The Journal of Immunology 155(12):5490-5497, 1995.

Boudvillain et al., "Transplatin-Modified Oligo(O'-O-methyl ribonucleotide)s: A New Tool for Selective Modulation of Gene Expression," Biochemistry 36(10):2925-2931, 1997.

Bramhill, "Bacterial Cell Division," Annu Rev Cell Dev Biol 13:395-424, 1997.

Branch, "A good antisense molecule is hard to find," TIBS 23:45-50, 1998.

Brasey et al., "TThe leader of human immunodeficiency virus type 1 genomic RNA harbors an internal ribosome entry segment that is active during the G2/M phase of the cell cycle," Journal of Virology 77(7):3939-3949, Apr. 2003.

Bray et al., "A Mouse Model for Evaluation of Prophylaxis and Therapy of Ebola Hemorrhagic Fever," The Journal of Infectious Diseases 178:651-661, 1998.

Burnett et al., "The Evolving Field of Biodefence: Therapeutic Developments and Diagnostics," Natural ReviewsIDrug Discovery 4:281-297, Apr. 2005.

Chambers et al., "CTLA-4-Mediated Inhibition in Regulation of T Cell Responses: Mechanisms and Manipulation in Tumor Immunotherapy," Annu. Rev. Immunol. 19:565-594, 2001.

Chirila et al., "The use of Synthetic polymers for delivery of therapeutic antisense oligodeoxynucleotides," Biomaterials 23:321-342, 2002.

Clarke et al., "Organization and Expression of *Calicivirus* Genes," Journal of Infectious Diseases 181(Suppl 2):S309-S316, 2000.

Connolly et al., "Pathogenesis of Experimental Ebola Virus Infection in Guinea Pigs," The Journal of Infectious Diseases 179(Suppl 1):S203-S217, 1999.

Corey et al., "Morpholino antisense oligonucleotides: tools for investigating vertebrate development," Genome Biology 2(5):reviews 1015.-1015.3, Apr. 26, 2001.

Crooke, Antisense Research and Applications, ed. Springer, 1999, Chapter 1, "Basic Principles of Antisense Therapeutics," pp. 1-50.

Cross et al., "Solution Structure of an RNA•DNA Hybrid Duplex Containing a 3'-Thiaformacetal Linker and an RNA A-Tract," Biochemistry 36(14):4096-4107, 1997.

Dagle et al., "Targeted elimination of zygotic messages in Xenopus laevis embryos by modified oligonucleotides possessing terminal cationic linkages," Nucleic Acids Research 28(10):21532157, 2000.

Deas et al., "Inhibition of Flavivirus Infections by Antisense Oligomers Specifically Suppressing Viral Translation and RNA Replication," Journal of Virology 79(8):4599-4609, Apr. 2005.

Deere et al., "Antisense Phosphorodiamidate Morpholino Oligomer Length and Target Position Effects on Gene-Specific Inhibition in *Escherichia coli*," Antimicrobial Agents and Chemotherapy 49(1):249-255, Jan. 2005.

Dempcy et al., "Design and synthesis of deoxynucleic guanidine: A polycation analogue of DNA," Proc. Natl. Acad. Sci. USA 91:7864-7868, Aug. 1994.

Dempcy et al., "Design and synthesis of ribonucleic guanidine: A polycationic analog of RNA," Proc. Natl. Acad. Sci. USA 93:4326-4330, Apr. 1996.

Ding et al., "An oligodeoxyribonucleotide N3'—P5' phosphoramidate duplex forms an A-type helix in solution," Nucleic Acids Research 24(2):354-360, 1996.

Donachie, "The Cell Cycle of *Escherichia coli*," Annu. Rev. Microbiol. 47:199-230, 1993.

Dryselius et al., "The Translation Start Codon Region is Sensitive to Antisense PNA Inhibition in *Escherichia coli*," Oligonucleotides 13:427-433, 2003.

Egholm et al., "PNA hybridizes to complementary oligonucleotides obeying the Watson-Crick hydrogen-banding rules," Nature 365(6446):566-568, 1993.

(56) References Cited

OTHER PUBLICATIONS

Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications," Biochemistry 44:9045-9057, 2005.
Ex Parte Thumm, 132 USPQ 66, 1961, 3 pages.
Felgner et al., "Lipofection: A highly efficient, lipid-mediated DNA-transfection procedure," Proc. Natl. Acad. Sci. USA 84(21):7413-7417, Nov. 1987.
Feldmann et al., "Classification, Structure, and Replication of Filoviruses," Curr. Top. Microbiol. Immunol. 235:1-21, 1999.
Feldmann et al., "Ebola virus: from discovery to vaccine," Nature Reviews 3(8):677-685, Aug. 2003.
Feldmann et al., "Molecular biology and evolution of filoviruses," Arch. Virol. 7(Suppl.):81-100, 1993.
Freier, "Methods of Selecting Sites in RNA for Antisense Targeting," Crooke (ed.), Antisense Drug Technology: Principles, Strategies, and Applications, CRC Press, New York, 1999, Chap. 5, pp. 107-118, 14 pages.
Gait et al., "Synthetic Analogues of Polynucleotides. Part XII. Synthesis of Thymidine Derivatives containing an Oxyacetamido- or an Oxyformamido-linkage instead of a Phosphodiester Group," J. Chem. Soc. 0(14):1684-1686, 1974.
Galloway et al., "A mutant of *Escherichia coli* defective in the first step of endotoxin biosynthesis," J. Biol. Chem. 265(11):6394-6402, 1990.
Stein et al., "A Specificity Comparison of Four Antisense Types: Morpholino, 2'-0-Methyl RNA, DNA, and Phosphorothioate DNA," Antisense & Nucleic Acid Drug Development 7:151-157, 1997.
Stein et al., "Antisense Antiviral Agent and Method for Treating ssRNA Viral Infection," Office Action dated Feb. 17, 2010, for Corresponding U.S. Appl. No. 11/431,968, 19 pages.
Stein et al., "Inhibition of Vesivirus Infections in Mammalian Tissue Culture with Antisense Morpholino Oligomers," Antisense & Nucleic Acid Drug Development 11:317-325, 2001.
Summerton et al., "Morpholino and phosphorothioate antisense oligomers compared in cell-free and in-cell systems," Antisense Nucleic Acid Drug Dev. 7(2):63-70, 1997.
Summerton et al., "Morpholino Antisense Oligomers: Design, Preparation, and Properties," Antisense & Nucleic Acid Drug Development 7(3):187-195, 1997.
Summerton, Peptide Nucleic Acids, Morpholinos, and Related Antisense Biomolecules, Landes Bioscience/Eurekah.com and Kluwer Academic/Plenum Publishers, ed. C.G Janson and M.J. During, 2006, Chapter 6, "Morpholinos and PNAs Compared," pp. 89-113.
Summerton, "Morpholino antisense oligomers: the case for an RNase H-independent structural type," Biochim Biophys Acta. 1489(1):141-158, 1999.
Tan et al., "Peptide Nucleic Acid Antisense Oligomer as a Therapeutic Strategy against Bacterial Infection: Proof of Principle Using Mouse Intraperitoneal Infection," Antimicrobial Agents and Chemotherapy 49(8):3203-3207, Aug. 2005.
Taylor et al., "Antisense oligonucleotides: a systematic high-throughput approach to target validation and gene function determination," DDT 4(12):562-567, 1999.
Thiel et al., "Infectious RNA transcribed in vitro from a cDNA copy of the human coronavirus genome cloned in vaccinia virus," Journal of General Virology 82:1273-1281, 2001.
Tilley et al., "Antisense peptide-phosphorodiamidate morpholino oligomer conjugate: dose-response in mice infected with *Escherichia coli*," Journal of Antimicrobial Chemotherapy 59:66-73, 2007.
Tilley et al., "Gene-Specific Effects of Antisense Phosphorodiamidate Morpholino Oligomer-Peptide Conjugates on *Escherichia coli* and *Salmonella enteric* Serovar Typhimurium in Pure Culture and in Tissue Culture," Antimicrobial Agents and Chemotherapy 50(8):2789-2796, Aug. 2006.
Toulme et al., "Targeting RNA structures by antisense oligonucleotides," Biochimie 78:663-673, 1996.
Uhlmann et al., "Antisense Oligonucleotides: A New Therapeutic Principle," Chemical Reviews 90(4):544-584, Jun. 1990, 42 pages.
Van der Merwe et al., "Molecular Interactions Mediating T Cell Antigen Recognition," Annu. Rev. Immunol. 21:659-684, 2003.
Vijayakrishnan et al., "An autoimmune disease-associated CTLA-4 splice variant lacking the B7 binding domain signals negatively in T cells," Immunity. 20(5):563-575, 2004.
Wages, Jr. et al., "Affinity Purification of RNA: Sequence-Specific Capture by Nonionic Morpholino Probes," BioTechniques 23:1116-1121, 1997.
Wang et al., "Assessment of the utilization of the antisense RNA strategy to Identify essential genes in heterologous bacteria," FEMS Microbiology Letters 220(2):171-176, 2003.
Wang et al., "Specific Inhibition of Coxsackievirus B3 Translation and Replication by Phosphorothioate Antisense Oligodeoxynucleotides," Antimicrobial Agents and Chemotherapy 45(4):1043-1052, 2001.
Wang et al., "Synthesis of Antisense Phosphothioate Oligodeoxynucleotides of Dengue Fever Virus and their Anti-Viral Activity," Progress of Biochemistry and Biophysics 24(1), 12 pages, 1997.
Warfield et al., "Gene-Specific Countermeasures against Ebola Virus Based on Antisense Phosphorodiamidate Morpholino Oligomers," PLoS Pathogens 2(1):5-13, 2006.
Warfield et al., "Role of Natural Killer Cells in Innate Protection Against Lethal Ebola Virus Infection," The Journal of Experimental Medicine 200(2):169-179, 2004.
Wasem et al., "Sensitizing antigen-specific CD8+ T cells for accelerated suicide causes immune incompetence," J Clin Invest 111(8):1191-1199, 2003.
Wei et al., "Human immunodeficiency virus type-1 reverse transcription can be inhibited in vitro by oligonucleotides that target both natural and synthetic tRNA primers," Nucleic Acids Res. 28(16):3065-3074, 2000.
Weller et al., "Oligonucleotide Analogs Having Cationic Intersubunit Linkages," Advisory Action, dated Oct. 28, 2010, U.S. Appl. No. 11/801,885, 6 pages.
Weller et al., "Oligonucleotide Analogs Having Cationic Intersubunit Linkages," Office Action, dated Aug. 18, 2010, U.S. Appl. No. 11/801,885, 6 pages.
Wender et al., "The design, synthesis, and evaluation of molecules that enable or enhance cellular uptake: Peptoid molecular transporters," Proc. Natl. Acad. Sci. USA. 97(24):13003-13008, 2000.
Wiersinga, "Beyond Antibiotics: New Horizons in Treating *Burkholderia* Species Infections," The Journal of Infectious Diseases 201(12), Jun. 2010, 2 pages.
Williams et al., "Cationic lipids reduce time and dose of c-myc antisense oligodeoxynucleotides required to specifically inhibit Burkitt's lymphoma cell growth," Leukemia 10:1980-1989, 1996.
Wilson et al., "Naturally Occurring Dicistronic Cricket Paralysis Virus RNA is Regulated by Two Internal Ribosome Entry Sites," Molecular and Cellular Biology 20(14):4990-4999, Jul. 2000.
Wu et al., "Receptor-mediated in Vitro Gene Transformation by a Soluble DNA Carrier System," The Journal of Biological Chemistry 262(10):4429-4432, Apr. 5, 1987.
Wu et al., "Specific Inhibition of Hepatitis B Viral Gene Expression in Vitro by Targeted Antisense Oligonucleotides," The Journal of Biological Chemistry 267(18):12436-12439, 1992.
Xu et al., "Viral haemorrhagic disease of rabbits in the People's Republic of China: epidemiology and virus characterisation," Rev. sci. tech. Off int. Epiz. 10(2):393-408, 1991.
Yakubov et al., "Mechanism of oligonucleotide uptake by cells: Involvement of specific receptors?," Proc. Natl. Acad. Sci. USA 86(17):6454-6458, 1989.
Youngblood et al., "Stability of Cell-Penetrating Peptide—Morpholino Oligomer Conjugates in Human Serum and in Cells," Bioconjugate Chem. 18:50-60, 2007.
Zhang et al, "RNA interference in mammalian cells by siRNAs modified with morpholino nucleoside analogues," Bioorganic & Medicinal Chemistry, 17:2441-2446, 2009.
Zhang et al., "Antisense Oligonucleotide Inhibition of Hepatitis C Virus (HCV) Gene Expression in Livers of Mice Infected with an HCV-Vaccinia Virus Recombinant," Antimicrobial Agents and Chemotherapy 43(2):347-353, 1999.

(56) References Cited

OTHER PUBLICATIONS

Zhang et al., "Polar Allele Duplication for Transcriptional Analysis of Consecutive Essential Genes: Application to a Cluster of *Escherichia coli* Fatty Acid Biosynthetic Genes," Journal of Bacteriology /78(12):3614-3620, Jun. 1996.

Zollinger et al., "Meningococcal vaccines—present and future," Transactions of Royal Soc of Tropical Medicine and Hygiene 85(Supp. 1):37-43, 1991.

Zuker, "Mfold web server for nucleic acid folding and hybridization prediction," Nucleic Acids Research 31(13):3406-3415, 2003.

\* cited by examiner

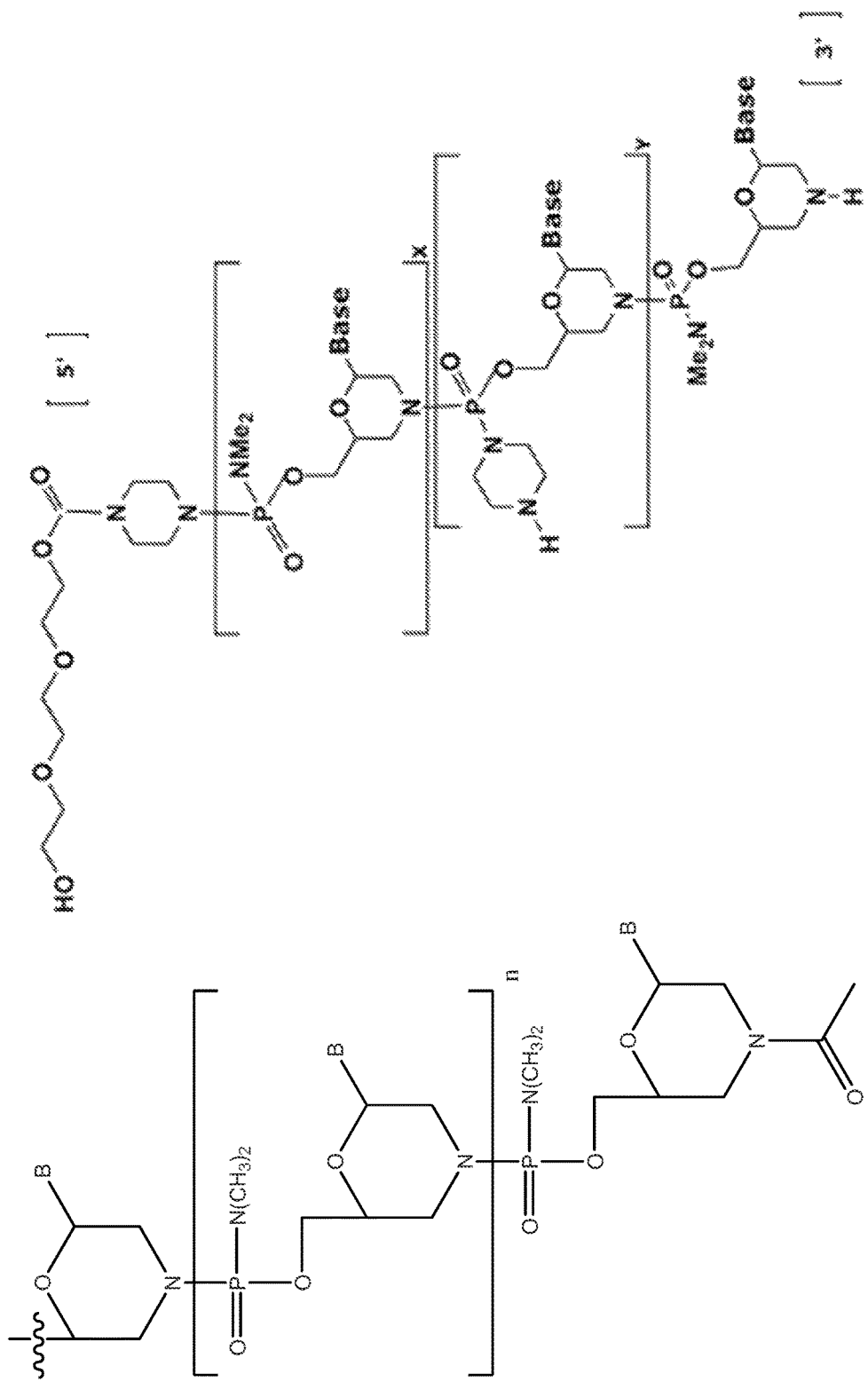

OLIGONUCLEOTIDE ANALOGUES HAVING MODIFIED INTERSUBUNIT LINKAGES AND/OR TERMINAL GROUPS

CROSS-REFERENCE TO RELATED APPLICATIONS

This application is a continuation of U.S. application Ser. No. 14/298,655 filed on Jun. 6, 2014, which is a continuation of U.S. application Ser. No. 13/118,298 filed on May 27, 2011, now issued as U.S. Pat. No. 8,779,128 which claims the benefit under 35 U.S.C. § 119(e) of U.S. Provisional Patent Application No. 61/349,783 filed on May 28, 2010; U.S. Provisional Patent Application No. 61/361,878 filed on Jul. 6, 2010 and U.S. Provisional Patent Application No. 61/386,428 filed on Sep. 24, 2010, each of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_487C1_SEQUENCE_LISTING.txt. The text file is about 18 KB, was created on Jun. 5, 2014, and is being submitted electronically.

BACKGROUND

Technical Field

The present invention is generally related to oligonucleotide compounds (oligomers) useful as antisense compounds, and more particularly to oligomer compounds comprising modified intersubunit linkages and/or terminal groups, and the use of such oligomer compounds in antisense applications.

Description of the Related Art

Antisense oligomers are generally designed to bind to DNA or RNA of disease-causing proteins to prevent the production of such proteins. Requirements for successful implementation of antisense therapeutics include (a) stability in vivo, (b) sufficient membrane permeability and cellular uptake, and (c) a good balance of binding affinity and sequence specificity. Many oligonucleotide analogues have been developed in which the phosphodiester linkages of native DNA are replaced by other linkages that are resistant to nuclease degradation (see, e.g., Barawkar, D. A. et al., *Proc. Na't'l Acad. Sci. USA* 95(19):11047-52 (1998); Linkletter, B. A. et al., *Nucleic Acids Res.* 29(11):2370-6 (2001); Micklefield, J., *Curr, Med, Chem,* 8(10):1157-79 (2001)). Antisense oligonucleotides having other various backbone modifications have also been prepared (Crooke, S. T., *Antisense Drug Technology: Principles, Strategies, and Applications*, New York, Marcel Dekker (2001); Micklefield, J., *Curr, Med, Chem,* 8(10):1157-79 (2001); Crooke, S. T., *Antisense Drug Technology*, Boca Raton, CRC Press (2008)). In addition, oligonucleotides have been modified by peptide conjugation in order to enhance cellular uptake (Moulton, H. M. et al., *Bioconjug Chem* 15(2):290-9 (2004); Nelson, M. H. et al., *Bioconjug. Chem.* 16(4):959-66 (2005); Moulton, H. M. et al., *Biochim Biophys Acta* (2010)).

The performance of such nucleic acid analogues as antisense or antigene drugs has been hampered by certain characteristics of the various analogues. For example, analogues with negatively charged linkages, including phosphorothioate-linked analogues, suffer from considerable electrostatic repulsion between the negative charges of the oligomer and the DNA or RNA target. The phosphorothioates also exhibit non-specific binding to other cellular components such as proteins. These attributes limit the therapeutic effectiveness of antisense oligomers comprised of native RNA, native DNA, and negatively charged analogues (Crooke, S. T., *Antisense Drug Technology: Principles, Strategies, and Applications*, New York, Marcel Dekker (2001); Crooke, S. T., *Antisense Drug Technology*, Boca Raton, CRC Press (2008)). The nonionic methylphosphonate-linked oligonucleotide analogues can be transported into cells by passive diffusion and/or fluid phase endocytosis, but their use is hampered by stereoisomeric complexity and poor solubility (Crooke, S. T., *Antisense Drug Technology: Principles, Strategies, and Applications*, New York, Marcel Dekker (2001); Micklefield, J., *Curr, Med, Chem,* 8(10):1157-79 (2001)).

Several groups have reported the synthesis of positively charged oligonucleotides (Bailey, C. P. et al., *Nucleic Acids Res.* 26(21):4860-7 (1998); Micklefield, J., *Curr, Med, Chem,* 8(10):1157-79 (2001); Egli, M. et al., *Biochemistry* 44(25):9045-57 (2005)). For example, a class of guanidinium linked nucleosides (designated DNG), formed by replacement of the phosphate linkages in DNA and RNA by achiral guanidino groups, has been reported (Dempcy, R. O. et al., *Proc. Nat'l Acad. Sci. USA* 91(17):7864-8 (1994); Dempcy, R. O. et al., *Proc. Nat'l Acad. Sci. USA* 93(9): 4326-30 (1996); Barawkar, D. A. et al., *Proc. Na't'l Acad. Sci. USA* 95(19):11047-52 (1998); Linkletter, B. A. et al., *Nucleic Acids Res.* 29(11):2370-6 (2001)). Oligomers linked with positively charged methylated thiourea linkages have also been reported (Arya, D. P. et al., *Proc. Nat'l Acad. Sci USA* 96(8): 4384-9 (1999)). Replacement of some of these linkages with neutral urea linkages has been reported to reduce the tendency of such positively charged oligomers towards non-sequence-specific binding (Linkletter, B. A. et al., *Bioorg. Med. Chem.* 8(8):1893-901 (2000)). Morpholino oligomers containing (1-piperazino) phosphinylideneoxy and (1-(4-(ω-guanidino-alkanoyl))-piperazino) phosphinylideneoxy linkages have been described previously (see e.g., WO2008036127).

Although significant progress has been made, there remains a need in the art for oligonucleotide analogues with improved antisense or antigene performance. Such improved antisense or antigene performance includes; stronger affinity for DNA and RNA without compromising sequence selectivity; improved pharmacokinetics and tissue distribution; improved cellular delivery and reliable and controllable in vivo distribution.

BRIEF SUMMARY

Compounds of the present invention address these issues and provide improvements over existing antisense molecules in the art. Modification of the intersubunit linkages and/or conjugation of terminal moieties to the 5' and/or 3' terminus of an oligonucleotide analogue, for example a morpholino oligonucleotide, results in an antisense oligomer having superior properties. For example, in certain embodiments the disclosed oligomers have enhanced cell delivery, potency, and/or tissue distribution compared to other oligonucleotide analogues and/or can be effectively delivered to the target organs. These superior properties give rise to favorable therapeutic indices, reduced clinical dosing, and lower cost of goods.

In one embodiment, the present disclosure provides an oligomer comprising a backbone, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid, wherein the intersubunit linkages have the following general structure (I):

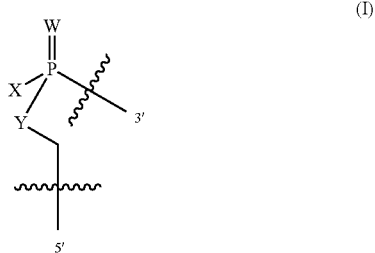

(I)

or a salt or isomer thereof, and wherein each of the intersubunit linkages (I) are independently linkage (A) or linkage (B):

wherein for linkage (A):

W is, at each occurrence, independently S or O;

X is, at each occurrence, independently —N(CH$_3$)$_2$, —NR$^1$R$^2$, —OR$^3$ or;

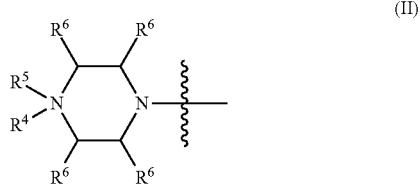

(II)

Y is, at each occurrence, independently O or —NR$^2$,

R$^1$ is, at each occurrence, independently hydrogen or methyl;

R$^2$ is, at each occurrence, independently hydrogen or -LNR$^4$R$^5$R$^7$;

R$^3$ is, at each occurrence, independently hydrogen or C$_1$-C$_6$ alkyl;

R$^4$ is, at each occurrence, independently hydrogen, methyl, —C(=NH)NH$_2$, —Z-L-NHC(=NH)NH$_2$ or —[C(O)CHR'NH]$_m$H, where Z is carbonyl (C(O)) or a direct bond, R' is a side chain of a naturally occurring amino acid or a one- or two-carbon homolog thereof, and m is 1 to 6;

R$^5$ is, at each occurrence, independently hydrogen, methyl or an electron pair;

R$^6$ is, at each occurrence, independently hydrogen or methyl;

R$^7$ is, at each occurrence, independently hydrogen C$_1$-C$_6$ alkyl or C$_1$-C$_6$ alkoxyalkyl;

L is an optional linker up to 18 atoms in length comprising alkyl, alkoxy or alkylamino groups, or combinations thereof; and wherein for linkage (B):

W is, at each occurrence, independently S or O;

X is, at each occurrence, independently —NR$^8$R$^9$ or —OR$^3$; and

Y is, at each occurrence, independently O or —NR$^{10}$,

R$^8$ is, at each occurrence, independently hydrogen or C$_2$-C$_{12}$ alkyl;

R$^9$ is, at each occurrence, independently hydrogen, C$_1$-C$_{12}$ alkyl, C$_1$-C$_{12}$ aralkyl or aryl;

R$^{10}$ is, at each occurrence, independently hydrogen, C$_1$-C$_{12}$ alkyl or -LNR$^4$R$^5$R$^7$;

wherein R$^8$ and R$^9$ may join to form a 5-18 membered mono or bicyclic heterocycle or R$^8$, R$^9$ or R$^3$ may join with R$^{10}$ to form a 5-7 membered heterocycle, and wherein when X is 4-piparazino, X has the following structure (III):

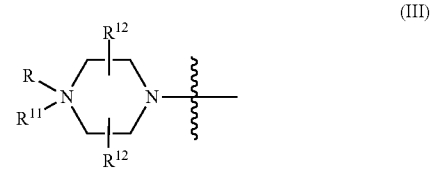

(III)

wherein:

R$^{11}$ is, at each occurrence, independently C$_2$-C$_{12}$ alkyl, C$_1$-C$_{12}$ aminoalkyl, C$_1$-C$_{12}$ alkylcarbonyl, aryl, heteroaryl or heterocyclyl; and R is, at each occurrence, independently an electron pair, hydrogen or C$_1$-C$_{12}$ alkyl; and R$^{12}$ is, at each occurrence, independently, hydrogen, C$_1$-C$_{12}$ alkyl, C$_1$-C$_{12}$ aminoalkyl, —NH$_2$, —CONH$_2$, —NR$^{13}$R$^{14}$, —NR$^{13}$R$^{14}$R$^{15}$, C$_1$-C$_{12}$ alkylcarbonyl, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —SR$^{13}$ or C$_1$-C$_{12}$ alkoxy, wherein R$^{13}$, R$^{14}$ and R$^{15}$ are, at each occurrence, independently C$_1$-C$_{12}$ alkyl; and wherein at least one of the intersubunit linkages is linkage (B).

In another embodiment the present disclosure provides an oligomer comprising modified terminal groups, for example in one embodiment the disclosure provides an oligomer comprising a backbone, the backbone comprising a sequence of morpholino ring structures joined by intersubunit linkages of type (A), (B), or combinations thereof, wherein each morpholino ring structure supports a base-pairing moiety, such that the oligomer compound can bind in a sequence-specific manner to a target nucleic acid, and wherein the oligomer comprises a 3' terminus, a 5' terminus and has the following structure (XVII):

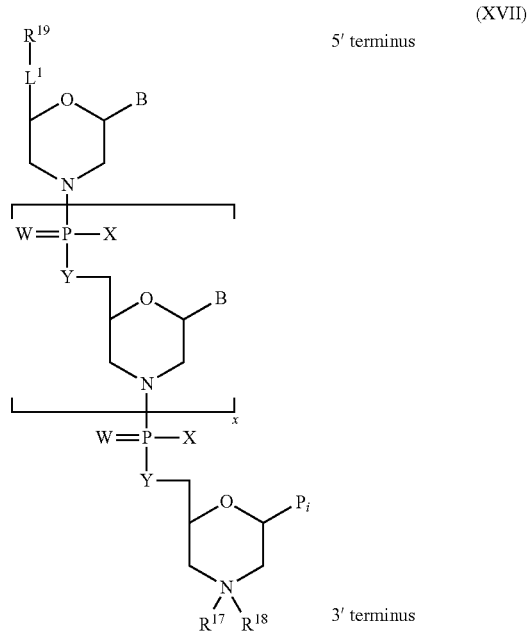

(XVII)

or a salt or isomer thereof, and wherein for linkage (A):

W is, at each occurrence, independently S or O;

X is, at each occurrence, independently —N(CH$_3$)$_2$, —NR$^1$R$^2$, —OR$^3$ or;

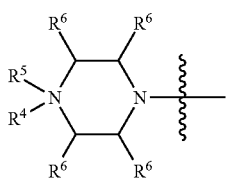

(II)

Y is, at each occurrence, independently O or —NR$^2$,

R$^1$ is, at each occurrence, independently hydrogen or methyl;

R$^2$ is, at each occurrence, independently hydrogen or -LNR$^4$R$^5$R$^7$;

R$^3$ is, at each occurrence, independently hydrogen or C$_1$-C$_6$ alkyl;

R$^4$ is, at each occurrence, independently hydrogen, methyl, —C(═NH)NH$_2$, —Z-L-NHC(═NH)NH$_2$ or —[C(O)CHR'NH]$_m$H, where Z is carbonyl (C(O)) or a direct bond, R' is a side chain of a naturally occurring amino acid or a one- or two-carbon homolog thereof, and m is 1 to 6;

R$^5$ is, at each occurrence, independently hydrogen, methyl or an electron pair;

R$^6$ is, at each occurrence, independently hydrogen or methyl;

R$^7$ is, at each occurrence, independently hydrogen C$_1$-C$_6$ alkyl or C$_1$-C$_6$ alkoxyalkyl;

L is an optional linker up to 18 atoms in length comprising alkyl, alkoxy or alkylamino groups, or combinations thereof; and wherein for linkage (B):

W is, at each occurrence, independently S or O;

X is, at each occurrence, independently —NR$^8$R$^9$ or —OR$^3$; and

Y is, at each occurrence, independently O or —NR$^{10}$,

R$^8$ is, at each occurrence, independently hydrogen or C$_2$-C$_{12}$ alkyl;

R$^9$ is, at each occurrence, independently hydrogen, C$_1$-C$_{12}$ alkyl, C$_1$-C$_{12}$ aralkyl or aryl;

R$^{10}$ is, at each occurrence, independently hydrogen, C$_1$-C$_{12}$ alkyl or -LNR$^4$R$^5$R$^7$;

wherein R$^8$ and R$^9$ may join to form a 5-18 membered mono or bicyclic heterocycle or R$^8$, R$^9$ or R$^3$ may join with R$^{10}$ to form a 5-7 membered heterocycle, and wherein when X is 4-piparazino, X has the following structure (III):

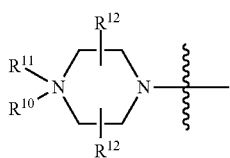

(III)

wherein:

R$^{10}$ is, at each occurrence, independently C$_2$-C$_{12}$ alkyl, C$_1$-C$_{12}$ aminoalkyl, C$_1$-C$_{12}$ alkylcarbonyl, aryl, heteroaryl or heterocyclyl; and R$^{11}$ is, at each occurrence, independently an electron pair, hydrogen or C$_1$-C$_{12}$ alkyl;

R$^{12}$ is, at each occurrence, independently, hydrogen, C$_1$-C$_{12}$ alkyl, C$_1$-C$_{12}$ aminoalkyl, —NH$_2$, —CONH$_2$, —NR$^{13}$R$^{14}$, —NR$^{13}$R$^{14}$R$^{15}$, C$_1$-C$_{12}$ alkylcarbonyl, —CN, trifluoromethyl, amidyl, amidinyl, amidinylalkyl, amidinylalkylcarbonyl, guanidinyl, guanidinylalkyl, guanidinylalkylcarbonyl, cholate, deoxycholate, aryl, heteroaryl, heterocycle, —SR$^{13}$ or C$_1$-C$_{12}$ alkoxy, wherein R$^{13}$, R$^{14}$ and R$^{15}$ are, at each occurrence, independently C$_1$-C$_{12}$ alkyl; and R$^{17}$ is, at each occurrence, independently absent, hydrogen or C$_1$-C$_6$ alkyl;

R$^{18}$ and R$^{19}$ are, at each occurrence, independently absent, hydrogen, a cell-penetrating peptide, a natural or non-natural amino acid, C$_2$-C$_{30}$ alkylcarbonyl, —C(═O)OR$^{21}$ or R$^{20}$;

R$^{20}$ is, at each occurrence, independently guanidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_3$-C$_{30}$ alkylcarbonyl, C$_3$-C$_8$ cycloalkylcarbonyl, C$_3$-C$_8$ cycloalkylalkylcarbonyl, C$_7$-C$_{30}$ arylcarbonyl, C$_7$-C$_{30}$ aralkylcarbonyl, C$_2$-C$_{30}$ alkyloxycarbonyl, C$_3$-C$_8$ cycloalkyloxycarbonyl, C$_7$-C$_{30}$ aryloxycarbonyl, C$_8$-C$_{30}$ aralkyloxycarbonyl, or —P(═O)(R$^{22}$)$_2$;

R$^{21}$ is C$_1$-C$_{30}$ alkyl comprising one or more oxygen or hydroxyl moieties or combinations thereof;

each R$^{22}$ is independently C$^6$-C$^{12}$ aryloxy;

B is a base-pairing moiety;

L$^1$ is an optional linker up to 18 atoms in length comprising bonds selected from alkyl, hydroxyl, alkoxy, alkylamino, amide, ester, disulfide, carbonyl, carbamate, phosphorodiamidate, phosphoroamidate, phosphorothioate, piperazine and phosphodiester;

x is an integer of 0 or greater; and wherein at least one of R$^{18}$ or R$^{19}$ is R$^{20}$ and provided that both of R$^{17}$ and R$^{18}$ are not absent.

In another embodiment, the present disclosure provides a method of inhibiting production of a protein, the method comprising exposing a nucleic acid encoding the protein to an oligomer of the present disclosure.

In another embodiment, the disclosure is directed to a method of treating a disease in a subject, the method comprising administering a therapeutically effective amount of an oligomer. Methods of making the oligomers and methods for their use are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

FIG. 1A shows an exemplary morpholino oligomer structure comprising a phosphorodiamidate linkage.

FIG. 1B shows a morpholino oligomer as in FIG. 1A, but where the backbone linkages comprise one piperazino phosphorodiamidate linkage.

DETAILED DESCRIPTION

I. Definitions

Figure 1C:
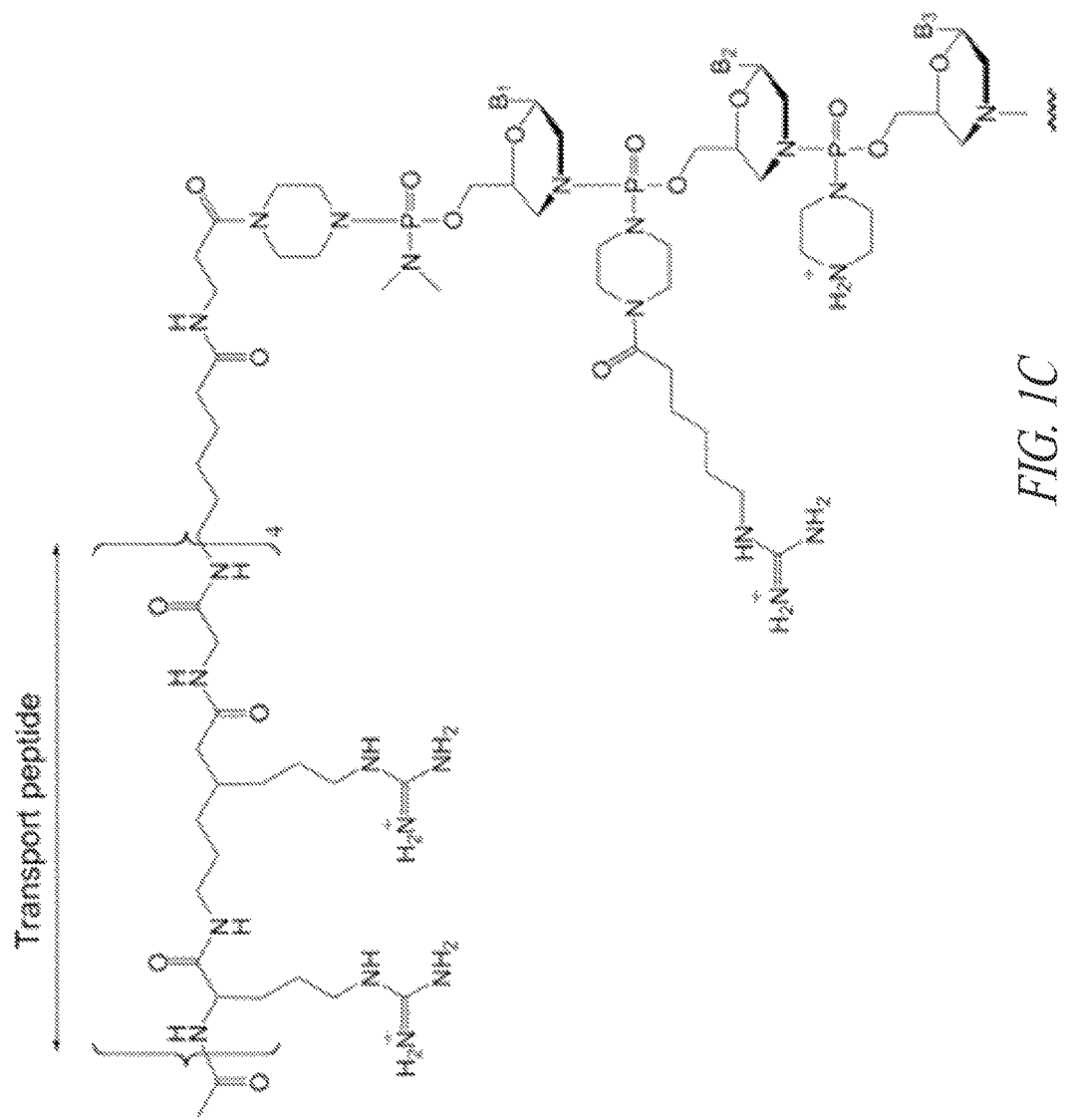
FIG. 1C shows a conjugate of an arginine-rich peptide and an antisense oligomer.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.

"Cyano" or "nitrile" refers to the —CN radical.

"Hydroxy" or "hydroxyl" refers to the —OH radical.

"Imino" refers to the =NH substituent.

"Guanidinyl" refers to the —NHC(=NH)NH$_2$ substituent.

"Amidinyl" refers to the —C(=NH)NH$_2$ substituent.

"Nitro" refers to the —NO$_2$ radical.

"Oxo" refers to the =O substituent.

"Thioxo" refers to the =S substituent.

"Cholate" refers to the following structure:

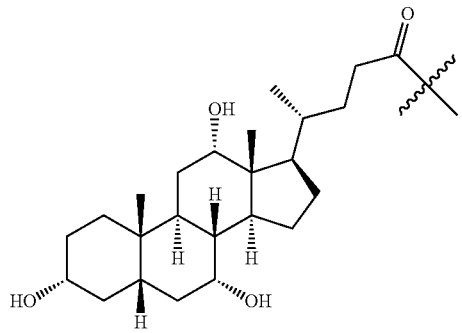

"Deoxycholate" refers to the following structure:

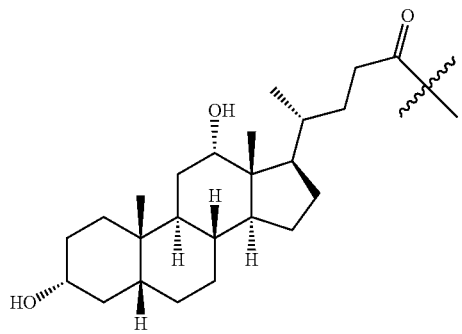

"Alkyl" refers to a straight or branched hydrocarbon chain radical which is saturated or unsaturated (i.e., contains one or more double and/or triple bonds), having from one to thirty carbon atoms, and which is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_6$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_5$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

Alkoxyalkyl" refers to a radical of the formula —R$_b$OR$_a$ where R$_a$ is an alkyl radical as defined and where R$_b$ is an alkylene radical as defined. Unless stated otherwise specifically in the specification, an alkoxyalkyl group may be optionally substituted as described below.

"Alkylcarbonyl" refers to a radical of the formula —C(=O)R$_a$ where R$_a$ is an alkyl radical as defined above. Unless stated otherwise specifically in the specification, an alkylcarbonyl group may be optionally substituted as described below.

"Alkyloxycarbonyl" refers to a radical of the formula —C(=O)OR$_a$ where R$_a$ is an alkyl radical as defined. Unless stated otherwise specifically in the specification, an alkyloxycarbonyl group may be optionally substituted as described below.

"Alkylamino" refers to a radical of the formula —NHR$_a$ or —NR$_a$R$_a$ where each R$_a$ is, independently, an alkyl radical as defined above. Unless stated otherwise specifically in the specification, an alkylamino group may be optionally substituted as described below.

"Amidyl" refers to a radical of the formula —N(H)C(=O) R$_a$ where R$_a$ is an alkyl or aryl radical as defined herein. Unless stated otherwise specifically in the specification, an amidyl group may be optionally substituted as described below.

"Amidinylalkyl" refers a radical of the formula —R$_b$—C(=NH)NH$_2$ where R$_b$ is an alkylene radical as defined above. Unless stated otherwise specifically in the specification, an amidinylalkyl group may be optionally substituted as described below.

"Amidinylalkylcarbonyl" refers a radical of the formula —C(=O)R$_b$—C(=NH)NH$_2$ where R$_b$ is an alkylene radical as defined above. Unless stated otherwise specifically in the specification, an amidinylalkylcarbonyl group may be optionally substituted as described below.

"Aminoalkyl" refers to a radical of the formula —R$_b$—NR$_a$R$_a$ where R$_b$ is an alkylene radical as defined above, and each R$_a$ is independently a hydrogen or an alkyl radical.

"Thioalkyl" refers to a radical of the formula —SR$_a$ where R$_a$ is an alkyl radical as defined above. Unless stated otherwise specifically in the specification, a thioalkyl group may be optionally substituted.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl, trityl and the like. Unless stated otherwise specifically in the specification, an aralkyl group may be optionally substituted.

"Arylcarbonyl" refers to a radical of the formula —C(=O)R$_c$ where R$_c$ is one or more aryl radicals as defined above, for example, phenyl. Unless stated otherwise specifically in the specification, an arylcarbonyl group may be optionally substituted.

"Aryloxycarbonyl" refers to a radical of the formula —C(=O)OR$_c$ where R$_c$ is one or more aryl radicals as defined above, for example, phenyl. Unless stated otherwise specifically in the specification, an aryloxycarbonyl group may be optionally substituted.

"Aralkylcarbonyl" refers to a radical of the formula —C(=O)R$_b$—R$_c$ where R$_b$ is an alkylene chain as defined above and R, is one or more aryl radicals as defined above, for example, phenyl. Unless stated otherwise specifically in the specification, an aralkylcarbonyl group may be optionally substituted.

"Aralkyloxycarbonyl" refers to a radical of the formula —C(=O)OR$_b$—R$_c$ where R$_b$ is an alkylene chain as defined above and R$_c$ is one or more aryl radicals as defined above, for example, phenyl. Unless stated otherwise specifically in the specification, an aralkyloxycarbonyl group may be optionally substituted.

"Aryloxy" refers to a radical of the formula —OR$_c$ where R$_c$ is one or more aryl radicals as defined above, for example, phenyl. Unless stated otherwise specifically in the specification, an arylcarbonyl group may be optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms and from three to eight carbon atoms, Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Cycloalkylcarbonyl" refers to a radical of the formula —C(=O)R$_d$ where R$_d$ is a cycloalkyl radical as defined above. Unless stated otherwise specifically in the specification, a cycloalkylcarbonyl group may be optionally substituted.

Cycloalkyloxycarbonyl" refers to a radical of the formula —C(=O)OR$_d$ where R$_d$ is a cycloalkyl radical as defined above. Unless stated otherwise specifically in the specification, a cycloalkyloxycarbonyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Guanidinylalkyl" refers a radical of the formula —R$_b$—NHC(=NH)NH$_2$ where R$_b$ is an alkylene radical as defined above. Unless stated otherwise specifically in the specification, a guanidinylalkyl group may be optionally substituted as described below.

"Guanidinylalkylcarbonyl" refers a radical of the formula —C(=O)R$_b$—NHC(=NH)NH$_2$ where R$_b$ is an alkylene radical as defined above. Unless stated otherwise specifically in the specification, a guanidinylalkylcarbonyl group may be optionally substituted as described below.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, —CONH$_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc. Amidyl moieties may be substituted with up to 2 halo atoms, while other groups above may be substituted with one or more halo atoms. With the exception of alkyl groups, all other groups may also be substituted with amino or monoalklyamino. With the exception of alkyl and alkylcarbonyl groups, all other groups may also be substituted with guanidinyl or amidynyl. Optional substitutents for any of the above groups also include arylphosphoryl, for example —R$_a$P(Ar)$_3$ wherein R$_a$ is an alkylene and Ar is aryl moiety, for example phenyl.

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes.

A "morpholino oligomer" or "PMO" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. An exemplary "morpholino" oligomer comprises morpholino subunit structures linked together by (thio)phosphoramidate or (thio)phosphorodiamidate linkages, joining the morpholino nitrogen of one subunit to the 5' exocyclic carbon of an adjacent subunit, each subunit comprising a purine or pyrimidine base-pairing moiety effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication number WO/2009/064471 all of which are incorporated herein by reference in their entirety. Representative PMOs include PMOs wherein the intersubunit linkages are linkage (A1).

"PMO+" refers to phosphorodiamidate morpholino oligomers comprising any number of (1-piperazino)phosphinylideneoxy, (1-(4-(ω-guanidino-alkanoyl))-piperazino) phosphinylideneoxy linkages (A2 and A3) that have been described previously (see e.g., PCT publication WO/2008/036127 which is incorporated herein by reference in its entirety.

"PMO-X" refers to phosphorodiamidate morpholino oligomers disclosed herein comprising at least one (B) linkage or at least one of the disclosed terminal modifications.

Figure 1D:
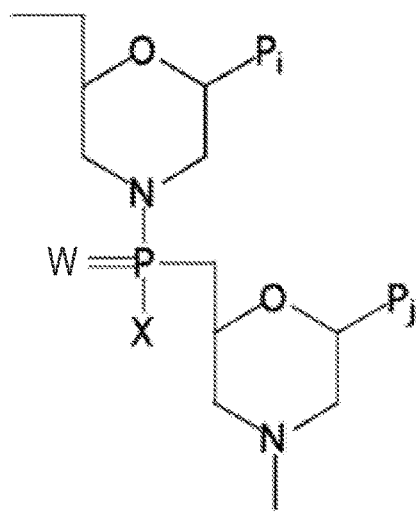
FIGS. 1D-G show the repeating subunit segment of exemplary morpholino oligonucleotides, designated 1D through 1G.
Figure 1E:
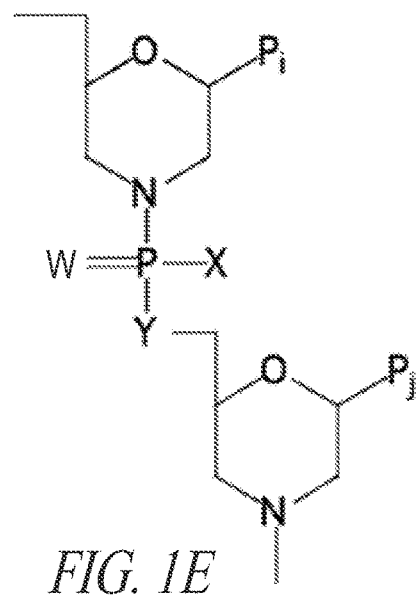
Figure 1F:
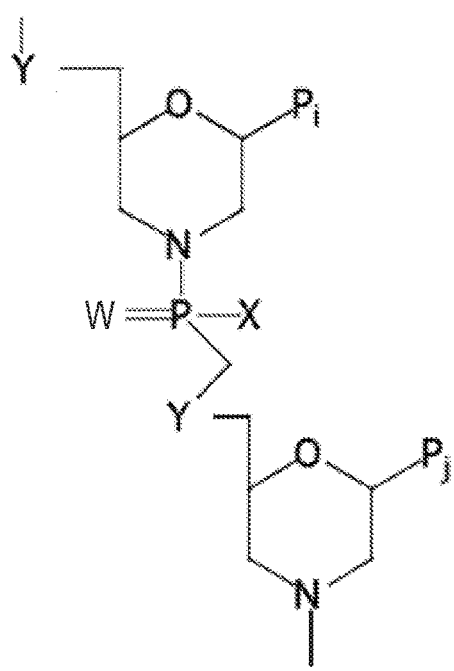
Figure 1G:
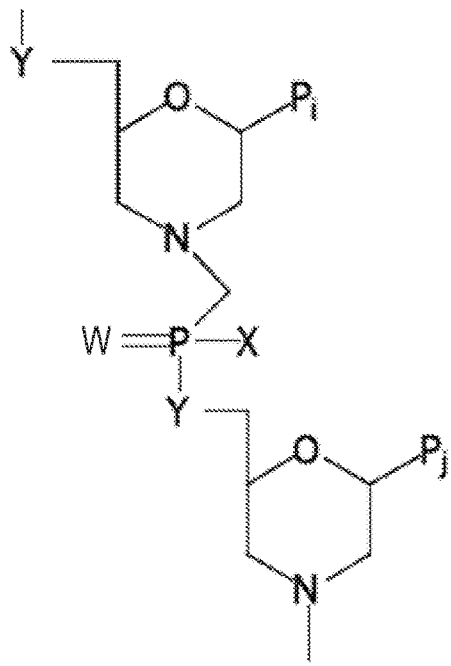

A "phosphoramidate" group comprises phosphorus having three attached oxygen atoms and one attached nitrogen atom, while a "phosphorodiamidate" group (see e.g., FIGS. 1D-E) comprises phosphorus having two attached oxygen atoms and two attached nitrogen atoms. In the uncharged or the modified intersubunit linkages of the oligomers described herein and co-pending US Patent Application No. 61/349,783 and Ser. No. 11/801,885, one nitrogen is always pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits, for example structure (I).

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In certain embodiments, a "lower alkyl" group has one to four carbon atoms. In other embodiments a "lower alkyl" group has one to two carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and/or relatively non-polar groups such as methyl, ethyl, methoxy, ethoxy, or fluoro.

An oligonucleotide or antisense oligomer "specifically hybridizes" to a target polynucleotide if the oligomer hybridizes to the target under physiological conditions, with a Tm greater than 37° C., greater than 45° C., preferably at least 50° C., and typically 60° C.-80° C. or higher. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987). Such hybridization may occur with "near" or "substantial" complementary of the antisense oligomer to the target sequence, as well as with exact complementarity.

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either a cytosine or uracil RNA base.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

The terms "modulating expression" and/or "antisense activity" refer to the ability of an antisense oligomer to either enhance or, more typically, reduce the expression of a given protein, by interfering with the expression or translation of RNA. In the case of reduced protein expression, the antisense oligomer may directly block expression of a given gene, or contribute to the accelerated breakdown of the RNA transcribed from that gene. Morpholino oligomers as described herein are believed to act via the former (steric blocking) mechanism. Preferred antisense targets for steric blocking oligomers include the ATG start codon region, splice sites, regions closely adjacent to splice sites, and 5'-untranslated region of mRNA, although other regions have been successfully targeted using morpholino oligomers.

An "amino acid subunit" is preferably an α-amino acid residue (—CO—CHR—NH—); it may also be a β- or other amino acid residue (e.g. —CO—CH$_2$CHR—NH—), where R is an amino acid side chain.

The term "naturally occurring amino acid" refers to an amino acid present in proteins found in nature. The term "non-natural amino acids" refers to those amino acids not present in proteins found in nature; examples include beta-alanine (β-Ala) and 6-aminohexanoic acid (Ahx).

An "effective amount" or "therapeutically effective amount" refers to an amount of antisense oligomer administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

II. Antisense Oligomers

A. Oligomers with Modified Intersubunit Linkages

As noted above, one embodiment of the present disclosure is directed to oligomers comprising novel intersubunit linkages. In some embodiments, the oligomers have higher affinity for DNA and RNA than do the corresponding unmodified oligomers and demonstrate improved cell delivery, potency, and/or tissue distribution properties compared to oligomers having other intersubunit linkages. In one embodiment, the oligomers comprise at least one intersubunit linkage of type (B) as defined above. The oligomers may also comprise one or more intersubunit linkages of type (A) as defined above. The structural features and properties of the various linkage types and oligomers are described in more detail in the following discussion.

1. Linkage (A)

Applicants have found that enhancement of antisense activity, biodistribution and/or other desirable properties can be optimized by preparing oligomers having various intersubunit linkages. For example, the oligomers may optionally comprise one or more intersubunit linkages of type (A), and in certain embodiments the oligomers comprise at least one linkage of type (A). In some other embodiments each linkage of type (A) has the same structure. Linkages of type (A) may include linkages disclosed in co-owned U.S. Pat. No. 7,943,762 which is hereby incorporated by reference in its entirety. Linkage (A) has the following structure (I), wherein 3' and 5' indicate the point of attachment to the 3' and 5' ends, respectively, of the morpholino ring (i.e., structure (i) discussed below):

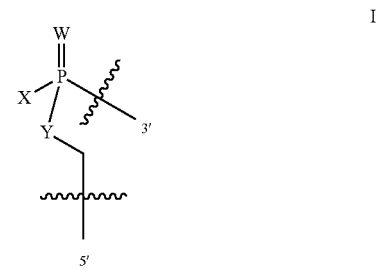

or a salt or isomer thereof, wherein:
W is, at each occurrence, independently S or O;
X is, at each occurrence, independently —N(CH$_3$)$_2$, —NR$^1$R$^2$, —OR$^3$ or;

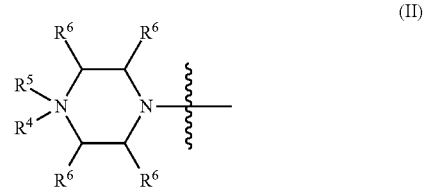

Y is, at each occurrence, independently O or —NR$^2$,
R$^1$ is, at each occurrence, independently hydrogen or methyl;

$R^2$ is, at each occurrence, independently hydrogen or -$LNR^4R^5R^7$;

$R^3$ is, at each occurrence, independently hydrogen or $C_1$-$C_6$ alkyl;

$R^4$ is, at each occurrence, independently hydrogen, methyl, —C(=NH)NH$_2$, —Z-L-NHC(=NH)NH$_2$ or —[C(=O)CHR'NH]$_m$H, where Z is —C(=O)— or a direct bond, R' is a side chain of a naturally occurring amino acid or a one- or two-carbon homolog thereof, and m is 1 to 6;

$R^5$ is, at each occurrence, independently hydrogen, methyl or an electron pair;

$R^6$ is, at each occurrence, independently hydrogen or methyl;

$R^7$ is, at each occurrence, independently hydrogen $C_1$-$C_6$ alkyl or $C_1$-$C_6$ alkoxyalkyl; and L is an optional linker up to 18 atoms in length comprising alkyl, alkoxy or alkylamino groups, or combinations thereof.

In some examples, the oligomer comprises at least one linkage of type (A). In some other embodiments, the oligomer includes at least two consecutive linkages of type (A). In further embodiments, at least 5% of the linkages in the oligomer are type (A); for example in some embodiments, 5%-95%, 10% to 90%, 10% to 50%, or 10% to 35% of the linkages may be linkage type (A). In some specific embodiments, at least one type (A) linkage is —N(CH$_3$)$_2$. In other embodiments, each linkage of type (A) is —N(CH$_3$)$_2$. In other embodiments, at least one type (A) linkage is piperizin-1-yl, for example unsubstituted piperazin-1-yl (e.g., A2 or A3). In other embodiments, each linkage of type (A) is piperizin-1-yl, for example unsubstituted piperazin-1-yl.

In some embodiments, W is, at each occurrence, independently S or O, and in certain embodiments W is O.

In some embodiments, X is, at each occurrence, independently —N(CH$_3$)$_2$, —NR$^1$R$^2$, —OR$^3$. In some embodiments X is —N(CH$_3$)$_2$. In other aspects X is —NR$^1$R$^2$, and in other examples X is —OR$^3$.

In some embodiments, $R^1$ is, at each occurrence, independently hydrogen or methyl. In some embodiments, $R^1$ is hydrogen. In other embodiments X is methyl.

In some embodiments, $R^2$ is, at each occurrence, hydrogen. In other embodiments $R^2$ is, at each occurrence, -$LNR^4R^5R^7$. In some embodiments, $R^3$ is, at each occurrence, independently hydrogen or $C_1$-$C_6$ alkyl. In other embodiments, $R^3$ is methyl. In yet other embodiments, $R^3$ is ethyl. In some other embodiments, $R^3$ is n-propyl or isopropyl. In some other embodiments, $R^3$ is $C_4$ alkyl. In other embodiments, $R^3$ is $C_5$ alkyl. In some embodiments, $R^3$ is $C_6$ alkyl.

In certain embodiments, $R^4$ is, at each occurrence, independently hydrogen. In other embodiments, $R^4$ is methyl. In yet other embodiments, $R^4$ is —C(=NH)NH$_2$, and in other embodiments, $R^4$ is —Z-L-NHC(=NH)NH$_2$. In still other embodiments, $R^4$ is —[C(=O)CHR'NH]$_m$H. Z is —C(=O)— in one embodiment and Z is a direct bond in another embodiment. R' is a side chain of a naturally occurring amino acid. In some embodiments R' is a one- or two-carbon homolog of a side chain of a naturally occurring amino acid.

m is and integer from 1 to 6. m may be 1. m may be 2 m may be 3 m may be 4 m may be 5 may be 6

In some embodiments, $R^5$ is, at each occurrence, independently hydrogen, methyl or an electron pair. In some embodiments, $R^5$ is hydrogen. In other embodiments, $R^5$ is methyl. In yet other embodiments, $R^5$ is an electron pair.

In some embodiments, $R^6$ is, at each occurrence, independently hydrogen or methyl. In some embodiments, $R^6$ is hydrogen. In other embodiments, $R^6$ is methyl.

In other embodiments, $R^7$ is, at each occurrence, independently hydrogen $C_1$-$C_6$ alkyl or $C_2$-$C_6$ alkoxyalkyl. In some embodiments $R^7$ is hydrogen. In other embodiments, $R^7$ is $C_1$-$C_6$ alkyl. In yet other embodiments, $R^7$ is $C_2$-$C_6$ alkoxyalkyl. In some embodiments, $R^7$ is methyl. In other embodiments, $R^7$ is ethyl. In yet other embodiments, $R^7$ is n-propyl or isopropyl. In some other embodiments, $R^7$ is $C_4$ alkyl. In some embodiments, $R^7$ is $C_5$ alkyl. In some embodiments, $R^7$ is $C_6$ alkyl. In yet other embodiments, $R^7$ is $C_2$ alkoxyalkyl. In some other embodiments, $R^7$ is $C_3$ alkoxyalkyl. In yet other embodiments, $R^7$ is $C_4$ alkoxyalkyl. In some embodiments, $R^7$ is $C_5$ alkoxyalkyl. In other embodiments, $R^7$ is $C_6$ alkoxyalkyl.

The linker group L, as noted above, contains bonds in its backbone selected from alkyl (e.g. —CH2-CH2-), alkoxy (e.g., —C—O—C—), and alkylamino (e.g. —CH2-NH—), with the proviso that the terminal atoms in L (e.g., those adjacent to carbonyl or nitrogen) are carbon atoms. Although branched linkages (e.g. —CH2-CHCH3-) are possible, the linker is generally unbranched. In one embodiment, the linker is a hydrocarbon linker. Such a linker may have the structure (CH2)$_n$—, where n is 1-12, preferably 2-8, and more preferably 2-6.

Oligomers having any number of linkage type (A) are provided. In some embodiments, the oligomer contains no linkages of type (A). In certain embodiments, 5, 10, 20, 30, 40, 50, 60, 70, 80 or 90 percent of the linkages are linkage (A). In selected embodiments, 10 to 80, 20 to 80, 20 to 60, 20 to 50, 20 to 40, or 20 to 35 percent of the linkages are linkage (A).

2. Linkage (B)

In some embodiments, the oligomers comprise at least one linkage of type (B). For example the oligomers may comprise 1, 2, 3, 4, 5, 6 or more linkages of type (B). The type (B) linkages may be adjacent or may be interspersed throughout the oligomer. Linkage type (B) has the following structure (I):

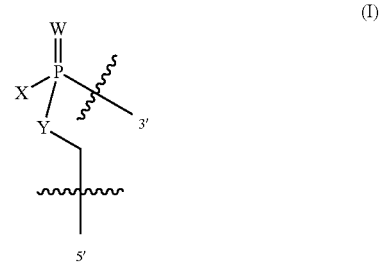

(I)

or a salt or isomer thereof, wherein:

W is, at each occurrence, independently S or O;

X is, at each occurrence, independently —NR$^8$R$^9$ or —OR$^3$; and

Y is, at each occurrence, independently O or —NR$^{10}$, $R^3$ is, at each occurrence, independently hydrogen or $C_1$-$C_6$ alkyl;

$R^8$ is, at each occurrence, independently hydrogen or $C_2$-$C_{12}$ alkyl;

$R^9$ is, at each occurrence, independently hydrogen, $C_1$-$C_{12}$ alkyl, $C_1$-$C_{12}$ aralkyl or aryl;

$R^{10}$ is, at each occurrence, independently hydrogen, $C_1$-$C_{12}$ alkyl or -$LNR^4R^5R^7$;

wherein $R^8$ and $R^9$ may join to form a 5-18 membered mono or bicyclic heterocycle or $R^8$, $R^9$ or $R^3$ may join with $R^{10}$ to form a 5-7 membered heterocycle, and wherein when X is 4-piparazino, X has the following structure (III):

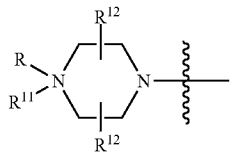

(III)

wherein:

$R^{11}$ is, at each occurrence, independently $C_2$-$C_{12}$ alkyl, $C_1$-$C_{12}$ aminoalkyl, $C_1$-$C_{12}$ alkylcarbonyl, aryl, heteroaryl or heterocyclyl;

R is, at each occurrence, independently an electron pair, hydrogen or $C_1$-$C_{12}$ alkyl; and $R^{12}$ is, at each occurrence, independently, hydrogen, $C_1$-$C_{12}$ alkyl, $C_1$-$C_{12}$ aminoalkyl, —$NH_2$, —$CONH_2$, —$NR^{13}R^{14}$, —$NR^{13}R^{14}R^{15}$, $C_1$-$C_{12}$ alkylcarbonyl, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —$SR^{13}$ or $C_1$-$C_{12}$ alkoxy, wherein $R^{13}$, $R^{14}$ and $R^{15}$ are, at each occurrence, independently $C_1$-$C_{12}$ alkyl.

In some examples, the oligomer comprises one linkage of type (B). In some other embodiments, the oligomer comprises two linkages of type (B). In some other embodiments, the oligomer comprises three linkages of type (B). In some other embodiments, the oligomer comprises four linkages of type (B). In still other embodiments, the linkages of type (B) are consecutive (i.e., the type (B) linkages are adjacent to each other). In further embodiments, at least 5% of the linkages in the oligomer are type (B); for example in some embodiments, 5%-95%, 10% to 90%, 10% to 50%, or 10% to 35% of the linkages may be linkage type (B).

In other embodiments, $R^3$ is, at each occurrence, independently hydrogen or $C_1$-$C_6$ alkyl. In yet other embodiments, $R^3$ may be methyl. In some embodiments, $R^3$ may be ethyl. In some other embodiments, $R^3$ may be n-propyl or isopropyl. In yet other embodiments, $R^3$ may be $C_4$ alkyl. In some embodiments, $R^3$ may be $C_5$ alkyl. In some embodiments, $R^3$ may be $C_6$ alkyl.

In some embodiments, $R^8$ is, at each occurrence, independently hydrogen or $C_2$-$C_{12}$ alkyl. In some embodiments, $R^8$ is hydrogen. In yet other embodiments, $R^8$ is ethyl. In some other embodiments, $R^8$ is n-propyl or isopropyl. In some embodiments, $R^8$ is $C_4$ alkyl. In yet other embodiments, $R^8$ is $C_5$ alkyl. In other embodiments, $R^8$ is $C_6$ alkyl. In some embodiments, $R^8$ is $C_7$ alkyl. In yet other embodiments, $R^8$ is $C_8$ alkyl. In other embodiments, $R^8$ is $C_9$ alkyl. In yet other embodiments, $R^8$ is $C_{10}$ alkyl. In some other embodiments, $R^8$ is $C_{11}$ alkyl. In yet other embodiments, $R^8$ is $C_{12}$ alkyl. In some embodiments, $R^8$ is $C_2$-$C_{12}$ alkyl and the $C_2$-$C_{12}$ alkyl includes one or more double bonds (e.g., alkene), triple bonds (e.g., alkyne) or both. In some embodiments, $R^8$ is unsubstituted $C_2$-$C_{12}$ alkyl.

In some embodiments, $R^9$ is, at each occurrence, independently hydrogen, $C_1$-$C_{12}$ alkyl, $C_1$-$C_{12}$ aralkyl or aryl. In some embodiments, $R^9$ is hydrogen. In yet other embodiments, $R^9$ is $C_1$-$C_{12}$ alkyl. In other embodiments, $R^9$ is methyl. In yet other embodiments, $R^9$ is ethyl. In some other embodiments, $R^9$ is n-propyl or isopropyl. In some embodiments, $R^9$ is $C_4$ alkyl. In some embodiments, $R^9$ is $C_5$ alkyl. In yet other embodiments, $R^9$ is $C_6$ alkyl. In some other embodiments, $R^9$ is $C_7$ alkyl. In some embodiments, $R^9$ is $C_8$ alkyl. In some embodiments, $R^9$ is $C_9$ alkyl. In some other embodiments, $R^9$ is $C_{10}$ alkyl. In some other embodiments, $R^9$ is $C_{11}$ alkyl. In yet other embodiments, $R^9$ is $C_{12}$ alkyl.

In some other embodiments, $R^9$ is $C_1$-$C_{12}$ aralkyl. For example, n some embodiments $R^9$ is benzyl and the benzyl may be optionally substituted on either the phenyl ring or the benzylic carbon. Substituents in this regards include alkyl and alkoxy groups, for example methyl or methoxy. In some embodiments, the benzyl group is substituted with methyl at the benzylic carbon. For example, in some embodiments, $R^9$ has the following structure (XIV):

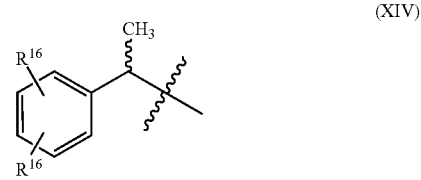

(XIV)

In other embodiments, $R^9$ is aryl. For example, in some embodiments $R^9$ is phenyl, and the phenyl may be optionally substituted. Substituents in this regard substitutents include alkyl and alkoxy groups, for example methyl or methoxy. In other embodiments, $R^9$ is phenyl and the phenyl comprises a crown ether moiety, for example a 12-18 membered crown ether. In one embodiment the crown ether is 18 membered and may further comprise and additional phenyl moiety. For example, in one embodiment $R^9$ has one of the following structures (XV) or XVI):

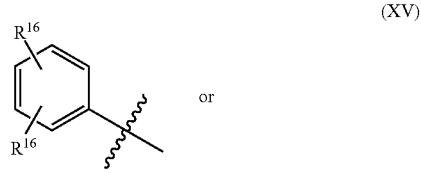

(XV)

or

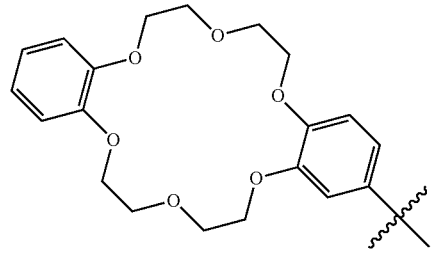

(XVI)

In some embodiments, $R^{10}$ is, at each occurrence, independently hydrogen, $C_1$-$C_{12}$ alkyl or -$LNR^4R^5R^7$, wherein $R^4$, $R^5$ and $R^7$ are as defined above with respect to linkage (A). In other embodiments, $R^{10}$ is hydrogen. In other embodiments, $R^{10}$ is $C_1$-$C_{12}$ alkyl, and in other embodiments $R^{10}$ is -$LNR^4R^5R^7$. In some embodiments, $R^{10}$ is methyl. In yet other embodiments, $R^{10}$ is ethyl. In some embodiments, $R^{10}$ is $C_3$ alkyl. In some embodiments, $R^{10}$ is $C_4$ alkyl. In yet other embodiments, $R^{10}$ is $C_5$ alkyl. In some other embodiments, $R^{10}$ is $C_6$ alkyl. In other embodiments, $R^{10}$ is $C_7$ alkyl. In yet other embodiments, $R^{10}$ is $C_8$ alkyl. In some embodiments, $R^{10}$ is $C_9$ alkyl. In other embodiments, $R^{10}$ is $C_{10}$ alkyl. In yet other embodiments, $R^{10}$ is $C_{11}$ alkyl. In some other embodiments, $R^{10}$ is $C_{12}$ alkyl.

In some embodiments, $R^8$ and $R^9$ join to form a 5-18 membered mono or bicyclic heterocycle. In some embodiments the heterocycle is a 5 or 6 membered monocyclic heterocycle. For example, in some embodiments linkage (B) has the following structure (IV):

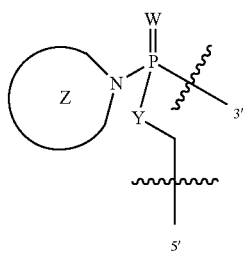

(IV)

In other embodiments, heterocycle is bicyclic, for example a 12-membered bicyclic heterocycle. The heterocycle may be piperizinyl. The heterocycle may be morpholino. The heterocycle may be piperidinyl. The heterocycle may be decahydroisoquinoline. Representative heterocycles include the following:

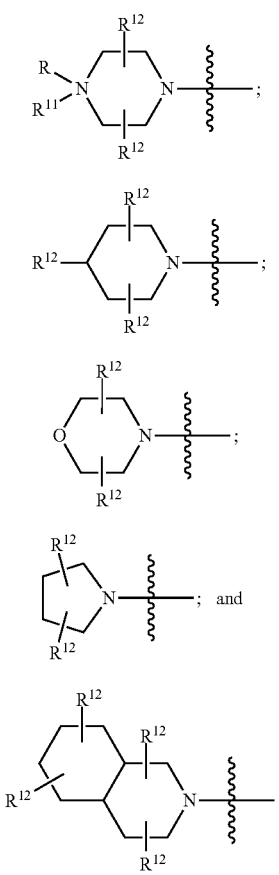

(III)

(V)

(VI)

(VII)

(VIII)

In some embodiments, $R^{11}$ is, at each occurrence, independently $C_2$-$C_{12}$ alkyl, $C_1$-$C_{12}$ aminoalkyl, aryl, heteroaryl or heterocyclyl.

In some embodiments, $R^{11}$ is $C_2$-$C_{12}$ alkyl. In some embodiments, $R^{11}$ is ethyl. In other embodiments, $R^{11}$ is $C_3$ alkyl. In yet other embodiments, $R^{11}$ is isopropyl. In some other embodiments, $R^{11}$ is $C_4$ alkyl. In other embodiments, $R^{11}$ is $C_5$ alkyl. In some embodiments, $R^{11}$ is $C_6$ alkyl. In other embodiments, $R^{11}$ is $C_7$ alkyl. In some embodiments, $R^{11}$ is $C_8$ alkyl. In other embodiments, $R^{11}$ is $C_9$ alkyl. In yet other embodiments, $R^{11}$ is $C_{10}$ alkyl. In some other embodiments, $R^{11}$ is $C_{11}$ alkyl. In some embodiments, $R^{11}$ is $C_{12}$ alkyl.

In other embodiments, $R^{11}$ is $C_1$-$C_{12}$ aminoalkyl. In some embodiments, $R^{11}$ is methylamino. In some embodiments, $R^{11}$ is ethylamino. In other embodiments, $R^{11}$ is $C_3$ aminoalkyl. In yet other embodiments, $R^{11}$ is $C_4$ aminoalkyl. In some other embodiments, $R^{11}$ is $C_5$ aminoalkyl. In other embodiments, $R^{11}$ is $C_6$ aminoalkyl. In yet other embodiments, $R^{11}$ is $C_7$ aminoalkyl. In some embodiments, $R^{11}$ is $C_8$ aminoalkyl. In other embodiments, $R^{11}$ is $C_9$ aminoalkyl. In yet other embodiments, $R^{11}$ is $C_{10}$ aminoalkyl. In some other embodiments, $R^{11}$ is $C_{11}$ aminoalkyl. In other embodiments, $R^{11}$ is $C_{12}$ aminoalkyl.

In other embodiments, $R^{11}$ is $C_1$-$C_{12}$ alkylcarbonyl. In yet other embodiments, $R^1$ is $C_1$ alkylcarbonyl. In other embodiments, $R^{11}$ is $C_2$ alkylcarbonyl. In some embodiments, $R^{11}$ is $C_3$ alkylcarbonyl. In yet other embodiments, $R^{11}$ is $C_4$ alkylcarbonyl. In some embodiments, $R^{11}$ is $C_5$ alkylcarbonyl. In some other embodiments, $R^{11}$ is $C_6$ alkylcarbonyl. In other embodiments, $R^{11}$ is $C_7$ alkylcarbonyl. In yet other embodiments, $R^{11}$ is $C_8$ alkylcarbonyl. In some embodiments, $R^{11}$ is $C_9$ alkylcarbonyl. In yet other embodiments, $R^{11}$ is $C_{10}$ alkylcarbonyl. In some other embodiments, $R^{11}$ is $C_{11}$ alkylcarbonyl. In some embodiments, $R^{11}$ is $C_{12}$ alkylcarbonyl. In yet other embodiments, $R^{11}$ is —C(=O)(CH$_2$)$_n$CO$_2$H, where n is 1 to 6. For example, in some embodiments, n is 1. In other embodiments, n is 2. In yet other embodiments, n is 3. In some other embodiments, n is 4. In yet other embodiments, n is 5. In other embodiments, n is 6.

In other embodiments, $R^{11}$ is aryl. For example, in some embodiments, $R^{11}$ is phenyl. In some embodiments, the phenyl is substituted, for example with a nitro group.

In other embodiments, $R^{11}$ is heteroaryl. For example, in some embodiments, $R^{11}$ is pyridinyl. In other embodiments, $R^{11}$ is pyrimidinyl.

In other embodiments, $R^{11}$ is heterocyclyl. For example, in some embodiments, $R^1$ is piperidinyl, for example piperidin-4-yl.

In some embodiments, $R^{11}$ is ethyl, isopropyl, piperidinyl, pyrimidinyl, cholate, deoxycholate, or —C(=O)(CH$_2$)$_n$CO$_2$H, where n is 1 to 6.

In some embodiments, R is an electron pair. In other embodiments, R is hydrogen, and in other embodiments R is $C_1$-$C_{12}$ alkyl. In some embodiments, R is methyl. In some embodiments, R is ethyl. In other embodiments, R is $C_3$ alkyl. In yet other embodiments, R is isopropyl. In some other embodiments, R is $C_4$ alkyl. In yet other embodiments, R is $C_5$ alkyl. In some embodiments, R is $C_6$ alkyl. In other embodiments, R is $C_7$ alkyl. In yet other embodiments, R is $C_8$ alkyl. In other embodiments, R is $C_9$ alkyl. In some embodiments, R is $C_{10}$ alkyl. In yet other embodiments, R is $C_{11}$ alkyl. In some embodiments, R is $C_{12}$ alkyl.

In some embodiments, $R^{12}$ is, at each occurrence, independently, hydrogen, $C_1$-$C_{12}$ alkyl, $C_1$-$C_{12}$ aminoalkyl, —NH$_2$, —CONH$_2$, —NR$^{13}$R$^{14}$, —NR$^{13}$R$^{14}$R$^{15}$, oxo, —CN, trifluoromethyl, amidyl, amidinyl, amidinylalkyl, amidinylalkylcarbonyl, guanidinyl, guanidinylalkyl, guanidinylalkylcarbonyl, cholate, deoxycholate, aryl, heteroaryl, heterocycle, —SR$^{13}$ or $C_1$-$C_{12}$ alkoxy, wherein $R^{13}$, $R^{14}$ and $R^{15}$ are, at each occurrence, independently $C_1$-$C_{12}$ alkyl In some embodiments, $R^{12}$ is hydrogen. In some embodiments, $R^{12}$ is $C_1$-$C_{12}$ alkyl. In some embodiments, $R^{12}$ is $C_1$-$C_{12}$ aminoalkyl. In some embodiments, $R^{12}$ is —NH$_2$. In some embodiments, $R^{12}$ is —CONH$_2$. In some embodiments, $R^{12}$ is —$NR^{13}R^{14}$. In some embodiments, $R^{12}$ is —$NR^{13}R^{14}R^{15}$. In some embodiments, $R^{12}$ is $C_1$-$C_{12}$ alkylcarbonyl. In some embodiments, $R^{12}$ is oxo. In some embodiments, $R^{12}$ is —CN. In some embodiments, $R^{12}$ is trifluoromethyl. In some embodiments, $R^{12}$ is amidyl. In some embodiments, $R^{12}$ is amidinyl. In some embodiments, $R^{12}$ is amidinylalkyl. In some embodiments, $R^{12}$ is amidinylalkylcarbonyl. In some embodiments, $R^{12}$ is guanidinyl, for example mono methylguanidynyl or dimethylguanidinyl. In some embodiments, $R^{12}$ is guanidinylalkyl. In some embodiments, $R^{12}$ is amidinylalkylcarbonyl. In some embodiments, $R^{12}$ is cholate. In some embodiments, $R^{12}$ is deoxycholate. In some embodiments, $R^{12}$ is aryl. In some embodiments, $R^{12}$ is heteroaryl. In some embodiments, $R^{12}$ is heterocycle. In some embodiments, $R^{12}$ is —$SR^{13}$. In some embodiments, $R^{12}$ is $C_1$-$C_{12}$ alkoxy. In some embodiments, $R^{12}$ is dimethyl amine.

In other embodiments, $R^{12}$ is methyl. In yet other embodiments, $R^{12}$ is ethyl. In some embodiments, $R^{12}$ is $C_3$ alkyl. In some embodiments, $R^{12}$ is isopropyl. In some embodiments, $R^{12}$ is $C_4$ alkyl. In other embodiments, $R^{12}$ is $C_5$ alkyl. In yet other embodiments, $R^{12}$ is $C_6$ alkyl. In some other embodiments, $R^{12}$ is $C_7$ alkyl. In some embodiments, $R^{12}$ is $C_8$ alkyl. In yet other embodiments, $R^{12}$ is $C_9$ alkyl. In some embodiments, $R^{12}$ is $C_{10}$ alkyl. In yet other embodiments, $R^{12}$ is $C_{11}$ alkyl. In other embodiments, $R^{12}$ is $C_{12}$ alkyl. In yet other embodiments, the alkyl moiety is substituted with one or more oxygen atom to form an ether moiety, for example a methoxymethyl moiety.

In some embodiments, $R^{12}$ is methylamino. In other embodiments, $R^{12}$ is ethylamino. In yet other embodiments, $R^{12}$ is $C_3$ aminoalkyl. In some embodiments, $R^{12}$ is $C_4$ aminoalkyl. In yet other embodiments, $R^{12}$ is $C_5$ aminoalkyl. In some other embodiments, $R^{12}$ is $C_6$ aminoalkyl. In some embodiments, $R^{12}$ is $C_7$ aminoalkyl. In some embodiments, $R^{12}$ is $C_8$ aminoalkyl. In yet other embodiments, $R^{12}$ is $C_9$ aminoalkyl. In some other embodiments, $R^{12}$ is $C_{10}$ aminoalkyl. In yet other embodiments, $R^{12}$ is $C_{11}$ aminoalkyl. In other embodiments, $R^{12}$ is $C_{12}$ aminoalkyl. In some embodiments, the amino alkyl is a dimethylamino alkyl.

In yet other embodiments, $R^{12}$ is acetyl. In some other embodiments, $R^{12}$ is $C_2$ alkylcarbonyl. In some embodiments, $R^{12}$ is $C_3$ alkylcarbonyl. In yet other embodiments, $R^{12}$ is $C_4$ alkylcarbonyl. In some embodiments, $R^{12}$ is $C_5$ alkylcarbonyl. In some embodiments, $R^{12}$ is $C_6$ alkylcarbonyl. In some other embodiments, $R^{12}$ is $C_7$ alkylcarbonyl. In some embodiments, $R^{12}$ is $C_8$ alkylcarbonyl. In yet other embodiments, $R^{12}$ is $C_9$ alkylcarbonyl. In some other embodiments, $R^{12}$ is $C_{10}$ alkylcarbonyl. In some embodiments, $R^{12}$ is $C_{11}$ alkylcarbonyl. In other embodiments, $R^{12}$ is $C_{12}$ alkylcarbonyl. The alkylcarbonyl is substituted with a carboxy moiety, for example the alkylcarbonyl is substituted to form a succinic acid moiety (i.e., a 3-carboxyalkylcarbonyl). In other embodiments, the alkylcarbonyl is substituted with a terminal —SH group.

In some embodiments, $R^{12}$ is amidyl. In some embodiments, the amidyl comprises an alkyl moiety which is further substituted, for example with —SH, carbamate, or combinations thereof. In other embodiments, the amidyl is substituted with an aryl moiety, for example phenyl. In certain embodiments, $R^{12}$ may have the following structure (IX):

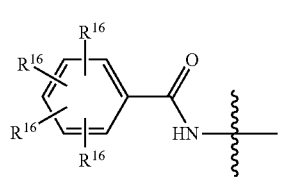

(IX)

wherein $R^{16}$ is, at each occurrence, independently hydrogen, $C_1$-$C_{12}$ alkyl, $C_1$-$C_{12}$ alkoxy, —CN, aryl or heteroaryl.

In some embodiments, $R^{12}$ is methoxy. In other embodiments, $R^{12}$ is ethoxy. In yet other embodiments, $R^{12}$ is $C_3$ alkoxy. In some embodiments, $R^{12}$ is $C_4$ alkoxy. In some embodiments, $R^{12}$ is $C_5$ alkoxy. In some other embodiments, $R^{12}$ is $C_6$ alkoxy. In other embodiments, $R^{12}$ is $C_7$ alkoxy. In some other embodiments, $R^{12}$ is $C_8$ alkoxy. In some embodiments, $R^{12}$ is $C_9$ alkoxy. In other embodiments, $R^{12}$ is $C_{10}$ alkoxy. In some embodiments, $R^{12}$ is $C_{11}$ alkoxy. In yet other embodiments, $R^{12}$ is $C_{12}$ alkoxy.

In certain embodiments, $R^{12}$ is pyrrolidinyl, for example pyrrolidin-1-yl. In other embodiments, $R^{12}$ is piperidinyl, for example piperidin-1-yl or piperidin-4-yl. In other embodiment, $R^{12}$ is morpholino, for example morpholin-4-yl. In other embodiments, $R^{12}$ is phenyl, and in even further embodiments, the phenyl is substituted, for example with a nitro group. In still other embodiments, $R^{12}$ is pyrimidinyl, for example pyrimidin-2-yl.

In other embodiments, $R^{13}$, $R^{14}$ and $R^{15}$ are, at each occurrence, independently $C_1$-$C_{12}$ alkyl. In some embodiments, $R^{13}$, $R^{14}$ or $R^{15}$ is methyl. In yet other embodiments, $R^{13}$, $R^{14}$ or $R^{15}$ is ethyl. In other embodiments, $R^{13}$, $R^{14}$ or $R^{15}$ is $C_3$ alkyl. In yet other embodiments, $R^{13}$, $R^{14}$ or $R^{15}$ is isopropyl. In other embodiments, $R^{13}$, $R^{14}$ or $R^{15}$ is $C_4$ alkyl. In some embodiments, $R^{13}$, $R^{14}$ or $R^{15}$ is $C_5$ alkyl. In some other embodiments, $R^{13}$, $R^{14}$ or $R^{15}$ is $C_6$ alkyl. In other embodiments, $R^{13}$, $R^{14}$ or $R^{15}$ is $C_7$ alkyl. In yet other embodiments, $R^{13}$, $R^{14}$ or $R^{15}$ is $C_8$ alkyl. In other embodiments, $R^{13}$, $R^{14}$ or $R^{15}$ is $C_9$ alkyl. In some embodiments, $R^{13}$, $R^{14}$ or $R^{15}$ is $C_{10}$ alkyl. In some embodiments, $R^{13}$, $R^{14}$ or $R^{15}$ is $C_{11}$ alkyl. In yet other embodiments, $R^{13}$, $R^{14}$ or $R^{15}$ is $C_{12}$ alkyl.

As noted above, in some embodiments, $R^{12}$ is amidyl substituted with an aryl moiety. In this regard, each occurrence of $R^{16}$ may be the same or different. In certain of these embodiments, $R^{16}$ is hydrogen. In other embodiments, $R^{16}$ is —CN. In other embodiments, $R^{16}$ is heteroaryl, for example tretrazolyl. In certain other embodiments, $R^{16}$ is methoxy. In other embodiments, $R^{16}$ is aryl, and the aryl is optionally substituted. Optional substituents in this regard include: $C_1$-$C_{12}$ alkyl, $C_1$-$C_{12}$ alkoxy, for example methoxy; trifluoromethoxy; halo, for example chloro; and trifluoromethyl.

In other embodiments, $R^{16}$ is methyl. In yet other embodiments, $R^{16}$ is ethyl. In some embodiments, $R^{16}$ is $C_3$ alkyl. In some other embodiments, $R^{16}$ is isopropyl. In yet other embodiments, $R^{16}$ is $C_4$ alkyl. In other embodiments, $R^{16}$ is $C_5$ alkyl. In yet other embodiments, $R^{16}$ is $C_6$ alkyl. In some other embodiments, $R^{16}$ is $C_7$ alkyl. In some embodiments, $R^{16}$ is $C_8$ alkyl. In yet other embodiments, $R^{16}$ is $C_9$ alkyl. In some other embodiments, $R^{16}$ is $C_{10}$ alkyl. In other embodiments, $R^{16}$ is $C_{11}$ alkyl. In other embodiments, $R^{16}$ is $C_{12}$ alkyl.

In some embodiments, $R^{16}$ is methoxy. In some embodiments, $R^{16}$ is ethoxy. In yet other embodiments, $R^{16}$ is $C_3$ alkoxy. In some other embodiments, $R^{16}$ is $C_4$ alkoxy. In other embodiments, $R^{16}$ is $C_5$ alkoxy. In some other embodiments, $R^{16}$ is $C_6$ alkoxy. In yet other embodiments, $R^{16}$ is $C_7$ alkoxy. In some embodiments, $R^{16}$ is $C_8$ alkoxy. In yet other embodiments, $R^{16}$ is $C_9$ alkoxy. In some other embodiments, $R^{16}$ is $C_{10}$ alkoxy. In some other embodiments, $R^{16}$ is $C_{11}$ alkoxy. In some other embodiments, $R^{16}$ is $C_{12}$ alkoxy.

In some other embodiments, $R^8$ and $R^9$ join to form a 12-18 membered crown ether. For example, in some embodiments, the crown ether s 18 membered, and in other embodiments the crown ether is 15 membered. In certain embodiments, $R^8$ and $R^9$ join to form a heterocycle having one of the following structures (X) or (XI):

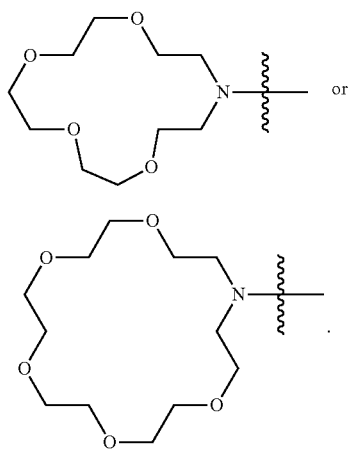

(X)

or (XI)

In some embodiments, $R^8$, $R^9$ or $R^3$ join with $R^{10}$ to form a 5-7 membered heterocycle. For example, in some embodiments, $R^3$ joins with $R^{10}$ to form a 5-7 membered heterocycle. In some embodiments, the heterocycle is 5-membered. In other embodiments, the heterocycle is 6-membered. In other embodiments, the heterocycle is 7-membered. In some embodiments, the heterocycle is represented by the following structure (XII):

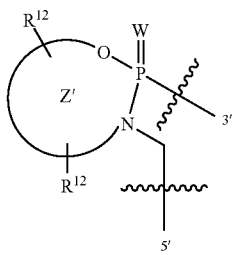

(XII)

wherein Z' represents a 5-7 membered heterocycle. In certain embodiments of structure (XI), $R^{12}$ is hydrogen at each occurrence. For example, linkage (B) may have one of the following structures (B1), (B2) or (B3):

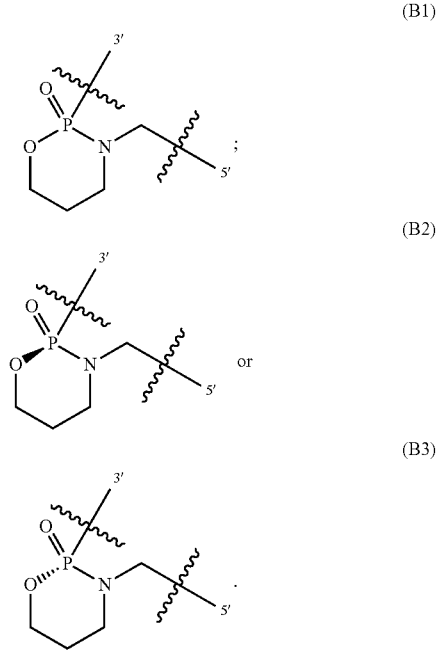

(B1)

(B2)

or (B3)

In certain other embodiments, $R^{12}$ is $C_1$-$C_{12}$ alkylcarbonyl or amidyl which is further substituted with an arylphosphoryl moiety, for example a triphenyl phosporyl moiety. Examples of linkages having this structure include B56 and B55.

In certain embodiment, linkage (B) does not have any of the structures A1-A5. Table 1 shows representative linkages of type (A) and (B).

TABLE 1

| | Representative Intersubunit Linkages | |
|---|---|---|
| No. | Name | Structure |
| A1 | PMO | |
| A2 | PMO+ (unprotonated form depicted) | |

TABLE 1-continued

Representative Intersubunit Linkages

| No. | Name | Structure |
|---|---|---|
| A3 | PMO⁺ (+) | 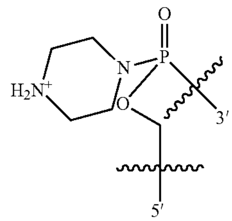 |
| A4 | PMO^mepip (m+) | 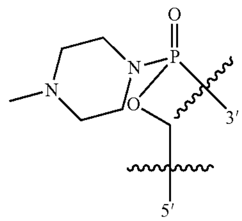 |
| A5 | PMO^GUX | 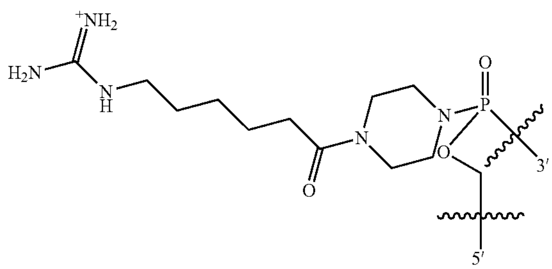 |
| B1 | PMO^cp | 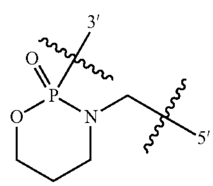 |
| B2 | PMO^cps | 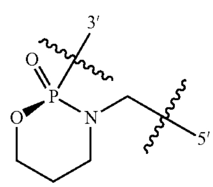 |
| B3 | PMO^cpr | 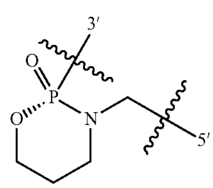 |
| B4 | PMO^Shc | 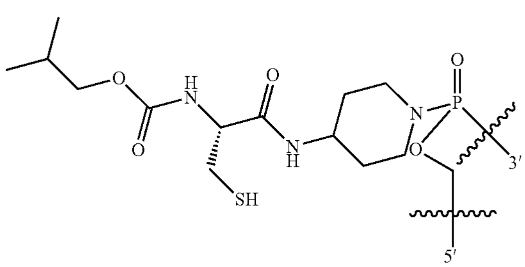 |

TABLE 1-continued
Representative Intersubunit Linkages
| No. | Name | Structure |
|---|---|---|
| B5 | PMO$^{moprpholino}$ (m) | 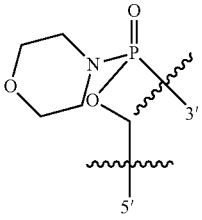 |
| B6 | PMO$^{tri}$ (t) | 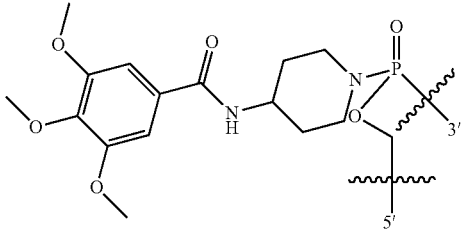 |
| B7 | PMO$^{hex}$ (h) | 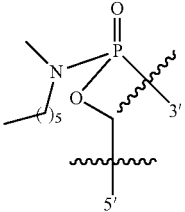 |
| B8 | PMO$^{dodec}$ | 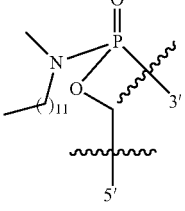 |
| B9 | PMO$^{dihex}$ | 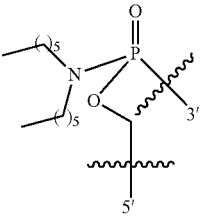 |
| B10 | PMO$^{apn}$ (a) | 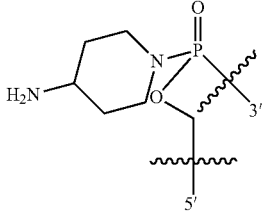 |

TABLE 1-continued

Representative Intersubunit Linkages

| No. | Name | Structure |
|---|---|---|
| B11 | PMO$^{pyr}$ (p) | 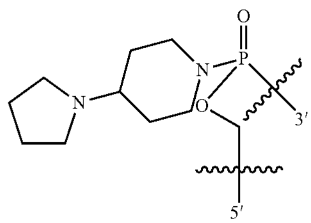 |
| B12 | PMO$^{pyr}$ (HCl Salt) | 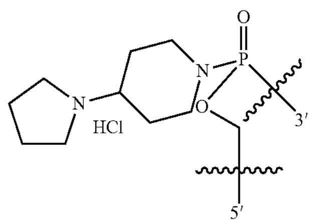 |
| B13 | PMO$^{rba}$ | 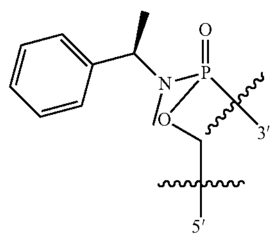 |
| B14 | PMO$^{sba}$ | 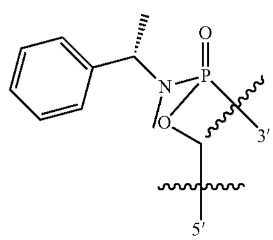 |
| B15 | PMO$^{dimethylapn}$ | 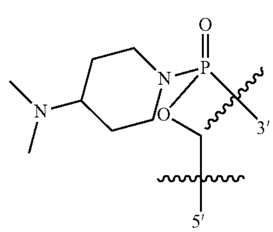 |
| B16 | PMO$^{etpip}$ | 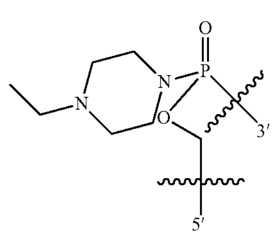 |

TABLE 1-continued
Representative Intersubunit Linkages
| No. | Name | Structure |
|---|---|---|
| B17 | PMO$^{iprpip}$ | 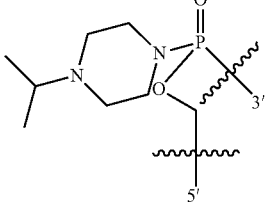 |
| B18 | PMO$^{pyrQMe}$ | 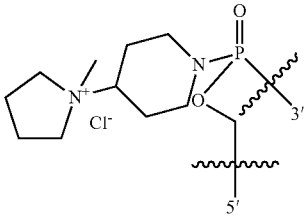 |
| B19 | PMO$^{cb}$ | 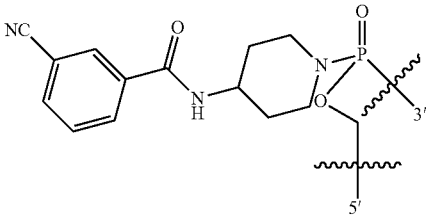 |
| B20 | PMO$^{ma}$ | 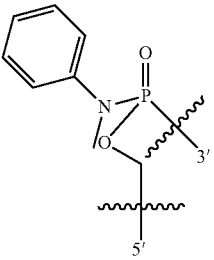 |
| B21 | PMO$^{bu}$ | 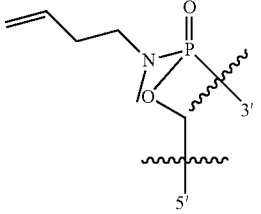 |
| B22 | PMO$^{bi}$ | 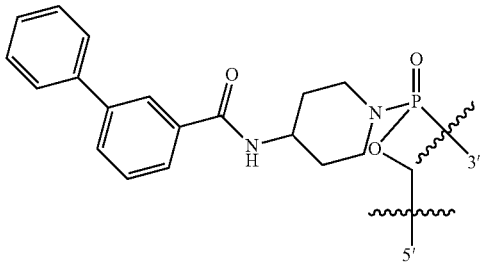 |

TABLE 1-continued

Representative Intersubunit Linkages

| No. | Name | Structure |
|---|---|---|
| B23 | PMO$^{pip}$ | 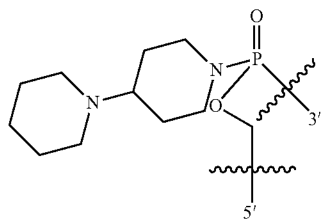 |
| B24 | PMO$^{odmb}$ | 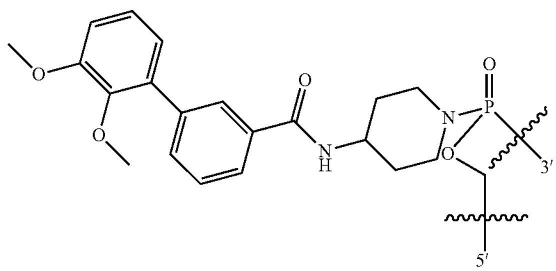 |
| B25 | PMO$^{tfb}$ | 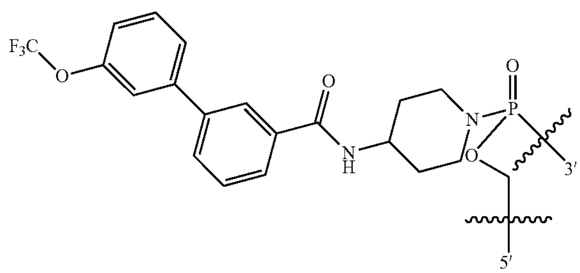 |
| B26 | PMO$^{ctfb}$ | 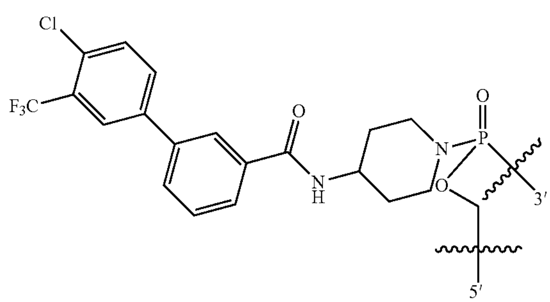 |
| B27 | PMO$^{ptfb}$ | 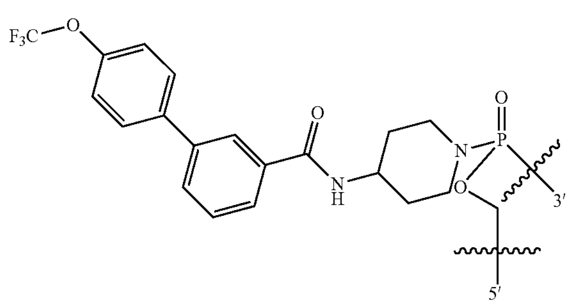 |

TABLE 1-continued

Representative Intersubunit Linkages

| No. | Name | Structure |
|---|---|---|
| B28 | PMO$^{dcb}$ | 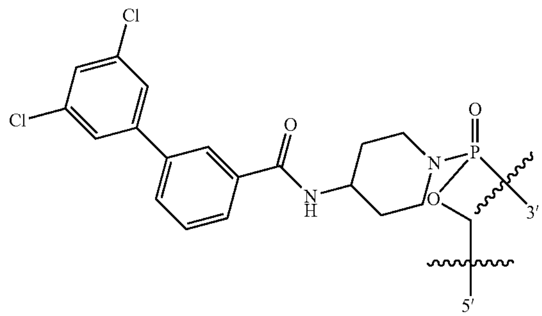 |
| B29 | PMO$^{dmb}$ | 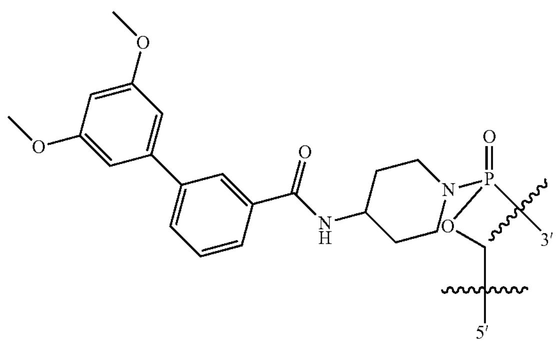 |
| B30 | PMO$^{hy}$ | 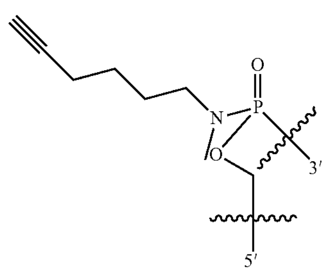 |
| B31 | PMO$^{6ce}$ | 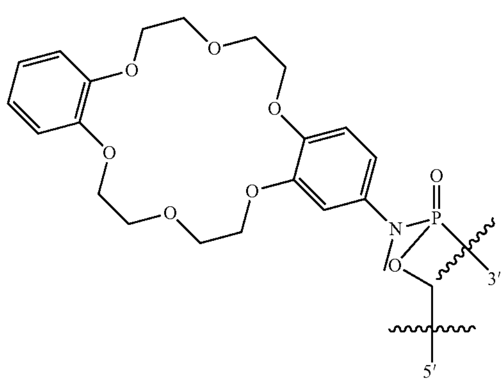 |
| B32 | PMO$^{b}$ | 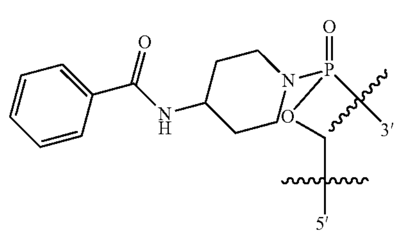 |

TABLE 1-continued
Representative Intersubunit Linkages
| No. | Name | Structure |
|---|---|---|
| B33 | PMO$^q$ | 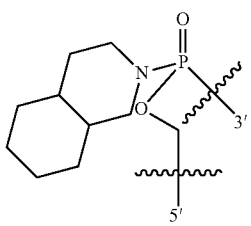 |
| B34 | PMO$^{npp}$ | 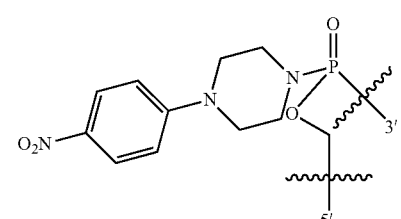 |
| B35 | PMO$^o$ | 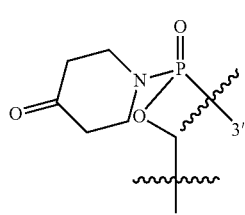 |
| B36 | PMO$^{4ce}$ | 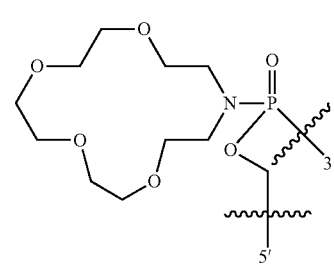 |
| B37 | PMO$^{5ce}$ | 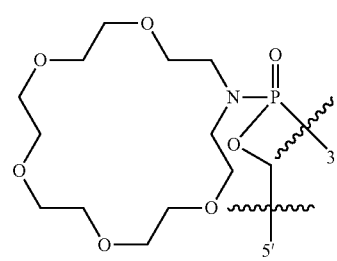 |
| B38 | PMO$^{f3p}$ | 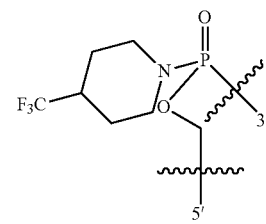 |

TABLE 1-continued
Representative Intersubunit Linkages
| No. | Name | Structure |
|---|---|---|
| B39 | PMO<sup>cyp</sup> | 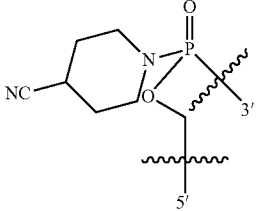 |
| B40 | PMO<sup>mop</sup> | 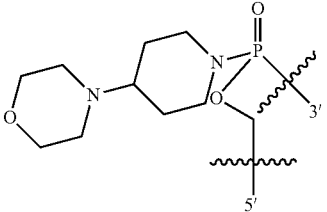 |
| B41 | PMO<sup>pp</sup> | 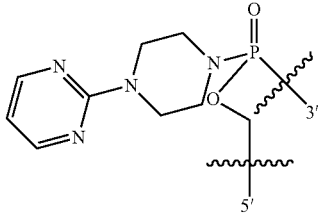 |
| B42 | PMO<sup>dmepip</sup> | 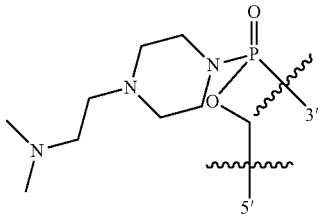 |
| B43 | PMO<sup>NPpip</sup> | 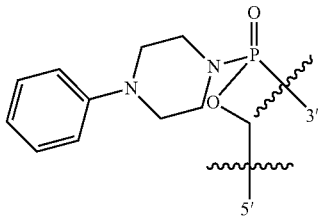 |
| B44 | PMO<sup>bipip</sup> | 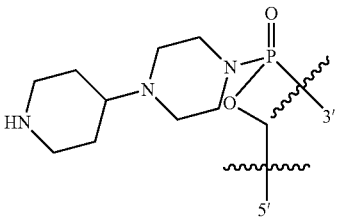 |

TABLE 1-continued

Representative Intersubunit Linkages

| No. | Name | Structure |
|---|---|---|
| B45 | PMO$^{suc}$ | 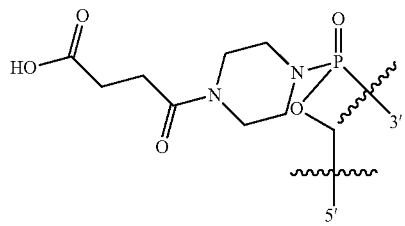 |
| 46 | PMO$^{glutaric}$ | 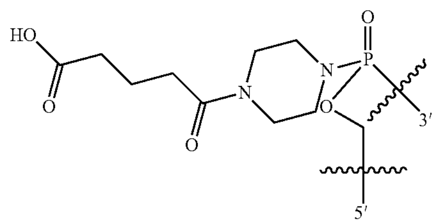 |
| B47 | PMO$^{tet}$ | 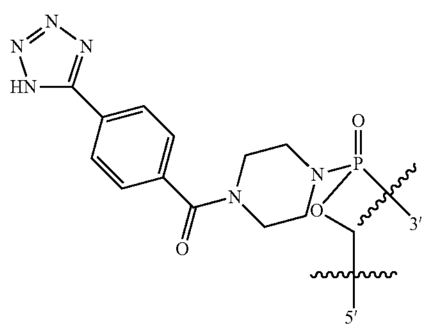 |
| B48 | PMO$^{thiol}$ (SH) | 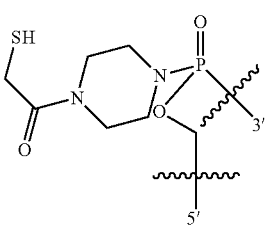 |
| B49 | PMO$^{pros}$ | 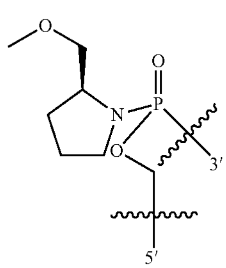 |
| B50 | PMO$^{pror}$ | 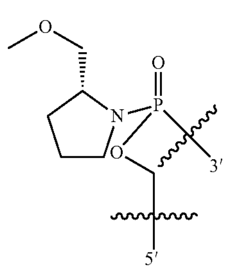 |

TABLE 1-continued

Representative Intersubunit Linkages

| No. | Name | Structure |
|---|---|---|
| B51 | PMO$^{tme}$ | 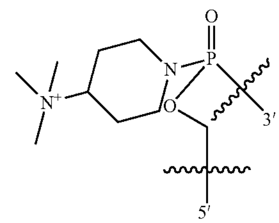 |
| B52 | PMO$^{ca}$ | 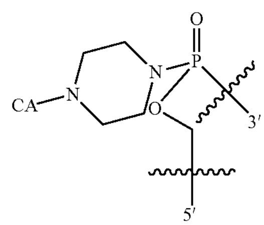 |

CA = Cholate

| B53 | PMO$^{dca}$ | | dCA = Cholate

| B54 | PMO$^{guan}$ (g) | |
| B55 | PMO$^{tphos}$ | |

TABLE 1-continued

Representative Intersubunit Linkages

| No. | Name | Structure |
|---|---|---|
| B56 | PMO$^{apnphos}$ | 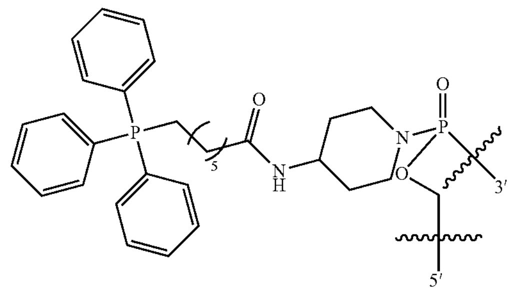 |

In the sequences and discussion that follows, the above names for the linkages are often used. For example, a base comprising a PMO$^{apn}$ linkage is illustrated as $^{apn}$B, where B is a base. Other linkages are designated similarly. In addition, abbreviated designations may be used, for example, the abbreviated designations in parentheses above may be used (e.g., $^{a}$B, refers to $^{apn}$B). Other readily identifiable abbreviations may also be used.

B. Oligomers with Modified Terminal Groups

As noted above, the present disclosure also provides an oligomer comprising modified terminal groups. Applicants have found that modification of the 3' and/or 5' end of the oligomer with various chemical moieties provides beneficial therapeutic properties (e.g., enhanced cell delivery, potency, and/or tissue distribution, etc.) to the oligomers. In various embodiments, the modified terminal groups comprise a hydrophobic moiety, while in other embodiments the modified terminal groups comprise a hydrophilic moiety. The modified terminal groups may be present with or without the linkages described above. For example, in some embodiments, the oligomers comprise one or more modified terminal group and linkages of type (A), for example linkages wherein X is —N(CH$_3$)$_2$. In other embodiments, the oligomers comprise one or more modified terminal group and linkages of type (B), for example linkages wherein X is 4-aminopiperidin-1-yl (i.e., APN). In yet other embodiments, the oligomers comprise one or more modified terminal group and a mixture of linkages (A) and (B). For example, the oligomers may comprise one or more modified terminal group (e.g., trityl or triphenyl acetyl) and linkages wherein X is —N(CH$_3$)$_2$ and linkages wherein X is 4-aminopiperidin-1-yl. Other combinations of modified terminal groups and modified linkages also provide favorable therapeutic properties to the oligomers.

In one embodiment, the oligomers comprising terminal modifications have the following structure (XVII):

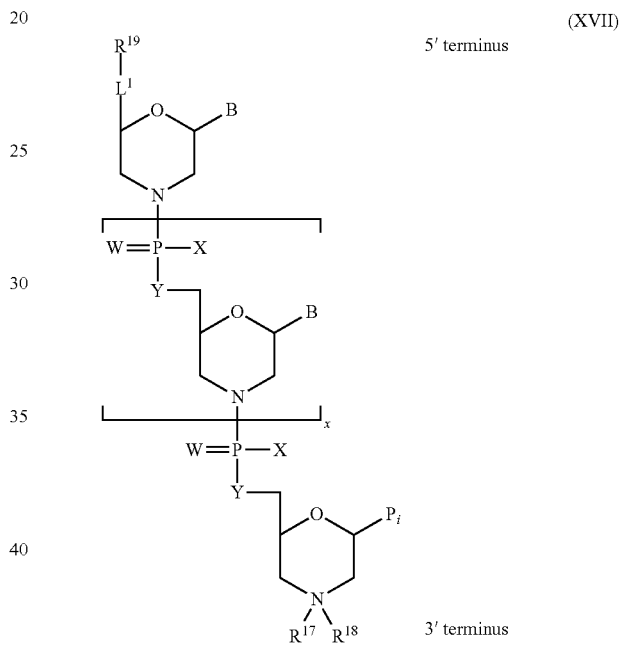

(XVII)

or a salt or isomer thereof, wherein X, W and Y are as defined above for any of linkages (A) and (B) and:

R$^{17}$ is, at each occurrence, independently absent, hydrogen or C$_1$-C$_6$ alkyl;

R$^{18}$ and R$^{19}$ are, at each occurrence, independently absent, hydrogen, a cell-penetrating peptide, a natural or non-natural amino acid, C$_2$-C$_{30}$ alkylcarbonyl, —C(=O)OR$^{21}$ or R$^{20}$;

R$^{20}$ is, at each occurrence, independently guanidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_3$-C$_{30}$ alkylcarbonyl, C$_3$-C$_8$ cycloalkylcarbonyl, C$_3$-C$_8$ cycloalkylalkylcarbonyl, C$_7$-C$_{30}$ arylcarbonyl, C$_7$-C$_{30}$ aralkylcarbonyl, C$_2$-C$_{30}$ alkyloxycarbonyl, C$_3$-C$_8$ cycloalkyloxycarbonyl, C$_7$-C$_{30}$ aryloxycarbonyl, C$_8$-C$_{30}$ aralkyloxycarbonyl, or —P(=O)(R$^{22}$)$_2$;

B is a base-pairing moiety;

L$^1$ is an optional linker up to 18 atoms in length comprising bonds selected from alkyl, hydroxyl, alkoxy, alkylamino, amide, ester, disulfide, carbonyl, carbamate, phosphorodiamidate, phosphoroamidate, phosphorothioate, piperazine and phosphodiester; and x is an integer of 0 or greater; and wherein at least one of R$^{18}$ or R$^{19}$ is R$^{20}$; and wherein at least one of $R^{18}$ or $R^{19}$ is $R^{20}$ and provided that both of $R^{17}$ and $R^{18}$ are not absent.

The oligomers with modified terminal groups may comprise any number of linkages of types (A) and (B). For example, the oligomers may comprise only linkage type (A). For example, X in each linkage may be —N(CH$_3$)$_2$. Alternatively, the oligomers may only comprise linkage (B). In certain embodiments, the oligomers comprise a mixture of linkages (A) and (B), for example from 1 to 4 linkages of type (B) and the remainder of the linkages being of type (A). Linkages in this regard include, but are not limited to, linkages wherein X is aminopiperidinyl for type (B) and dimethyl amino for type (A).

In some embodiments, $R^{17}$ is absent. In some embodiments, $R^{17}$ is hydrogen. In some embodiments, $R^{17}$ is $C_1$-$C_6$ alkyl. In some embodiments, $R^{17}$ is methyl. In yet other embodiments, $R^{17}$ is ethyl. In some embodiments, $R^{17}$ is $C_3$ alkyl. In some other embodiments, $R^{17}$ is isopropyl. In other embodiments, $R^{17}$ is $C_4$ alkyl. In yet other embodiments, $R^{17}$ is $C_5$ alkyl. In some other embodiments, $R^{17}$ is $C_6$ alkyl.

In other embodiments, $R^{18}$ is absent. In some embodiments, $R^{18}$ is hydrogen. In some embodiments, $R^{18}$ is a cell-penetrating peptide as described in more detail below. In some embodiments, $R^{18}$ is a natural or non-natural amino acid, for example trimethylglycine. In some embodiments, $R^{18}$ is $R^{20}$.

In other embodiments, $R^{19}$ is absent. In some embodiments, $R^{19}$ is hydrogen. In some embodiments, $R^{19}$ is a cell-penetrating peptide as described in more detail below. In some embodiments, $R^{19}$ is a natural or non-natural amino acid, for example trimethylglycine. In some embodiments, $R^{19}$ is —C(=O)OR$^7$, for example $R^{19}$ may have the following structure:

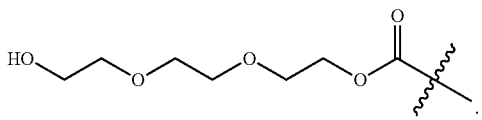 [SMILES: *C(=O)OCCOCCOCCO]

In other embodiments $R^{18}$ or $R^{19}$ is $C_2$-$C_{30}$ alkylcarbonyl, for example —C(=O)(CH$_2$)$_n$CO$_2$H, where n is 1 to 6, for example 2. In other examples, $R^{18}$ or $R^{19}$ is acetyl.

In some embodiments, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, —C(=O)OR$^{21}$, or —P(=O)(R$^{22}$)$_2$, wherein $R^{21}$ is $C_1$-$C_{30}$ alkyl comprising one or more oxygen or hydroxyl moieties or combinations thereof and each $R^{22}$ is $C^6$-$C^{12}$ aryloxy.

In certain other embodiments, $R^{19}$ is —C(=O)OR$^{21}$ and $R^{18}$ is hydrogen, guanidinyl, heterocyclyl, $C_1$-$C_{30}$ alkyl, $C_3$-$C_8$ cycloalkyl; $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$, wherein each $R^{22}$ is $C^6$-$C^{12}$ aryloxy.

In other embodiments, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$. While in other examples, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$.

In some embodiments $R^{20}$ is guanidinyl, for example mono methylguanidynyl or dimethylguanidinyl. In other embodiments, $R^{20}$ is heterocyclyl. For example, in some embodiments, $R^{20}$ is piperidin-4-yl. In some embodiments, the piperidin-4-yl is substituted with trityl or Boc groups. In other embodiments, $R^{20}$ is $C_3$-$C_8$ cycloalkyl. In other embodiments, $R^{20}$ is $C_6$-$C_{30}$ aryl.

In some embodiments, $R^{20}$ is $C_7$-$C_{30}$ arylcarbonyl. For example, In some embodiments, $R^{20}$ has the following structure (XVIII):

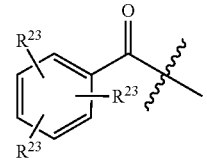

(XVIII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. In some embodiments, at least one $R^{23}$ is hydrogen, for example, in some embodiments, each $R^{23}$ is hydrogen. In other embodiments, at least one $R^{23}$ is $C_1$-$C_{30}$ alkoxy, for example in some embodiments, each $R^{23}$ is methoxy. In other embodiments, at least one $R^{23}$ is heteroaryl, for example in some embodiments, at least one $R^{23}$ has one of the following structures (XVIIIa) of (XVIIIb):

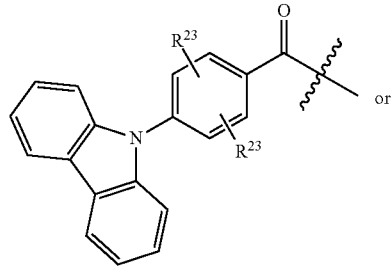

(XVIIIa)

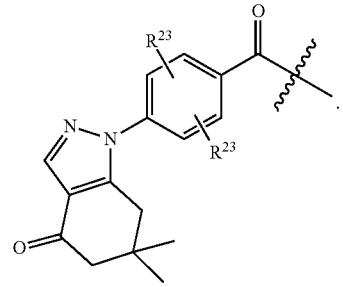

(XVIIIb)

In still other embodiments, one $R^{23}$ joins with another $R^{23}$ to form a heterocyclyl ring. For example, in one embodiment, $R^{20}$ is 5-carboxyfluorescein.

In other embodiments, $R^{20}$ is $C_7$-$C_{30}$ aralkylcarbonyl. For example, in various embodiments, $R^{20}$ has one of the following structures (XIX), (XX) or (XXI):

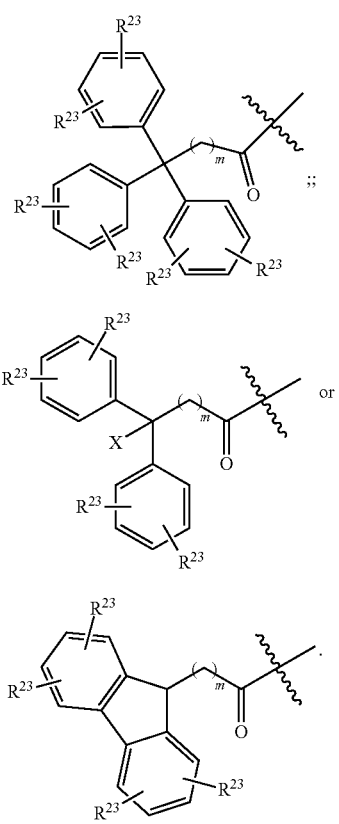

(XIX)

(XX)

(XXI)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, wherein one $R^{23}$ may join with another $R^{23}$ to form a heterocyclyl ring, X is —OH or halo and m is an integer from 0 to 6. In some specific embodiments, m is 0. In other embodiments, m is 1, while in other embodiments, m is 2. In other embodiments, at least one $R^{23}$ is hydrogen, for example in some embodiments each $R^{23}$ is hydrogen. In some embodiments, X is hydrogen. In other embodiments, X is —OH. In other embodiments, X is $C_1$. In other embodiments, at least one $R^{23}$ is $C_1$-$C_{30}$ alkoxy, for example methoxy.

In still other embodiments, $R^{20}$ is $C_7$-$C_{30}$ aralkyl, for example trityl. In other embodiments, $R^{20}$ is methoxy trityl. In some embodiments, $R^{20}$ has the following structure (XXII):

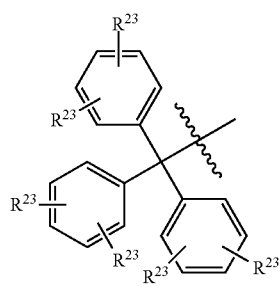

(XXII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. For example, in some embodiments each $R^{23}$ is hydrogen. In other embodiments, at least one $R^{23}$ is $C_1$-$C_{30}$ alkoxy, for example methoxy.

In yet other embodiments, $R^{20}$ is $C_7$-$C_{30}$ aralkyl and $R^{20}$ has the following structure (XXIII):

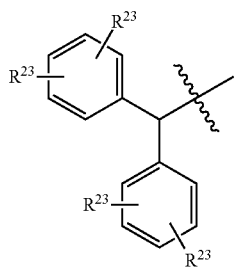

(XXIII)

In some embodiments, at least one $R^{23}$ is halo, for example chloro. In some other embodiments, one $R^{23}$ is chloro in the para position.

In other embodiments, $R^{20}$ is $C_1$-$C_{30}$ alkyl. For example, In some embodiments, $R^{20}$ is a $C_4$-$C_{20}$ alkyl and optionally comprises one or more double bonds. For example, In some embodiments, $R^{20}$ is a $C_{4-10}$ alkyl comprising a triple bond, for example a terminal triple bond. In some embodiments, $R^{20}$ is hexyn-6-yl. In some embodiments, $R^{20}$ has one of the following structures (XXIV), (XXV), (XXVI) or (XXVII):

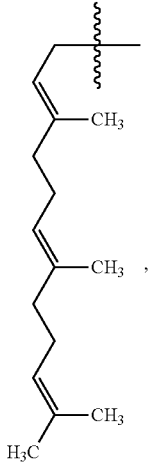

(XXIV)

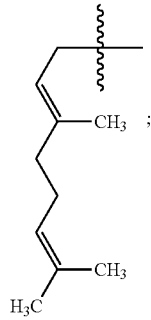

(XXV)

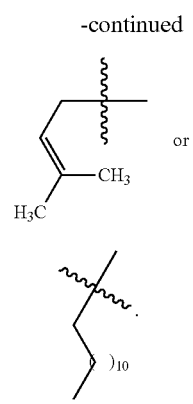

(XXVI) or (XXVII)

In still other embodiments, $R^{20}$ is a $C_3$-$C_{30}$ alkylcarbonyl, for example a $C_3$-$C_{10}$ alkyl carbonyl. In some embodiments, $R^{20}$ is —C(=O)(CH$_2$)$_p$SH or —C(=O)(CH$_2$)$_p$SSHet, wherein p is an integer from 1 to 6 and Het is a heteroaryl. For example, p may be 1 or p may be 2. In other example Het is pyridinyl, for example pyridin-2-yl. In other embodiments, the $C_3$-$C_{30}$ alkylcarbonyl is substituted with a further oligomer, for example in some embodiments the oligomer comprises a $C_3$-$C_{30}$ alkyl carbonyl at the 3' position which links the oligomer to the 3' position of another oligomer. Such terminal modifications are included within the scope of the present disclosure.

In other embodiments, $R^{20}$ is a $C_3$-$C_{30}$ alkyl carbonyl which is further substituted with an arylphosphoryl moiety, for example triphenyl phosphoryl. Examples of such $R^{20}$ groups include structure 33 in Table 2.

In other examples, $R_{20}$ is $C_3$-$C_8$ cycloalkylcarbonyl, for example $C_5$-$C_7$ alkyl carbonyl. In these embodiments, $R_{20}$ has the following structure (XXVIII):

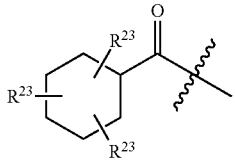

(XXVIII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. In some embodiments, $R^{23}$ is heterocyclylalkyl, for example in some embodiments $R^{23}$ has the following structure:

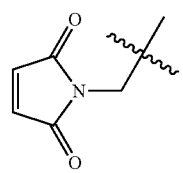 [SMILES: *CN1C(=O)C=CC1=O]

In some other embodiments, $R^{20}$ is $C_3$-$C_8$ cycloalkylalkylcarbonyl. In other embodiments, $R^{20}$ is $C_2$-$C_{30}$ alkyloxycarbonyl. In other embodiments, $R^{20}$ is $C_3$-$C_8$ cycloalkyloxycarbonyl. In other embodiments, $R^{20}$ is $C_7$-$C_{30}$ aryloxycarbonyl. In other embodiments, $R^{20}$ is $C_8$-$C_{30}$ aralkyloxycarbonyl. In other embodiments, $R^{20}$ is —P(=O)(R$^{22}$)$_2$, wherein each $R^{22}$ is $C^6$-$C^{12}$ aryloxy, for example in some embodiments $R^{20}$ has the following structure (C24):

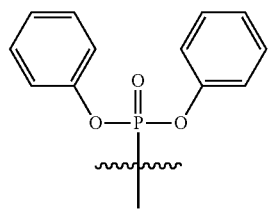

(C24)

In other embodiments, R comprises one or more halo atoms. For example, in some embodiments $R^{20}$ comprises a perfluoro analogue of any of the above $R^{20}$ moieties. In other embodiments, $R^{20}$ is p-trifluoromethylphenyl, trifluoromethyltrityl, perfluoropentyl or pentafluorophenyl.

In some embodiments the 3' terminus comprises a modification and in other embodiments the 5' terminus comprises a modification. In other embodiments both the 3' and 5' termini comprise modifications. Accordingly, in some embodiments, $R^{18}$ is absent and $R^{19}$ is $R^{20}$. In other embodiments, $R^{19}$ is absent and $R^{18}$ is $R^{20}$. In yet other embodiments, $R^{18}$ and $R^{19}$ are each $R^{20}$.

In some embodiments, the oligomer comprises a cell-penetrating peptide in addition to a 3' or 5' modification. Accordingly, in some embodiments $R^{19}$ is a cell-penetrating peptide and $R^{18}$ is $R^{20}$. In other embodiments, $R^{18}$ is a cell-penetrating peptide and $R^{19}$ is $R^{20}$. In further embodiments of the foregoing, the cell-penetrating peptide is an arginine-rich peptide.

In some embodiments, the linker $L^1$ which links the 5'terminal group (i.e., $R^{19}$) to the oligomer may be present or absent. The linker comprises any number of functional groups and lengths provided the linker retains its ability to link the 5' terminal group to the oligomer and provided that the linker does not interfere with the oligomer's ability to bind to a target sequence in a sequence specific manner. In one embodiment, L comprises phosphorodiamidate and piperazine bonds. For example, in some embodiments L has the following structure (XXIX):

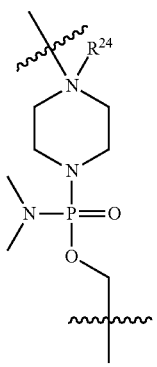

(XXIX)

wherein $R^{24}$ is absent, hydrogen or $C_1$-$C_6$ alkyl. In some embodiments, $R^{24}$ is absent. In some embodiments, $R^{24}$ is hydrogen. In some embodiments, $R^{24}$ is $C_1$-$C_6$ alkyl. In some embodiments, $R^{24}$ is methyl. In other embodiments, $R^{24}$ is ethyl. In yet other embodiments, $R^{24}$ is $C_3$ alkyl. In some other embodiments, $R^{24}$ is isopropyl. In yet other embodiments, $R^{24}$ is $C_4$ alkyl. In some embodiments, $R^{24}$ is $C_5$ alkyl. In yet other embodiments, $R^{24}$ is $C_6$ alkyl.

In yet other embodiments, $R^{20}$ is $C_3$-$C_{30}$ alkylcarbonyl, and $R^{20}$ has the following structure (XXX):

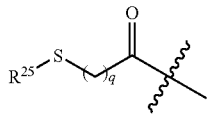

(XXX)

wherein $R^{25}$ is hydrogen or —$SR^{26}$, wherein $R^{26}$ is hydrogen, $C_1$-$C_{30}$ alkyl, heterocyclyl, aryl or heteroaryl, and q is an integer from 0 to 6.

In further embodiments of any of the above, $R^{23}$ is, at each occurrence, independently hydrogen, halo, $C_1$-$C_{30}$ alkyl, $C_1$-$C_{30}$ alkoxy, aryl, heteroaryl, heterocyclyl or heterocyclalkyl.

In some other embodiments, only the 3' terminus of the oligomer is conjugated to one of the groups noted above. In some other embodiments, only the 5' terminus of the oligomer is conjugated to one of the groups noted above. In other embodiments, both the 3' and 5' termini comprise one of the groups noted above. The terminal group may be selected from any one of the groups noted above or any of the specific groups illustrated in Table 2.

TABLE 2

Representative Terminal Groups

| No. | Name | Structure |
|---|---|---|
| C1 | Trimethoxybenzoyl | 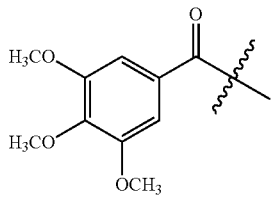 [SMILES: *C(=O)c1cc(OC)c(OC)c(OC)c1] |
| C2 | 9-fluorene-carboxyl | 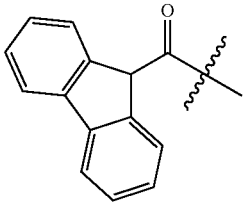 [SMILES: *C(=O)C1c2ccccc2-c2ccccc21] |
| C3 | 4-carbazolylbenzoyl | 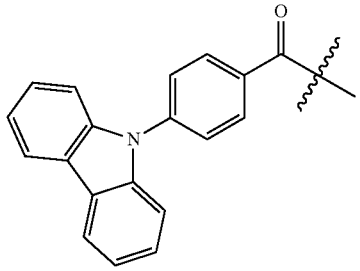 [SMILES: *C(=O)c1ccc(-n2c3ccccc3c3ccccc32)cc1] |
| C4 | 4-indazolylonebenzoyl | 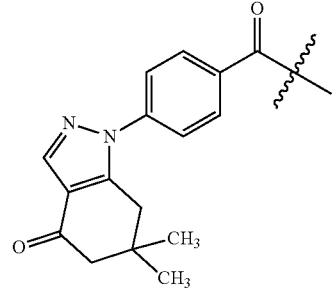 [SMILES: *C(=O)c1ccc(-n2ncc3c2CC(C)(C)CC3=O)cc1] |
| C5 | Farnesyl | 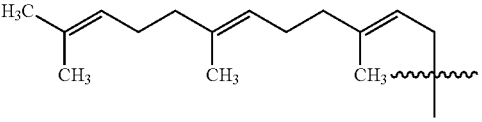 [SMILES: *C/C=C(\C)CC/C=C(\C)CCC=C(C)C] |

TABLE 2-continued

| | Representative Terminal Groups | |
|---|---|---|
| No. | Name | Structure |
| C6 | Geranyl | (structure) |
| C7 | Prenyl | (structure) |
| C8 | Diphenylacetyl | (structure) |
| C9 | Chlorodiphenylacetyl | (structure) |
| C10 | Hydroxydiphenylacetyl | (structure) |
| C11 | Triphenylpropionyl | (structure) |
| C12 | Triphenylpropyl | (structure) |

TABLE 2-continued
Representative Terminal Groups
| No. | Name | Structure |
|---|---|---|
| C13 | Triphenylacetyl | 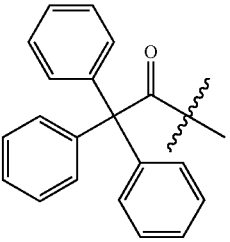 [SMILES: *C(=O)C(c1ccccc1)(c1ccccc1)c1ccccc1] |
| C14 | Trityl (Tr) | 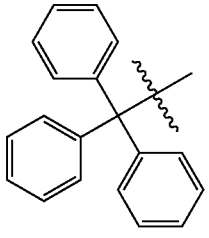 [SMILES: *C(c1ccccc1)(c1ccccc1)c1ccccc1] |
| C15 | Methoxytrityl (MeOTr) | 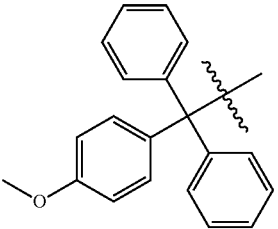 [SMILES: *C(c1ccccc1)(c1ccccc1)c1ccc(OC)cc1] |
| C16 | Methylsuccinimidyl-cyclohexyl | 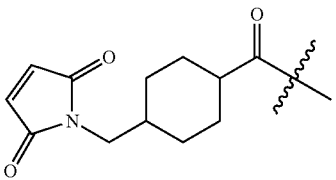 [SMILES: *C(=O)C1CCC(CN2C(=O)C=CC2=O)CC1] |
| C17 | Thioacetyl | 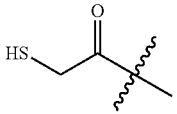 [SMILES: *C(=O)CS] |
| C18 | COCH$_2$CH$_2$SSPy | 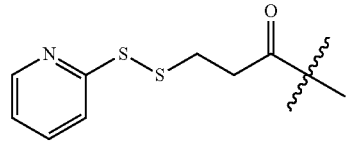 [SMILES: *C(=O)CCSSc1ccccn1] |
| C19 | Guanidinyl | 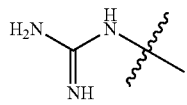 |
| C20 | Trimethylglycine | 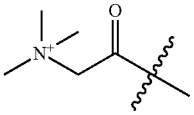 [SMILES: *C(=O)C[N+](C)(C)C] |

TABLE 2-continued
Representative Terminal Groups
| No. | Name | Structure |
|---|---|---|
| C21 | Lauroyl | 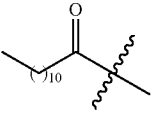 |
| C22 | Triethyleneglycoloyl (EG3) | 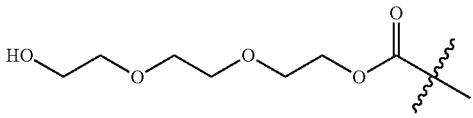 [SMILES: *C(=O)OCCOCCOCCO] |
| C23 | Succinicacetyl | 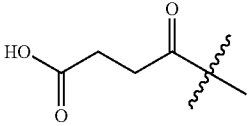 [SMILES: *C(=O)CCC(=O)O] |
| C24 | Diphenylphosphoryl | 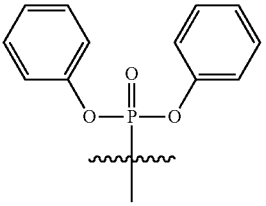 |
| C25 | Piperidin-4-yl | 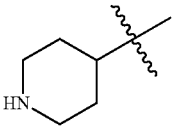 [SMILES: *C1CCNCC1] |
| C26 | Tritylpiperidin-4-yl | 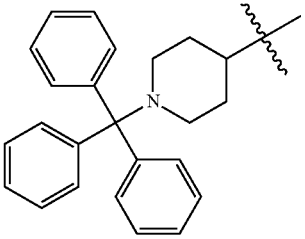 [SMILES: *C1CCN(C(c2ccccc2)(c2ccccc2)c2ccccc2)CC1] |
| C27 | Boc-Piperidin-4-yl | 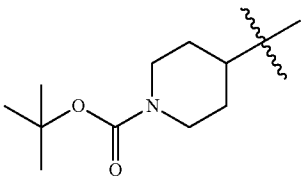 [SMILES: *C1CCN(C(=O)OC(C)(C)C)CC1] |
| C28 | Hexyn-6-yl | 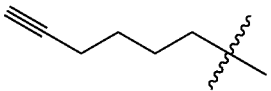 [SMILES: *CCCCC#C] |

TABLE 2-continued

Representative Terminal Groups

| No. | Name | Structure |
|---|---|---|
| C29 | 5-carboxyfluorescein | 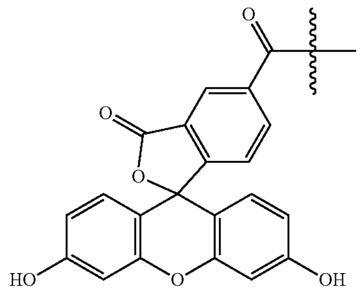 [SMILES: *C(=O)c1ccc2c(c1)C(=O)OC21c2ccc(O)cc2Oc2cc(O)ccc21] |
| C30 | Benzhydryl | 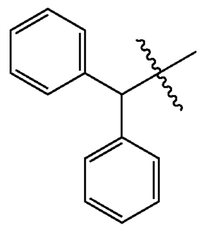 [SMILES: *C(c1ccccc1)c1ccccc1] |
| C31 | p-Chlorobenzhydryl | 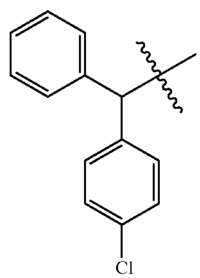 [SMILES: *C(c1ccccc1)c1ccc(Cl)cc1] |
| C32 | Piperazinyl (pip) | 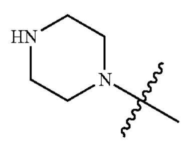 [SMILES: *N1CCNCC1] |
| C33 | Triphenylphos | 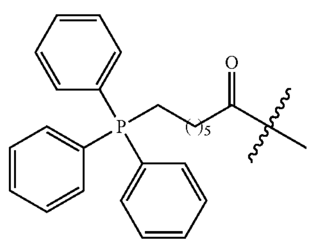 |
| C34 | Dimerized | 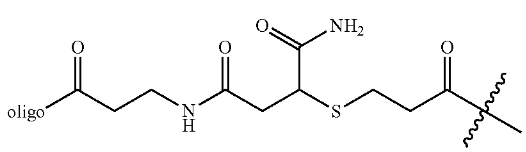 |

Oligo = a further oligomer

1. Peptide Transporters

In some embodiments, the subject oligomer is conjugated to a peptide transporter moiety, for example a cell-penetrating peptide transport moiety, which is effective to enhance transport of the oligomer into cells. For example, in some embodiments the peptide transporter moiety is an arginine-rich peptide. In further embodiments, the transport moiety is attached to either the 5' or 3' terminus of the oligomer, as shown, for example, in FIG. 1C. When such peptide is conjugated to either termini, the opposite termini is then available for further conjugation to a modified terminal group as described herein.

In some embodiments of the foregoing, the peptide transport moiety comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^{33}N=C(NH_2)R^{34}$, where $R^{33}$ is H or R; $R^{34}$ is $R^{35}$, $NH_2$, NHR, or $NR_{34}$, where $R^{35}$ is lower alkyl or lower alkenyl and may further include oxygen or nitrogen; $R^{33}$ and $R^{34}$ may together form a ring; and the side chain is linked to said amino acid via $R^{33}$ or $R^{34}$;

(b) each Y' subunit independently represents a neutral amino acid $—C(O)—(CHR)_n—NH—$, where n is 2 to 7 and each R is independently H or methyl; and (c) each Z' subunit independently represents an α-amino acid having a neutral aralkyl side chain;

wherein the peptide comprises a sequence represented by one of $(X'Y'X')_p$, $(X'Y')_m$, and $(X'Z'Z')_p$, where p is 2 to 5 and m is 2 to 8.

In selected embodiments, for each X', the side chain moiety is guanidyl, as in the amino acid subunit arginine (Arg). In further embodiments, each Y' is $—CO—(CH_2)_n—CHR—NH—$, where n is 2 to 7 and R is H. For example, when n is 5 and R is H, Y' is a 6-aminohexanoic acid subunit, abbreviated herein as Ahx; when n is 2 and R is H, Y' is a β-alanine subunit.

In certain embodiments, peptides of this type include those comprising arginine dimers alternating with single Y' subunits, where Y' is Ahx. Examples include peptides having the formula $(RY'R)_p$ or the formula $(RRY')_p$, where Y' is Ahx. In one embodiment, Y' is a 6-aminohexanoic acid subunit, R is arginine and p is 4.

In a further embodiment, each Z' is phenylalanine, and m is 3 or 4.

In some embodiments, the conjugated peptide is linked to a terminus of the oligomer via a linker Ahx-B, where Ahx is a 6-aminohexanoic acid subunit and B is a β-alanine subunit.

In selected embodiments, for each X', the side chain moiety is independently selected from the group consisting of guanidyl ($HN=C(NH_2)NH—$), amidinyl ($HN=C(NH_2)C—$), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In some embodiments, the Y' subunits are either contiguous, in that no X' subunits intervene between Y' subunits, or interspersed singly between X' subunits. However, in some embodiments the linking subunit may be between Y' subunits. In one embodiment, the Y' subunits are at a terminus of the peptide transporter; in other embodiments, they are flanked by X' subunits. In further embodiments, each Y' is $—CO—(CH_2)_n—CHR—NH—$, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Exemplary peptides of this type include those comprising arginine dimers alternating with single Y' subunits, where Y' is preferably Ahx. Examples include peptides having the formula $(RY'R)_4$ or the formula $(RRY')_4$, where Y' is preferably Ahx. In some embodiments, the nucleic acid analog is linked to a terminal Y' subunit, preferably at the C-terminus, as shown, for example, in FIG. 1C. In other embodiments, the linker is of the structure AhxB, where Ahx is a 6-aminohexanoic acid subunit and B is a β-alanine subunit.

The peptide transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake may be evidenced by at least a two-fold increase, or in other embodiments a four-fold increase, in the uptake of the compound into mammalian cells relative to uptake of the agent by an attached transport moiety lacking the hydrophobic subunits Y'. In some embodiments, uptake is enhanced at least twenty fold or at least forty fold, relative to the unconjugated compound.

A further benefit of the peptide transport moiety is its expected ability to stabilize a duplex between an antisense oligomer and its target nucleic acid sequence. While not wishing to be bound by theory, this ability to stabilize a duplex may result from the electrostatic interaction between the positively charged transport moiety and the negatively charged nucleic acid. In some embodiments, the number of charged subunits in the transporter is less than 14, as noted above, or in other embodiments between 8 and 11, since too high a number of charged subunits may lead to a reduction in sequence specificity.

Exemplary arginine-rich cell-penetrating peptide transporters comprising linkers (B or AhxB) are given below in Table 3:

TABLE 3

Arginine-Rich Cell-Penetrating Peptide Transporters

| Name (Designation) | Sequence | SEQ ID NO.[a] |
|---|---|---|
| rTAT | RRRQRRKKR | 56 |
| Tat | RKKRRQRRR | 57 |
| $R_9F_2$ | RRRRRRRRFF | 58 |
| $R_5F_2R_4$ | RRRRRFFRRRR | 59 |
| $R_4$ | RRRR | 60 |
| $R_5$ | RRRRR | 61 |
| $R_6$ | RRRRRR | 62 |
| $R_7$ | RRRRRRR | 63 |

TABLE 3-continued

Arginine-Rich Cell-Penetrating Peptide Transporters

| Name (Designation) | Sequence | SEQ ID NO.[a] |
|---|---|---|
| $R_8$ | RRRRRRRR | 64 |
| $R_9$ | RRRRRRRRR | 65 |
| $(RAhxR)_4$; (P007) | RAhxRRAhxRRAhxRRAhxR | 66 |
| $(RAhxR)_5$; (CP04057) | RAhxRRAhxRRAhxRRAhxRRAhxR | 67 |
| $(RAhxRRBR)_2$; (CP06062) | RAhxRRBRRAhxRRBR | 68 |
| $(RAR)_4F_2$ | RARRARRARRARFFC | 69 |
| $(RGR)_4F_2$ | RGRRGRRGRRGRFFC | 70 |

[a]Sequences assigned to SEQ ID NOs do not include the linkage portion (e.g., C, G, Ahx, B, AhxB where Ahx and B refer to 6-aminohexanoic acid and beta-alanine, respectively).

C. Properties of the Oligomers

As noted above, the present disclosure is directed to oligomer comprising various modifications which impart desirable properties (e.g., increased antisense activity) to the oligomers. In certain embodiments, the oligomer comprises a backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid. The morpholino ring structures may have the following structure (i):

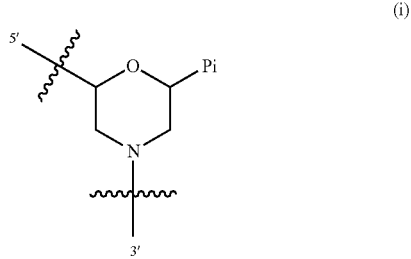

wherein B is, at each occurrence, independently a base-pairing moiety.

Each morpholino ring structure supports a base pairing moiety (Pi), to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine. Analog bases that confer improved binding affinity to the oligomer can also be utilized. Exemplary analogs in this regard include C5-propynyl-modified pyrimidines, 9-(aminoethoxy)phenoxazine (G-clamp) and the like.

As noted above, the oligomer may be modified, in accordance with an aspect of the invention, to include one or more (B) linkages, e.g. up to about 1 per every 2-5 uncharged linkages, typically 3-5 per every 10 uncharged linkages. Certain embodiments also include one or more linkages of type (B). Optimal improvement in antisense activity is seen where up to about half of the backbone linkages are type (B). Some, but not maximum enhancement is typically seen with a small number e.g., 10-20% of (B) linkages.

In one embodiment, the linkage types (A) and (B) are interspersed along the backbone. In some embodiments, the oligomer does not have a strictly alternating pattern of (A) and (B) linkages along its entire length. The oligomers may optionally comprise a 5' and/or 3' modification as described above.

Also considered are oligomers having blocks of (A) linkages and blocks of (B) linkages; for example, a central block of (A) linkages may be flanked by blocks of (B) linkages, or vice versa. In one embodiment, the oligomer has approximately equal-length 5', 3; and center regions, and the percentage of (B) or (A) linkages in the center region is greater than about 50%, o greater than about 70%. Oligomers for use in antisense applications generally range in length from about 10 to about 40 subunits, more preferably about 15 to 25 subunits. For example, an oligomer of the invention having 19-20 subunits, a useful length for an antisense oligomer, may ideally have two to seven, e.g. four to six, or three to five, (B) linkages, and the remainder (A) linkages. An oligomer having 14-15 subunits may ideally have two to five, e.g. 3 or 4, (B) linkages and the remainder (A) linkages.

The morpholino subunits may also be linked by non-phosphorus-based intersubunit linkages, as described further below, where at least one linkage is linkage (B).

Other oligonucleotide analog linkages which are uncharged in their unmodified state but which could also bear a pendant amine substituent can also be used. For example, a 5'nitrogen atom on a morpholino ring could be employed in a sulfamide linkage (or a urea linkage, where phosphorus is replaced with carbon or sulfur, respectively).

In some embodiments for antisense applications, the oligomer may be 100% complementary to the nucleic acid target sequence, or it may include mismatches, e.g., to accommodate variants, as long as a heteroduplex formed between the oligomer and nucleic acid target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability.

Although such an antisense oligomer is not necessarily 100% complementary to the nucleic acid target sequence, it is effective to stably and specifically bind to the target sequence, such that a biological activity of the nucleic acid target, e.g., expression of encoded protein(s), is modulated.

The stability of the duplex formed between an oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol*. Vol. 154 pp. 94-107.

In some embodiments, each antisense oligomer has a binding $T_m$, with respect to a complementary-sequence RNA, of greater than body temperature or in other embodiments greater than 50° C. In other embodiments $T_m$'s are in the range 60-80° C. or greater. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values. For some applications, longer oligomers, for example longer than 20 bases may have certain advantages. For example, in certain embodiments longer oligomers may find particular utility for use in exon skippin or splice modulation.

The targeting sequence bases may be normal DNA bases or analogues thereof, e.g., uracil and inosine that are capable of Watson-Crick base pairing to target-sequence RNA bases.

The oligomers may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

The compounds (e.g., oligomers, intersubunit linkages, terminal groups) may exist in different isomeric forms, for example structural isomers (e.g., tautomers). With regard to stereoisomers, the compounds may have chiral centers and may occur as racemates, enantiomerically enriched mixtures, individual enantiomers, mixture or diastereomers or individual diastereomers. All such isomeric forms are included within the present invention, including mixtures thereof. The compounds may also possess axial chirality which may result in atropisomers. Furthermore, some of the crystalline forms of the compounds may exist as polymorphs, which are included in the present invention. In addition, some of the compounds may also form solvates with water or other organic solvents. Such solvates are similarly included within the scope of this invention.

The oligomers described herein may be used in methods of inhibiting production of a protein or replication of a virus. Accordingly, in one embodiment a nucleic acid encoding such a protein is exposed to an oligomer as disclosed herein. In further embodiments of the foregoing, the antisense oligomer comprises either a 5' or 3' modified terminal group or combinations thereof, as disclosed herein, and the base pairing moieties B form a sequence effective to hybridize to a portion of the nucleic acid at a location effective to inhibit production of the protein. In one embodiment, the location is an ATG start codon region of an mRNA, a splice site of a pre-mRNA, or a viral target sequence as described below.

In one embodiment, the oligomer has a $T_m$ with respect to binding to the target sequence of greater than about 50° C., and it is taken up by mammalian cells or bacterial cells. In another embodiment, the oligomer may be conjugated to a transport moiety, for example an arginine-rich peptide, as described herein to facilitate such uptake. In another embodiment, the terminal modifications described herein can function as a transport moiety to facilitate uptake by mammalian and/or bacterial cells.

The preparation and properties of morpholino oligomers is described in more detail below and in U.S. Pat. No. 5,185,444 and WO/2009/064471, each of which is hereby incorporated by reference in their entirety.

D. Formulation and Administration of the Oligomers

The present disclosure also provides for formulation and delivery of the disclosed oligomer. Accordingly, in one embodiment the present disclosure is directed to a composition comprising an oligomer as disclosed herein and a pharmaceutically acceptable vehicle.

Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

The compounds (e.g., oligomers) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, antisense inhibition is effective in treating infection of a host animal by a virus, by contacting a cell infected with the virus with an antisense agent effective to inhibit the replication of the specific virus. The antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc., and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of disease and/or infection, such as complete blood count (CBC), nucleic acid detection methods, immunodiagnostic tests, viral culture, or detection of heteroduplex.

The efficacy of an in vivo administered antiviral antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

In some embodiments, the oligomer is actively taken up by mammalian cells. In further embodiments, the oligomer may be conjugated to a transport moiety (e.g., transport peptide) as described herein to facilitate such uptake.

E. Preparation of the Oligomers

The morpholino subunits, the modified intersubunit linkages and oligomers comprising the same can be prepared as described in the examples and in U.S. Pat. Nos. 5,185,444 and 7,943,762 which are hereby incorporated by reference in their entirety. The morpholino subunits can be prepared according to the following general Reaction Scheme I.

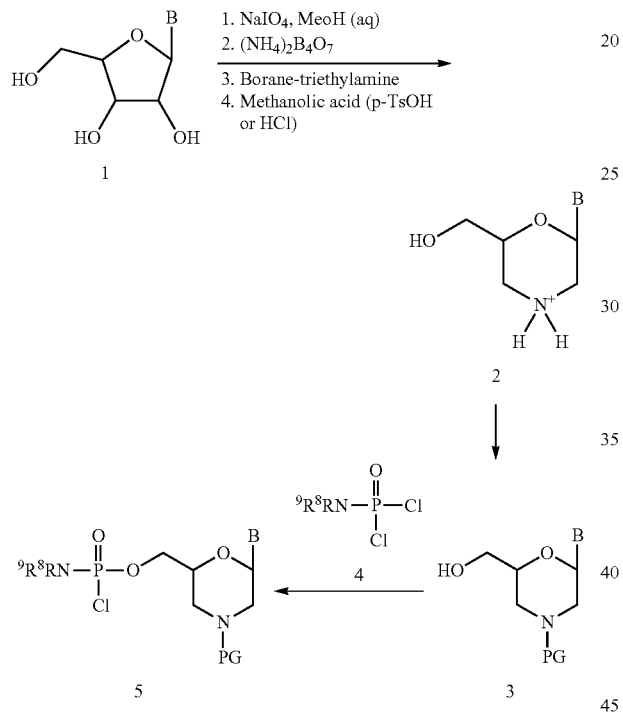

Referring to Reaction Scheme 1, wherein B represents a base pairing moiety and PG represents a protecting group, the morpholino subunits may be prepared from the corresponding ribinucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing poiety may be suitable protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunints having the desired linkage moiety (5). Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762. Although the above scheme depicts preparation of linkages of type (B) (e.g., X is —NR$^8$R$^9$), linkages of type (A) (e.g., X is dimethyl amine) can be prepared in an analogous manner.

Figure 3:
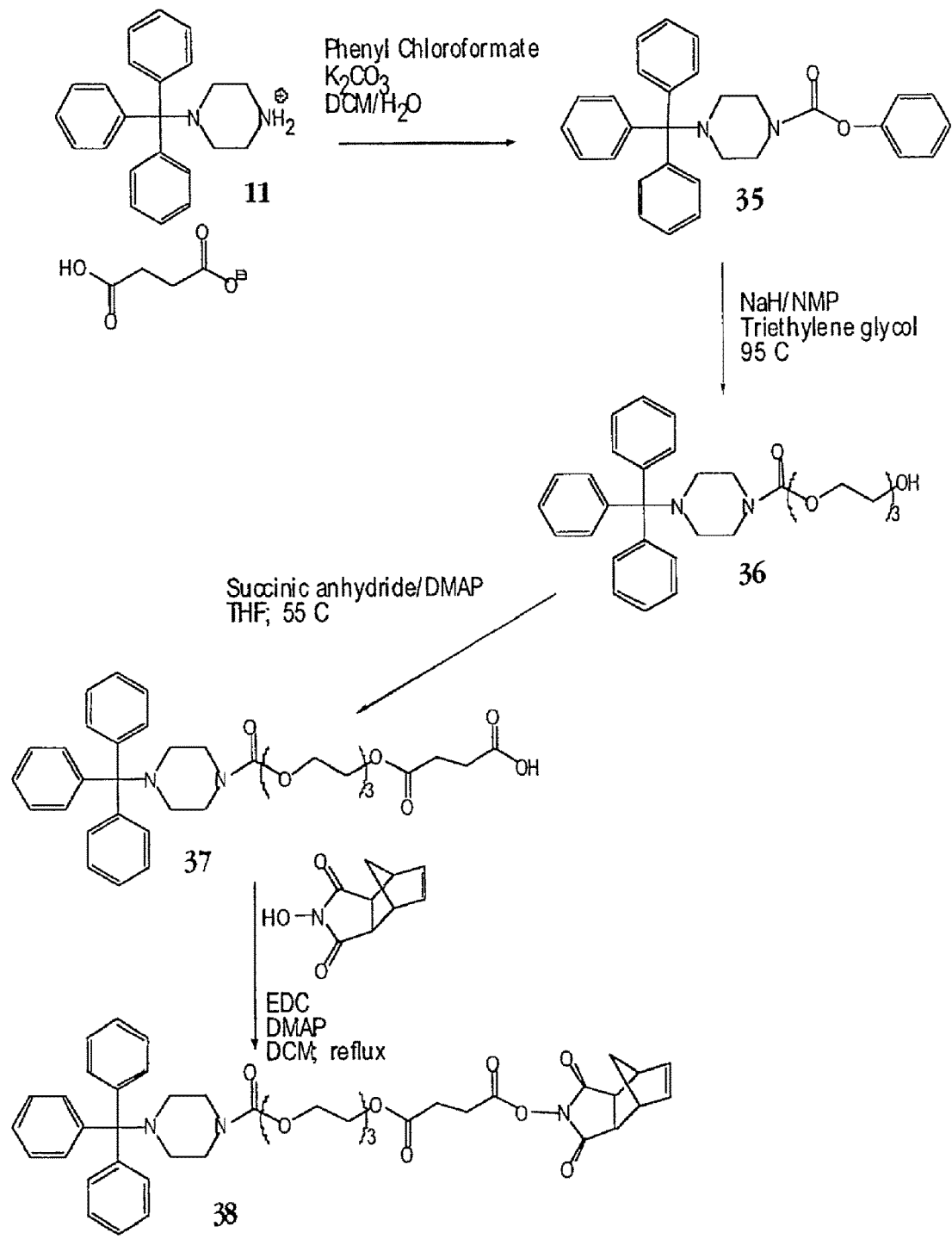
FIG. 3 is a reaction scheme showing preparation of a linker for solid-phase synthesis.
Figure 4:
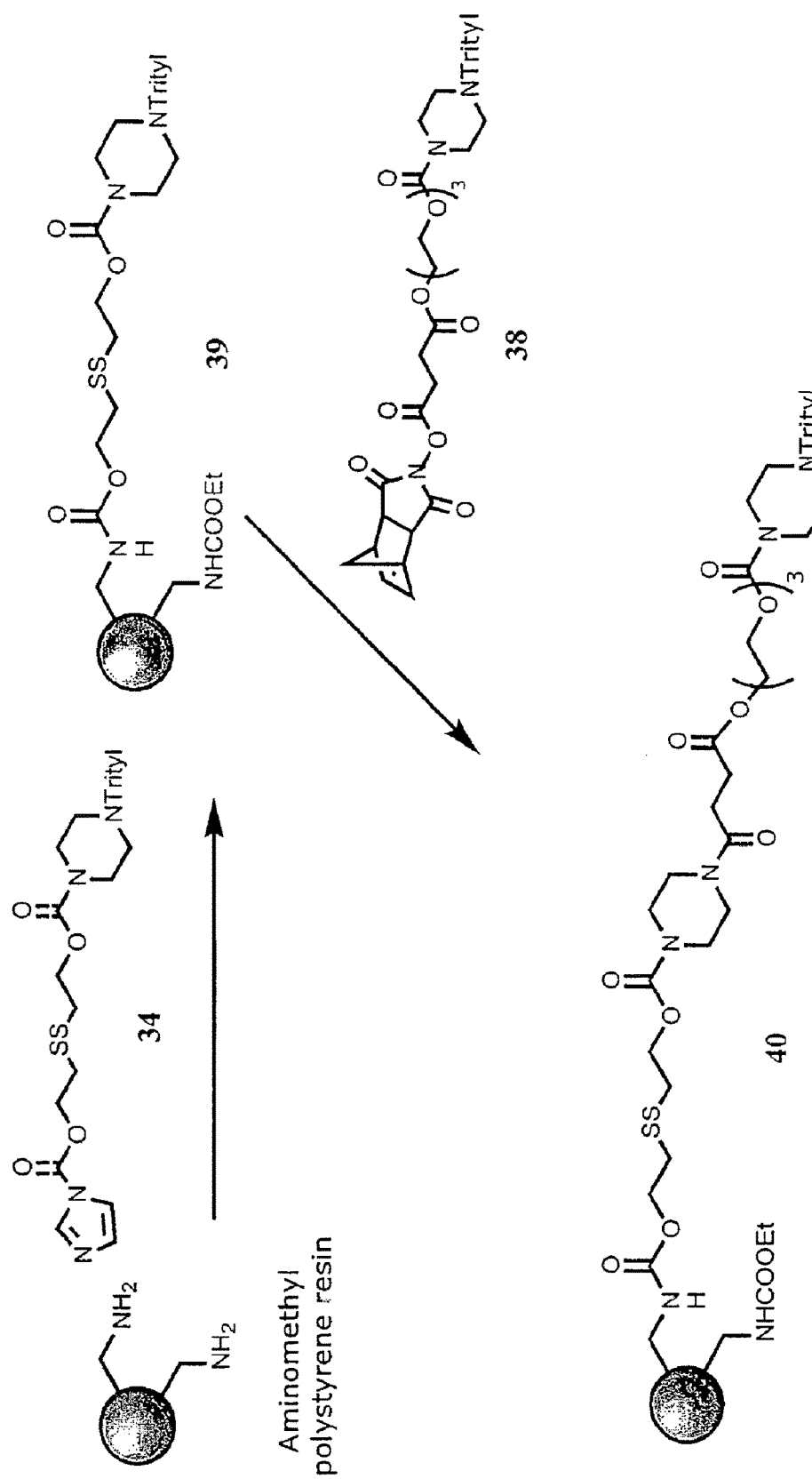
FIG. 4 demonstrates preparation of a solid support for oligomer synthesis.

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising L$^1$ and/or R$^{19}$. An exemplary method is demonstrated in FIGS. 3 and 4. In this manner, the oligo may comprise a 5'-terminal modification after oligomer synthesis is complete and the oligomer is cleaved from the solid support. Once supported, the protecting group of 5 (e.g., trityl) is removed and the free amine is reacted with an activated phosphorous moiety of a second compound of structure 5. This sequence is repeated until the desired length oligo is obtained. The protecting group in the terminal 5' end may either be removed or left on if a 5'-modification is desired. The oligo can be removed from the solid support using any number of methods, or example treatment with a base to cleave the linkage to the solid support.

In one embodiment, the disclosure provides morpholino subunits for preparation of the oligomers, as well as related methods. The morpholino subunits have the following structure (XXXI)

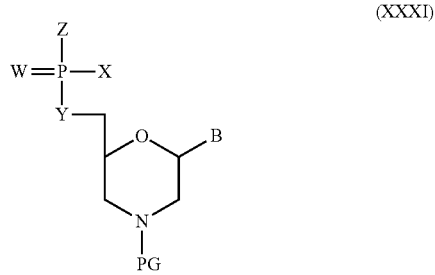

(XXXI)

Wherein W, X and Y are as defined for linkage (B) above, B is a base pairing moiety, Z is a linkage to a solid support or a suitable leaving group and PG is a protecting group, for example $C_7$-$C_{30}$ aralkyl. In some embodiments, PG is trityl, for example methoxytrityl. In other embodiments, the linkage to the solid support comprises L$^2$ and/or R$^{19}$ as defined above. L$^2$ is an optional linker comprising bonds selected from alkyl, hydroxyl, alkoxy, alkylamino, amide, ester, disulfide, carbonyl, carbamate, phosphorodiamidate, phosphoroamidate, phosphorothioate, piperazine and phosphodiester. The length of L$^2$ is not particularly limited. In some embodiments, L$^2$ is less than 60 atoms in length, less than 50 atoms in length or less than 40 atoms length. In some other embodiments, Z is halo, for example chloro.

In still another embodiment, the present disclosure provides a method of preparing any of the disclosed oligomers.

The method comprises use of a compound of structure (XXXI) for preparation of the oligomer.

The preparation of modified morpholino subunits and morpholino oligomers are described in more detail in the Examples. The morpholino oligomers containing any number of modified linkages may be prepared using methods described herein, methods known in the art and/or described by reference herein. Also described in the examples are global modifications of PMO+ morpholino oligomers prepared as previously described (see e.g., PCT publication WO2008036127).

F. Antisense Activity of the Oligomers

The present disclosure also provides a method of inhibiting production of a protein, the method comprising exposing a nucleic acid encoding the protein to an oligomer as disclosed herein. Accordingly, in one embodiment a nucleic acid encoding such a protein is exposed to an antisense oligomer comprising at least one linkage of type (B), or in other embodiments 10% to 50% such modified linkages, as disclosed herein, where the base pairing moieties Pi form a sequence effective to hybridize to a portion of the nucleic acid at a location effective to inhibit production of the protein. The oligomer may target, for example, an ATG start codon region of an mRNA, a splice site of a pre-mRNA, or a viral target sequence as described below. In another embodiment, the method comprises exposing a nucleic acid encoding such a protein to an antisense oligomer comprising at least one terminal modification (e.g., at least one $R^{20}$ moiety).

In another embodiment, the disclosure provides a method of enhancing antisense activity of an oligomer having a sequence of morpholino subunits, joined by intersubunit linkages, supporting base-pairing moieties, the method comprises modifying an oligomer as described herein to contain at least one of the modified terminal groups, at least one intersubunit linkage of type (B) or combinations thereof.

In some embodiments, enhancement of antisense activity may be evidenced by:

(i) a decrease in expression of an encoded protein, relative to that provided by a corresponding unmodified oligomer, when binding of the antisense oligomer to its target sequence is effective to block a translation start codon for the encoded protein, or (ii) an increase in expression of an encoded protein, relative to that provided by a corresponding unmodified oligomer, when binding of the antisense oligomer to its target sequence is effective to block an aberrant splice site in a pre-mRNA which encodes said protein when correctly spliced. Assays suitable for measurement of these effects are described further below. In one embodiment, modification provides this activity in a cell-free translation assay, a splice correction translation assay in cell culture, or a splice correction gain of function animal model system as described herein. In one embodiment, activity is enhanced by a factor of at least two, at least five or at least ten.

Described below are various exemplary applications of the oligomers of the invention including antiviral applications, treatment of neuromuscular diseases, bacterial infections, inflammation and polycystic kidney disease. This description is not meant to limit the invention in any way but serves to exemplify the range of human and animal disease conditions that can be addressed using oligomers comprising the modified intersubunit linkages described herein.

G. In Vitro Activity in Cell Free Assays

Figure 2:
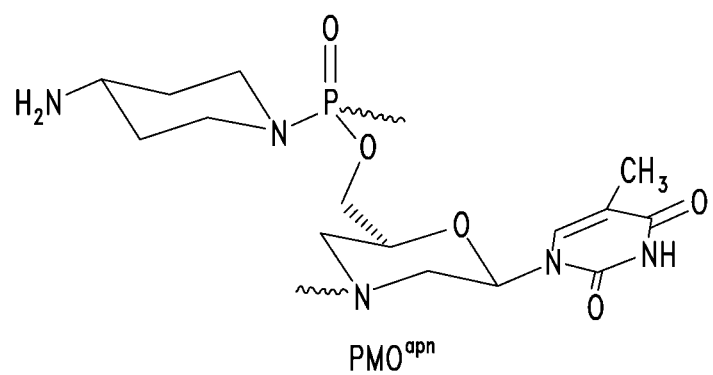
FIG. 2 depicts exemplary intersubunit linkages linked to a morpholino-T moiety.
Figure 2:
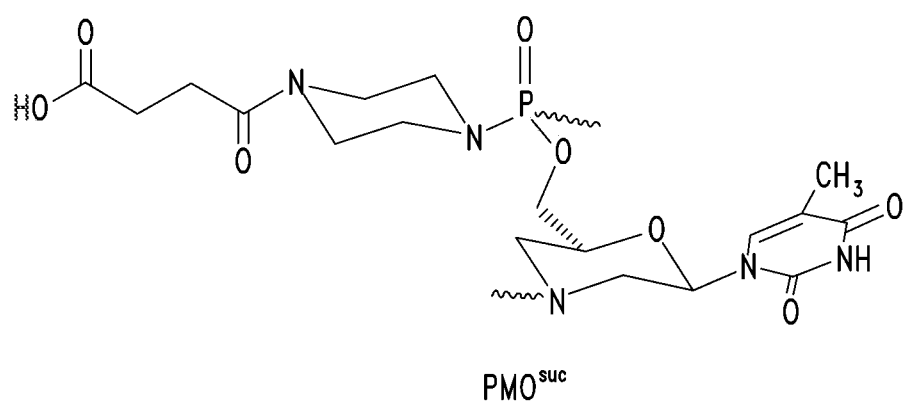

The oligomers with partially modified linkages, such as $PMO^{apn}$ (b10) and $PMO^{suc}$ (b45), have higher affinity for DNA and RNA than do the corresponding neutral compounds, demonstrated by enhanced antisense activity in vitro and in vivo. The oligomers of the invention were shown to provide superior antisense activity compared to fully unmodified oligomers when directed to a variety of different targets. In a first series of experiments, various unmodified, modified and peptide-conjugated PPMO targeting exon 23 of the MDX mouse dystrophin gene were prepared, as described in Materials and Methods and Example 27. The sequences are shown as in Example 27, with the previously described (1-piperazino) phosphinylideneoxy linkage (as shown in FIG. 1B) at each position indicated with a "+" for SEQ ID NOs: 2-5; the 4-aminopiperidinyl linkage (structure (b10); FIG. 2) indicated with an "$^{a}$" for SEQ ID NO: 5 or; the 4-succinamidopiperazinyl linkage (structure (b45); FIG. 2) indicated with an "$^{s}$". As described in Example 27, PMO oligomers containing an exemplary linkage (e.g., $PMO^{apn}$) of the invention were more active compared to previously described PMO+ compounds.

1. Targeting Stem-Loop Secondary Structure of ssRNA Viruses

One class of an exemplary antisense antiviral compound is a morpholino oligomer as described herein, for example and oligomer comprising at least one linkage of type (B) and/or at least one terminal modification (e.g., at least one $R^{20}$) or combinations thereof, having a sequence of 12-40 subunits and a targeting sequence that is complementary to a region associated with stem-loop secondary structure within the 5'-terminal end 40 bases of the positive-sense RNA strand of the targeted virus. (See, e.g., PCT Pubn. No. WO/2006/033933 or U.S. Appn. Pubn. Nos. 20060269911 and 20050096291, which are incorporated herein by reference.)

The method comprises first identifying as a viral target sequence, a region within the 5'-terminal 40 bases of the positive strand of the infecting virus whose sequence is capable of forming internal stem-loop secondary structure. There is then constructed, by stepwise solid-phase synthesis, an oligomer comprising at least one linkage of type (B) and/or at least one terminal modification (e.g., at least one $R^{20}$) or combinations thereof, and in other embodiments containing 20% to 50% such modified linkages, and having a targeting sequence of at least 12 subunits that is complementary to the virus-genome region capable of forming internal duplex structure, where the oligomer is able to form with the viral target sequence, a heteroduplex structure composed of the positive sense strand of the virus and the oligonucleotide compound, and characterized by a Tm of dissociation of at least 45° C. and disruption of such stem-loop structure.

The target sequence may be identified by analyzing the 5'-terminal sequences, e.g., the 5'-terminal 40 bases, by a computer program capable of performing secondary structure predictions based on a search for the minimal free energy state of the input RNA sequence.

In a related aspect, the oligomers can be used in methods of inhibiting in a mammalian host cell, replication of an infecting RNA virus having a single-stranded, positive-sense genome and selected from one of the Flaviviridae, Picornoviridae, Caliciviridae, Togaviridae, Arteriviridae, Coronaviridae, Astroviridae or Hepeviridae families. The method includes administering to the infected host cells, a virus-inhibitory amount of an oligomer as described herein, having a targeting sequence of at least 12 subunits that is complementary to a region within the 5'-terminal 40 bases of the positive-strand viral genome that is capable of forming internal stem-loop secondary structure. The compound is effective, when administered to the host cells, to form a heteroduplex structure (i) composed of the positive sense strand of the virus and the oligonucleotide compound, and (ii) characterized by a Tm of dissociation of at least 45° C. and disruption of such stem-loop secondary structure. The compound may be administered to a mammalian subject infected with the virus, or at risk of infection with the virus.

Exemplary targeting sequences that target the terminal stem loop structures of the dengue and Japanese encephalitis viruses are listed below as SEQ ID NOs: 1 and 2, respectively.

Additional exemplary targeting sequences that target the terminal stem loop structures of ssRNA viruses can also be found in U.S. application Ser. No. 11/801,885 and PCT publication WO/2008/036127 which are incorporated herein by reference.

2. Targeting the First Open Reading Frame of ssRNA Viruses

A second class of exemplary antisense antiviral compounds for use in inhibition of growth of viruses of the picornavirus, calicivirus, togavirus, coronavirus, and flavivirus families having a single-stranded, positive sense genome of less than 12 kb and a first open reading frame that encodes a polyprotein containing multiple functional proteins. In particular embodiments, the virus is an RNA virus from the coronavirus family or a West Nile, Yellow Fever or Dengue virus from the flavivirus family. The inhibiting compounds comprise antisense oligomers described herein, for example oligomers comprising at least one linkage of type (B) and/or at least one terminal modification (e.g., at least one $R^{20}$) or combinations thereof, having a targeting base sequence that is substantially complementary to a viral target sequence which spans the AUG start site of the first open reading frame of the viral genome. In one embodiment of the method, the oligomer is administered to a mammalian subject infected with the virus. See, e.g., PCT Pubn. No. WO/2005/007805 and US Appn. Pubn. No. 2003224353, which are incorporated herein by reference.

The preferred target sequence is a region that spans the AUG start site of the first open reading frame (ORF1) of the viral genome. The first ORF generally encodes a polyprotein containing non-structural proteins such as polymerases, helicases and proteases. By "spans the AUG start site" is meant that the target sequence includes at least three bases on one side of the AUG start site and at least two bases on the other (a total of at least 8 bases). Preferably, it includes at least four bases on each side of the start site (a total of at least 11 bases).

More generally, preferred target sites include targets that are conserved between a variety of viral isolates. Other favored sites include the IRES (internal ribosome entry site), transactivation protein binding sites, and sites of initiation of replication. Complex and large viral genomes, which may provide multiple redundant genes, may be efficiently targeted by targeting host cellular genes coding for viral entry and host response to viral presence.

A variety of viral-genome sequences are available from well known sources, such as the NCBI Genbank databases. The AUG start site of ORF1 may also be identified in the gene database or reference relied upon, or it may be found by scanning the sequence for an AUG codon in the region of the expected ORF1 start site.

The general genomic organization of each of the four virus families is given below, followed by exemplary target sequences obtained for selected members (genera, species or strains) within each family.

3. Targeting Influenza Virus

A third class of exemplary antisense antiviral compounds are used in inhibition of growth of viruses of the Orthomyxoviridae family and in the treatment of a viral infection. In one embodiment, the host cell is contacted with an oligomer as described herein, for example an oligomer comprising at least one linkage of type (B) and/or at least one terminal modification (e.g., at least one $R^{20}$) or combinations thereof, or in other embodiments comprising 20% to 50% such modified linkages, and comprising a base sequence effective to hybridize to a target region selected from the following: 1) the 5' or 3' terminal 25 bases of the negative sense viral RNA segments; 2) the terminal 25 bases of the 5' or 3' terminus of the positive sense cRNA; 3) 45 bases surrounding the AUG start codons of influenza viral mRNAs and; 4) 50 bases surrounding the splice donor or acceptor sites of influenza mRNAs subject to alternative splicing. (See, e.g., PCT Pubn. No. WO/2006/047683; U.S. Appn. Pubn. No. 20070004661; and PCT Appn. Num. 2010/056613 and U.S. application Ser. No. 12/945,081, which are incorporated herein by reference.)

Experiments in support of the invention and designed to target the M1/M2 segment of influenza A virus (H1N1 strain PR8) using PMO with modified linkages of the invention were performed using oligomers based on SEQ ID NO:3, listed below in Table 4 and described in Example 29.

TABLE 4

Influenza targeting sequences that incorporate modified intersubunit linkages or terminal groups

| | | |
|---|---|---|
| NG-10-0038 | PMOhex | CGG T$^h$TA GAA GAC $^h$TCA TC$^h$T TT |
| NG-10-0039 | PMOhex | CGG T$^h$TA GAA GAC $^h$TCA $^h$TCT $^h$TT |
| NG-10-0096 | PMOapn | CGG T$^a$TA GAA GAC $^a$TCA TC$^a$T TT |
| NG-10-0097 | PMOapn | CGG $^a$T$^a$TA GAA GAC $^a$TCA $^a$TC$^a$T TT |
| NG-10-0099 | PMOpyr | CGG $^p$T$^p$TA GAA GAC $^p$TCA $^p$TC$^p$T TT |
| NG-10-0107 | PMOthiol | CGG T$^{SH}$TA GAA GAC $^{SH}$TCA T$^{SH}$HT TT |
| NG-10-0108 | PMOsucc | CGG T$^s$TA GAA GAC $^s$TCA TC$^s$T TT |
| NG-10-0111 | PMOguan | CGG T$^g$TA GAA GAC $^g$TCA TC$^g$T TT |
| NG-10-0141 | PMOpyr | CGG T$^p$TA GAA GAC $^p$TCA $^p$TCT TT |
| NG-10-0142 | PMOpyr | CGG TTA GAA GAC $^p$T CA PTC$^p$T TT |

TABLE 4-continued

Influenza targeting sequences that incorporate modified intersubunit linkages or terminal groups

| ID | Name | Sequence |
|---|---|---|
| NG-10-0158 | PMOglutaric | CGG T$^{glu}$TA GAA GAC $^{glu}$TCA TC$^{glu}$T TT |
| NG-10-0159 | PMOcyclo-glut | CGG T$^{cpglu}$TA GAA GAC $^{cpglu}$TCA TC$^{cpglu}$T TT |
| NG-10-0160 | PMOcholic acid | CGG T$^{ca}$TA GAA GAC $^{ca}$TCA TC$^{ca}$T TT |
| NG-10-0161 | PMOdeoxyCA | CGG T$^{dca}$TA GAA GAC $^{dca}$TCA TC$^{dca}$T TT |
| NG-10-0180 | PMOapn | TT$^{a}$T CGA CA$^{a}$T CGG T$^{a}$TA GAA GAC $^{a}$TCA T |
| NG-10-0174 | PMOm | CGG T$^{m}$TA GAA GAC $^{m}$TCA TC$^{m}$T TT |
| NG-10-0222 | PMO MeT | CGG T$^{Me}$TA GAA GAC +TCA TC+T TT |
| NG-10-0223 | PMO FarnT | CGG T$^{Farn}$TA GAA GAC +TCA TC+T TT |
| NG-10-0538 | PMOapn-trityl | CGG T$^{a}$TA GAA GAC $^{a}$TCA TC$^{a}$T TT |
| NG-10-0539 | PMOapn-trityl | CGG T$^{p}$TA GAA GAC $^{p}$TCA TC$^{p}$T TT |
| NG-10-0015 | PMO | CGG TTA GAA GAC TCA TCT TT |
| NG-11-0170 | PMOplus | CGG +TTA GAA GAC +TCA TC+T TT |
| NG-11-0145 | PMOplus-benzhydryl | CGG T+TA GAA GAC +TCA TC+T TT** |
| NG-11-0148 | PMOiso pro pylPip | CGG TiprpipTA GAA GAC iprpipTCA TCiprpipT TT |
| NG-11-0173 | PMOpyr | CGG pTTA GAA GAC pTCA TCpT TT |
| NG-11-0291 | Trimethyl Gly | CGG T*+TA GAA GAC *+TCA TC*+T TT |

**3'-benzhydryl; *+ linkages are trimethyl glycine acylated at the PMOplus linkages; PMOm represents T bases with a methyl group on the 3-nitrogen position.

The compounds are particularly useful in the treatment of influenza virus infection in a mammal. The oligomer may be administered to a mammalian subject infected with the influenza virus, or at risk of infection with the influenza virus.

4. Targeting Viruses of the Picornaviridae Family

A fourth class of exemplary antisense antiviral compounds are used in inhibition of growth of viruses of the Picomaviridae family and in the treatment of a viral infection. The compounds are particularly useful in the treatment of Enterovirus and/or Rhinovirus infection in a mammal. In this embodiment, the antisense antiviral compounds comprise morpholino oligomers, for example morpholino oligomers comprising at least one linkage of type (B) and/or at least one terminal modification (e.g., at least one R$^{20}$) or combinations thereof, and having a sequence of 12-40 subunits, including at least 12 subunits having a targeting sequence that is complementary to a region associated with viral RNA sequences within one of two 32 conserved nucleotide regions of the viral 5' untranslated region. (See, e.g., PCT Pubn. Nos. WO/2007/030576 and WO/2007/030691 or copending and co-owned U.S. application Ser. Nos. 11/518,058 and 11/517,757, which are incorporated herein by reference.) An exemplary targeting sequence is listed below as SEQ NO: 6.

5. Targeting Viruses of the Flavivirus Family

A fifth class of exemplary antisense antiviral compounds are used in inhibition of replication of a flavivirus in animal cells. An exemplary antisense oligomer of this class is a morpholino oligomer comprising at least one linkage of type (B) and/or at least one terminal modification (e.g., at least one R$^{20}$) or combinations thereof, between 8-40 nucleotide bases in length and having a sequence of at least 8 bases complementary to a region of the virus' positive strand RNA genome that includes at least a portion of the 5'-cyclization sequence (5'-CS) or 3'-CS sequences of the positive strand flaviviral RNA. A highly preferred target is the 3'-CS and an exemplary targeting sequence for dengue virus is listed below as SEQ ID NO: 7. (See, e.g., PCT Pubn. No. (WO/2005/030800) or copending and co-owned U.S. application Ser. No. 10/913,996, which are incorporated herein by reference.)

6. Targeting Viruses of the Nidovirus Family

A sixth class of exemplary antisense antiviral compounds are used in inhibition of replication of a nidovirus in virus-infected animal cells. An exemplary antisense oligomer of this class is a morpholino oligomer comprising at least one linkage of type (B) and/or at least one terminal modification (e.g., at least one R$^{20}$) or combinations thereof, as described in the present disclosure, and containing between 8-25 nucleotide bases, and has a sequence capable of disrupting base pairing between the transcriptional regulatory sequences (TRS) in the 5' leader region of the positive-strand viral genome and negative-strand 3' subgenomic region (See, e.g., PCT Pubn. No. WO/2005/065268 or U.S. Appn. Pubn. No. 20070037763, which are incorporated herein by reference.)

7. Targeting of Filoviruses

In another embodiment, one or more oligomers as described herein can be used in a method of in inhibiting replication within a host cell of an Ebola virus or Marburg virus, by contacting the cell with an oligomer as described herein, for example and oligomer comprising at least one linkage of type (B) and/or at least one terminal modification (e.g., at least one R$^{20}$) or combinations thereof, or in other embodiments 20% to 50% such modified linkages, and having a targeting base sequence that is complementary to a target sequence composed of at least 12 contiguous bases within an AUG start-site region of a positive-strand mRNA, as described further below.

The filovirus viral genome is approximately 19,000 bases of single-stranded RNA that is unsegmented and in the antisense orientation. The genome encodes 7 proteins from monocistronic mRNAs complementary to the vRNA.

Target sequences are positive-strand (sense) RNA sequences that span or are just downstream (within 25 bases) or upstream (within 100 bases) of the AUG start codon of selected Ebola virus proteins or the 3' terminal 30 bases of the minus-strand viral RNA. Preferred protein targets are the viral polymerase subunits VP35 and VP24, although L, nucleoproteins NP and VP30, are also contemplated. Among these early proteins are favored, e.g., VP35 is favored over the later expressed L polymerase.

In another embodiment, one or more oligomers as described herein can be used in a method of in inhibiting replication within a host cell of an Ebola virus or Marburg virus, by contacting the cell with an oligomer as described herein, comprising at least one modified intersubunit linkage, or in other embodiments 20% to 50% such modified linkages, and having a targeting base sequence that is complementary to a target sequence composed of at least 12 contiguous bases within an AUG start-site region of a positive-strand mRNA of the Filovirus mRNA sequences. (See, e.g., PCT Pubn. No. WO/2006/050414 or U.S. Pat. Nos. 7,524,829 and 7,507,196, and continuation applications with U.S. application Ser. Nos. 12/402,455; 12/402,461; 12/402,464; and 12/853,180 which are incorporated herein by reference.)

8. Targeting of Arenaviruses

In another embodiment, an oligomer as described herein can be used in a method for inhibiting viral infection in mammalian cells by a species in the Arenaviridae family. In one aspect, the oligomers can be used in treating a mammalian subject infected with the virus. (See, e.g., PCT Pubn. No. WO/2007/103529 or U.S. Pat. No. 7,582,615, which are incorporated herein by reference.)

Table 5 is an exemplary list of targeted viruses targeted by oligomers of the invention as organized by their Old World or New World Arenavirus classification.

TABLE 5

Targeted Arenaviruses

| Family | Genus | Virus |
| --- | --- | --- |
| Arenaviridae | *Arenavirus* | Old World Arenaviruses |
| | | Lassa virus (LASV) |
| | | Lymphocytic choriomeningitis virus (LCMV) |
| | | Mopeia virus (MOPV) |
| | | New World Arenaviruses |
| | | Guanarito virus (GTOV) |
| | | Junin virus (JUNV) |
| | | Machupo virus (MACV) |
| | | Pichinide virus (PICV) |
| | | Pirital virus (PIRV) |
| | | Sabiá virus (SABV) |
| | | Tacaribe virus (TCRV) |
| | | Whitewater Arroyo virus (WWAV) |

The genome of Arenaviruses consists of two single-stranded RNA segments designated S (small) and L (large). In virions, the molar ratio of S- to L-segment RNAs is roughly 2:1. The complete S-segment RNA sequence has been determined for several arenaviruses and ranges from 3,366 to 3,535 nucleotides. The complete L-segment RNA sequence has also been determined for several arenaviruses and ranges from 7,102 to 7,279 nucleotides. The 3' terminal sequences of the S and L RNA segments are identical at 17 of the last 19 nucleotides. These terminal sequences are conserved among all known arenaviruses. The 5'-terminal 19 or 20 nucleotides at the beginning of each genomic RNA are imperfectly complementary with each corresponding 3' end. Because of this complementarity, the 3' and 5' termini are thought to base-pair and form panhandle structures.

Replication of the infecting virion or viral RNA (vRNA) to form an antigenomic, viral-complementary RNA (vcRNA) strand occurs in the infected cell. Both the vRNA and vcRNA encode complementary mRNAs; accordingly, Arenaviruses are classified as ambisense RNA viruses, rather than negative- or positive-sense RNA viruses. The ambisense orientation of viral genes are on both the L- and S-segments. The NP and polymerase genes reside at the 3' end of the S and L vRNA segments, respectively, and are encoded in the conventional negative sense (i.e., they are expressed through transcription of vRNA or genome-complementary mRNAs). The genes located at the 5' end of the S and L vRNA segments, GPC and Z, respectively, are encoded in mRNA sense but there is no evidence that they are translated directly from genomic vRNA. These genes are expressed instead through transcription of genomic-sense mRNAs from antigenomes (i.e., the vcRNA), full-length complementary copies of genomic vRNAs that function as replicative intermediates.

An exemplary targeting sequence for the arenavirus family of viruses is listed below as SEQ ID NO: 8.

9. Targeting of Respiratory Syncytial Virus

Respiratory syncytial virus (RSV) is the single most important respiratory pathogen in young children. RSV-caused lower respiratory conditions, such as bronchiolitis and pneumonia, often require hospitalization in children less than one-year-old. Children with cardiopulmonary diseases and those born prematurely are especially prone to experience severe disorders from this infection. RSV infection is also an important illness in elderly and high-risk adults, and it is the second-most commonly identified cause of viral pneumonia in older persons (Falsey, Hennessey et al. 2005). The World Health Organization estimates that RSV is responsible for 64 million clinical infections and 160 thousand deaths annually worldwide. No vaccines are currently available for the prevention of RSV infection. Although many major advances in our understanding of RSV biology, epidemiology, pathophysiology, and host-immune-response have occurred over the past few decades, there continues to be considerable controversy regarding the optimum management of infants and children with RSV infection. Ribavirin is the only licensed antiviral drug for treating RSV infection, but its use is limited to high-risk or severely-ill infants. The utility of Ribavirin has been limited by its cost, variable efficacy, and tendency to generate resistant viruses (Marquardt 1995; Prince 2001). The current need for additional effective anti-RSV agents is well-acknowledged.

It is known that peptide conjugated PMO (PPMO) can be effective in inhibiting RSV both in tissue culture and in an in vivo animal model system (Lai, Stein et al. 2008). Two antisense PPMOs, designed to target the sequence that includes the 5'-terminal region and translation start-site region of RSV L mRNA, were tested for anti-RSV activity in cultures of two human airway cell lines. One of them, (RSV-AUG-2; SEQ ID NO 10), reduced viral titers by >2.0 $\log_{10}$. Intranasal (i.n.) treatment of BALB/c mice with RSV-AUG-2 PPMO before the RSV inoculation produced a reduction in viral titer of 1.2 $\log_{10}$ in lung tissue at day 5 postinfection (p.i.), and attenuated pulmonary inflammation at day 7 postinfection. These data showed that RSV-AUG-2 provided potent anti-RSV activity worthy of further investigation as a candidate for potential therapeutic application (Lai, Stein et al. 2008). Despite the success with RSV-AUG-2 PPMO as described above, it is desirable to avoid incorporating peptide conjugation in an antisense anti-RSV therapeutic due to toxicity concerns and cost of goods considerations. Therefore, in another embodiment of the present invention, one or more oligomers as described herein can be used in a method of inhibiting replication within a host cell of RSV, by contacting the cell with an oligomer as described herein, for example an oligomer comprising at least one linkage of type (B) and/or at least one terminal modification (e.g., at least one $R^{20}$) or combinations thereof, or in other embodiments 10% to 50% such modified linkages, and having a targeting base sequence that is complementary to a target sequence composed of at least 12 contiguous bases within an AUG start-site region of anmRNA from RSV, as described further below.

The L gene of RSV codes for a critical component of the viral RNA dependent RNA polymerase complex. Antisense PPMO designed against the sequence spanning the AUG translation start-site codon of the RSV L gene mRNA in the form of RSV-AUG-2 PPMO is complementary to sequence from the 'gene-start' sequence (GS) present at the 5' terminus of the L mRNA to 13 nt into the coding sequence. A preferred L gene targeting sequence is therefore complementary to any 12 contiguous bases from the 5' end of the L gene mRNA extending 40 bases in the 3' direction or 22 bases into the L gene coding sequence as shown below in Table 3 as SEQ ID NO: 9. Exemplary RSV L gene targeting sequences are listed below in Table 3 as SEQ ID NOs: 10-14. Any of the intersubunit modifications of the invention described herein can be incorporated in the oligomers to provide increased antisense activity, improved intracellular delivery and/or tissue specificity for improved therapeutic activity. Exemplary oligomers containing intersubunit linkages of the invention are listed below in Table 6.

10. Neuromuscular Diseases

In another embodiment, a therapeutic oligomer is provided for use in treating a disease condition associated with a neuromuscular disease in a mammalian subject. Exemplary intersubunit oligomer modifications shown to enhance transport into muscle tissue include those having intersubunit linkages of structure b6, b10, b51 and b54. Antisense oligomers that incorporate such linkages into the M23D antisense oligomer (SEQ ID NO: 16) are tested for activity in the MDX mouse model for Duchene Muscular Dystrophy (DMD) as described in the Examples. Exemplary oligomers that incorporate the linkages used in some embodiments are listed below in Table 7. In some embodiments, the therapeutic compound may be selected from the group consisting of:

(a) an antisense oligomer targeted against human myostatin, having a base sequence complementary to at least 12 contiguous bases in a target region of the human myostatin mRNA identified by SEQ ID NO: 18, for treating a muscle wasting condition, as described previously (See, e.g., U.S. patent application Ser. No. 12/493,140, which is incorporated herein by reference; and PCT publication WO2006/086667). Exemplary murine targeting sequences are listed as SEQ ID NOs: 19-20.

(b) an antisense oligomer capable of producing exon skipping in the DMD protein (dystrophin), such as a PMO having a sequence selected from SEQ ID NOs: 22 to 35, to restore partial activity of the dystrophin protein, for treating DMD, as described previously (See, e.g., PCT Pubn. Nos. WO/2010/048586 and WO/2006/000057 or U.S. Patent Publication No. U.S. Ser. No. 09/061,960 all of which are incorporated herein by reference).

Several other neuromuscular diseases can be treated using the modified linkages and terminal groups of the present invention. Exemplary compounds for treating spinal muscle atrophy (SMA) and myotonic dystrophy (DM) are discussed below.

SMA is an autosomal recessive disease caused by chronic loss of alpha-motor neurons in the spinal cord and can affect both children and adults. Reduced expression of survival motor neuron (SMN) is responsible for the disease (Hua, Sahashi et al. 2010). Mutations that cause SMA are located in the SMN1 gene but a paralogous gene, SMN2, can allow viability by compensating for loss of SMN1 if expressed from an alternative splice form lacking exon 7 (delta7 SMN2). Antisense compounds targeted to inton 6, exon 7

TABLE 6

RSV target and targeting sequences

| Name | Sequence (5' to 3') | SEQ ID NO |
|---|---|---|
| L target | GGGACAAAATGGATCCCATTATTAATGGAAATTCTGCTAA | 9 |
| RSV-AUG-2 | TAATGGGATCCATTTTGTCCC | 10 |
| RSV-AUG3 | AATAATGGGATCCATTTTGTCCC | 11 |
| RSV-AUG4 | CATTAATAATGGGATCCATTTTGTCCC | 12 |
| RSV-AUG5 | GAATTTCCATTAATAATGGGATCCATTTTG | 13 |
| RSV-AUG6 | CAGAATTTCCATTAATAATGGGATCCATT | 14 |
| RSV-AUG3apn* | AATAA$^{apn}$TGGGA$^{apn}$TCCA$^{apn}$TT$^{apn}$TTG$^{apn}$TCCC | 11 |
| RSV-AUG3guan | AATAA$^{guan}$TGGGA$^{guan}$TCCA$^{guan}$TT$^{guan}$TTG$^{guan}$TCCC | 11 | and intron 7 have all been shown to induce exon 7 inclusion to varying degrees. Antisense compounds targeted to intron 7 are preferred (see e.g., PCT Publication Nos. WO/2010/148249, WO/2010/120820, WO/2007/002390 and U.S. Pat. No. 7,838,657). Exemplary antisense sequences that target the SMN2 pre-mRNA and induce improved exon 7 inclusion are listed below as SEQ ID NOs: 36-38. It is contemplated that selected modifications of these oligomer sequences using the modified linkages and terminal groups described herein would have improved properties compared to those known in the art. Furthermore, it is contemplated that any oligomer targeted to intron 7 of the SMN2 gene and incorporating the features of the present invention has the potential to induce exon 7 inclusion and provide a therapeutic benefit to SMA patients. Myotonic Dystrophy type 1 (DM1) and type 2 (DM2) are dominantly inherited disorders caused by expression of a toxic RNA leading to neuromuscular degeneration. DM1 and DM2 are associated with long polyCUG and polyCCUG repeats in the 3'-UTR and intron 1 regions of the transcript dystrophia myotonica protein kinase (DMPK) and zinc finger protein 9 (ZNF9), respectively (see e.g., WO2008/036406). While normal individuals have as many as 30 CTG repeats, DM1 patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP). Several RNA-BP have been implicated in the disease, including muscleblind-like (MBNL) proteins and CUG-binding protein (CUGBP). MBNL proteins are homologous to *Drosophila* muscleblind (Mbl) proteins necessary for photoreceptor and muscle differentiation. MBNL and CUGBP have been identified as antagonistic splicing regulators of transcripts affected in DM1 such as cardiac troponin T (cTNT), insulin receptor (IR) and muscle-specific chloride channel (ClC-1).

It is known in the art that antisense oligonucleotides targeted to the expanded repeats of the DMPK gene can displace RNA-BP sequestration and reverse myotonia symptoms in an animal model of DM1 (WO2008/036406). It is contemplated that oligomers incorporating features of the present invention would provide improved activity and therapeutic potential for DM1 and DM2 patients. Exemplary sequences targeted to the polyCUG and polyCCUG repeats described above are listed below as SEQ ID NOs: 39-55 and further described in U.S. application Ser. No. 13/101,942 which is incorporated herein in its entirety.

Additional embodiments of the present invention for treating neuralmuscular disorders are anticipated and include oligomers designed to treat other DNA repeat instability genetic disorders. These diseases include Huntington's disease, spino-cerebellar ataxia, X-linked spinal and bulbar muscular atrophy and spinocerebellar ataxia type 10 (SCA10) as described in WO2008/018795.

Experiments performed in support of the invention using the MDX mouse, a murine model for DMD, are described in Example 27.

TABLE 7

M23D sequences (SEQ ID NO: 15) that incorporate modified intersubunit linkages and/or 3' and/or 5' terminal groups

| NG | PMO-X Modification | 5' | Sequence | 3' |
|---|---|---|---|---|
| NG-10-0383 | PMO | EG3 | GGC CAA ACC TCG GCT TAC CTG AAA T | triphenylacetyl |
| NG-10-0325 | triphenylphos | OH | GGC CAA ACC FCG GCF TAC CFG AAA T | triphenylphos |
| NG-10-0272 | PMO-farnesyl | OH | GGC CAA ACC TCG GCT TAC CTG AAA T | farnesyl |
| NG-10-0102 | PMO | OH | GGC CAA ACC TCG GCT TAC CTG AAA T | trityl |
| NG-10-0330 | trimethoxybenzoyl | EG3 | GGC CAA ACC TCG GCT TAC CTG AAA T | trimethoxybenzoyl |
| NG-10-0056 | PMOplus 5'-pol | EG3 | GGC C$^+$A$^+$A $^+$ACC TCG GCT TAC CTG AAA T | H |
| NG-07-0064 | PMO-3'-trityl | H-Pip | GGC CAA ACC TCG GCT TAC CTG AAA T | trityl |
| NG-10-0382 | PMO | EG3 | GGC CAA ACC TCG GCT TAC CTG AAA T | triphenylpropionyl |
| NG-10-0278 | PMOpyr | EG3 | GGC CAA ACC pTCG GCpT pTAC CpTG AAA pT | H |
| NG-10-0210 | PMOapn | EG3 | GGC C$^a$A$^a$ $^a$ACC TCG GCT TAC CTG AAA T | H |
| NG-10-0098 | PMOpyr | EG3 | GGC CAA ACC $^p$TCG GC$^p$T TAC C$^p$TG AAA T | H |

TABLE 7-continued

M23D sequences (SEQ ID NO: 15) that incorporate modified intersubunit linkages and/or 3' and/or 5' terminal groups

| NG | PMO-X Modification | 5' | Sequence | 3' |
|---|---|---|---|---|
| NG-10-0070 | PMOapn | EG3 | GGC CAA ACC $^a$TCG GC$^a$T TAC C$^a$TG AAA $^a$T | H |
| NG-10-0095 | PMOapn | EG3 | GGC CAA ACC $^a$TCG GC$^a$T $^a$TAC C$^a$T G AAA $^a$T | H |
| NG-10-0317 | PMO | EG3 | GGC CAA ACC TCG GCT TAC CTG AAA T | farnesyl |
| NG-10-0477 | PMO triMe Gly | EG3 | GGC CAA ACC FCG GCF TAC CFG AAA F | trimethyl Glycine |
| NG-10-0133 | PMOapn | OH | GGC C$^a$AA $^a$ACC $^a$TCG GC$^a$T $^a$TAC C$^a$TG AAA $^a$T | H |
| NG-10-0387 | PMO | EG3 | GGC CAA ACC TCG GCT TAC CTG AAA T | 2-OH, diphenylacet |
| NG-10-0104 | PMOguan | EG3 | GGC CAA ACC $^g$TCG GC$^g$T TAC C$^g$T G AAA T | $\Delta^g$ |
| NG-10-0420 | PMOplus methyl | EG3 | GGC CAA ACC $^{m+}$TCG GC$^{m+}$T TAC C$^{m+}$TG AAA $^{m+}$T | Trityl |
| NG-10-0065 | PMOtri | EG3 | GGC CAA ACC $^t$TCG GC$^t$T TAC C$^t$T G AAA T | H |
| NG-10-0607 | PMO-X | EG3 | GGC CAA ACC TCG GCT TAC CTG AAA T | 9-fluorene-carboxyl |
| NG-10-0060 | PMOcp | EG3 | GGC CAA ACC $^{cp}$TCG GC$^{cp}$T TAC C$^{cp}$T G AAA T | H |
| NG-10-0162 | PMO-COCH$_2$SH | EG3 | GGC CAA ACC TCG GCT TAC CTG AAA T | COCH2SH |
| NG-10-0328 | diphenylacetyl | EG3 | GGC CAA ACC TCG GCT TAC CTG AAA T | diphenylacetyl |
| NG-10-0134 | PMOapnPMOtri | OH | GGC C$^a$AA $^a$ACC $^t$TCG GC$^t$T $^t$TAC C$^t$TG AAA $^t$T | H |
| NG-10-0386 | PMO | DPA | GGC CAA ACC TCG GCT TAC CTG AAA T | 5'-diphenylac, 3'-trity |
| NG-07-0064 | PMO-3'-trityl | H-Pip | GGC CAA ACC TCG GCT TAC CTG AAA T | trityl |
| NG-10-0059 | PMOcp | EG3 | GGC CAA ACC $^{cp}$TCG GC$^{cp}$T $^{cp}$TAC C$^{cp}$T G AAA $^{cp}$T | H |
| NG-10-0135 | PMOtri | OH | GGC CAA ACC $^t$TCG GC$^t$T $^t$TAC C$^t$TG AAA $^t$T | H |
| NG-10-0168 | PMOapn PMOcys | OH | GGC CAA ACC $^a$TCG GC$^a$T $^a$TAC C$^a$TG AAA $^{SHc}$T | H |
| NG-10-0113 | PMOapnPMOtri | OH | GGC CAA ACC $^a$TCG GC$^a$T $^t$TAC C$^a$TG AAA $^a$T | H |
| NG-10-0385 | PMO | EG3 | GGC CAA ACC TCG GCT TAC CTG AAA T | diphenylphosphoryl |
| NG-10-0279 | PMO | OH | GGC CAA ACC TCG GCT TAC CTG AAA T | geranyl |
| NG-10-0055 | PMOplus disp | EG3 | GGC C$^+$AA $^+$ACC $^+$TCG GC$^+$T TAC C$^+$TG AAA T | H |
| NG-10-0105 | PMOsucc | EG3 | GGC CAA ACC $^s$TCG GC$^s$T TAC C$^s$T G AAA T | $\Delta^s$ |
| NG-10-0805 | PMO-X | EG3 | GGC CAA ACC $^{Etipip}$TCG GC$^{Etipip}$T TAC C$^{Etipip}$TG AAA $^{Etipip}$T | H |

TABLE 7-continued

M23D sequences (SEQ ID NO: 15) that incorporate modified intersubunit linkages and/or 3' and/or 5' terminal groups

| NG | PMO-X Modification | 5' | Sequence | 3' |
|---|---|---|---|---|
| NG-10-0811 | PMO-X | EG3 | GGC CAA ACC $^{pyrQMe}$TCG GC$^{pyrQMe}$T TAC C$^{pyrQMe}$TG AAA $^{pyrQMe}$T | H |
| NG-10-0057 | PMOplus 3'-pol | EG3 | GGC CAA ACC TCG GCT TAC C$^+$TG $^+$A$^+$A$^+$A T | H |
| NG-10-0625 | PMO-X | EG3 | GGC CAA ACC TCG GCT TAC CTG AAA T | 5-carboxyfluorescein |
| NG-10-0804 | dimer | EG3 | GGC CAA ACC TCG GCT TAC CTG AAA T | *dimerized* |
| NG-10-0066 | PMOtri | EG3 | GGC CAA ACC $^{\prime}$TCG GC$^{\prime}$T TAC C$^{\prime}$T G AAA $^{\prime}$T | H |
| NG-10-0280 | PMO disulfide | EG3 | GGC CAA ACC TCG GCT TAC CTG AAA T | COCH2 CH2SSPy |
| NG-10-0212 | PMOapn | EG3 | GGC CaAaA aACC aTCG GCaT aTaAC CaTG aAaAaA aT | H |
| NG-10-0156 | 3'-MeOtrityl | EG3 | GGC CAA ACC TCG GCT TAC CTG AAA T | MeO-Tr |
| NG-10-0062 | PMOhex | EG3 | GGC CAA ACC $^h$TCG GC$^h$T TAC C$^h$T G AAA $^h$T | H |
| NG-11-0043 | PMO-X | EG3 | GGC CAA ACC TCG GCT TAC CTG AAA T | guanidinyl |
| NG-10-0206 | PMOplus | EG3 | GGC C+A+A +ACC +TCG GC +T +T+AC C+TG +A+A+A +T | H |
| NG-10-0383 | PMO | EG3 | GGC CAA ACC TCG GCT TAC CTG AAA T | triphenylacetyl |
| NG-10-0325 | triphenylphos | OH | GGC CAA ACC FCG GCF TAC CFG AAA T | triphenylphos |
| NG-10-0272 | PMO-farnesyl | OH | GGC CAA ACC TCG GCT TAC CTG AAA T | farnesyl |

*Dimerized indicates the oligomer is dimerized by a linkage linking the 3' ends of the two monomers. For example, the linkage may be -COCH$_2$CH$_2$-S-CH(CONH$_2$)CH$_2$-CO-NHCH$_2$CH$_2$CO- or any other suitable linkage.

11. Antibacterial Applications

The invention includes, in another embodiment, an antibacterial antisense oilgomer for use in treating a bacterial infection in a mammalian host. In some embodiments, the oligomer comprises at least one linkage of type (B) and/or at least one terminal modification (e.g., at least one $R^{20}$) or combinations thereof, having between 10-20 bases and a targeting sequence of at least 10 contiguous bases complementary to a target region of the infecting bacteria's mRNA for acyl carrier protein (acpP), gyrase A subunit (gyrA), ftsZ, ribosomal protein S10 (rpsJ), leuD, mgtC, pirG, pcaA, and cmaI genes, where the target region contains the translational start codon of the bacterial mRNA, or a sequence that is within 20 bases, in an upstream (i.e., 5') or downstream (i.e., 3') direction, of the translational start codon, and where the oligomer binds to the mRNA to form a heteroduplex thereby to inhibit replication of the bacteria.

Also included are conjugates of the oligomers where conjugated to the oligomers is an arginine-rich carrier protein coupled to the oligonucleotide at the peptide's carboxyl terminus, and preferably represented by the peptide sequence (RXX)$_n$— or (RXR)$_n$, where X is an uncharged amino acid selected from the group consisting of alanine, β-alanine, valine, leucine, isoleucine, serine, glycine threonine, phenylalanine, tryptophan, and 6-aminohexanoic acid, and n=2 to 4. In exemplary embodiments, the carrier peptide has the sequence (RFF)$_n$, (RFF)$_n$R, or (RXR)$_n$ where n=2 to 4. The carrier peptide may be linked at its C-terminus to one end of the oligomer, e.g., the 3' or 5'-end, through a one- or two-amino acid linker, such as the linker AhxpβAla, where Ahx is 6-aminohexanoic acid and βAla is β-alanine. The carrier peptide has the ability, when conjugated to the 3' or 5'-end of the oligonucleotide, to enhance the anti-bacterial activity of the oligonucleotide, as measured by inhibition in bacterial growth in vitro over an eight-hour period, by a factor of at least 10, and preferably $10^2$ or $10^3$. In a preferred embodiment, the carrier peptide has the sequence (RAhxR)$_n$—, where n=4.

12. Modulating Nuclear Hormone Receptors

In another embodiment the present invention relates to compositions and methods for modulating expression of nuclear hormone receptors (NHR) from the nuclear hormone receptor superfamily (NHRSF), mainly by controlling or altering the splicing of pre-mRNA that codes for the receptors. Examples of particular NHRs include glucocorticoid receptor (GR), progesterone receptor (PR) and androgen receptor (AR). In certain embodiments, the antisense oligonucleotides and agents described herein lead to increased expression of ligand-independent or other selected forms of the receptors, and decreased expression of their inactive forms.

Embodiments of the present invention include oligomers and oligonucleotide analogs, for example oligomers comprising at least one linkage of type (B) and/or at least one terminal modification (e.g., at least one $R^{20}$) or combinations thereof, that are complementary to selected exonic or intronic sequences of an NHR, including the "ligand-binding exons" and/or adjacent introns of a NHRSF pre-mRNA, among other NHR-domains described herein. The term "ligand-binding exons" refers to exon(s) that are present in the wild-type mRNA but are removed from the primary transcript (the "pre-mRNA") to make a ligand-independent form of the mRNA. In certain embodiments, complementarity can be based on sequences in the sequence of pre-mRNA that spans a splice site, which includes, but is not limited to, complementarity based on sequences that span an exon-intron junction. In other embodiments, complementarity can be based solely on the sequence of the intron. In other embodiments, complementarity can be based solely on the sequence of the exon. (See, e.g., U.S. application Ser. No. 13/046,356, which is incorporated herein by reference.)

NHR modulators may be useful in treating NHR-associated diseases, including diseases associated with the expression products of genes whose transcription is stimulated or repressed by NHRs. For instance, modulators of NHRs that inhibit AP-1 and/or NF-κB can be useful in the treatment of inflammatory and immune diseases and disorders such as osteoarthritis, rheumatoid arthritis, multiple sclerosis, asthma, inflammatory bowel disease, transplant rejection, and graft vs. host disease, among others described herein and known in the art. Compounds that antagonize transactivation can be useful in treating metabolic diseases associated with increased levels of glucocorticoid, such as diabetes, osteoporosis and glaucoma, among others. Also, compounds that agonize transactivation can be useful in treating metabolic diseases associated with a deficiency in glucocorticoid, such as Addison's disease and others.

Embodiments of the present invention include methods of modulating nuclear NHR activity or expression in a cell, comprising contacting the cell with an antisense oligomer composed of morpholino subunits linked by phosphorus-containing intersubunit linkages joining a morpholino nitrogen of one subunit to a 5' exocyclic carbon of an adjacent subunit, wherein the oligonucleotide contains between 10-40 bases and a targeting sequence of at least 10 contiguous bases complementary to a target sequence, wherein the target sequence is a pre-mRNA transcript of the NHR, thereby modulating activity or expression of the NHR. In certain embodiments, the oligomer alters splicing of the pre-mRNA transcript and increases expression of a variant of the NHR. In some embodiments, the oligomer induces full or partial exon-skipping of one or more exons of the pre-mRNA transcript. In certain embodiments, the one or more exons encode at least a portion of a ligand-binding domain of the NHR, and the variant is a ligand independent form of the NHR. In certain embodiments, the one or more exons encode at least a portion of a transactivation domain of the NHR, and the variant has reduced transcriptional activation activity. In certain embodiments, the one or more exons encode at least a portion of a DNA-binding domain of the NHR. In certain embodiments, the one or more exons encode at least a portion of an N-terminal activation domain of the NHR. In certain embodiments, the one or more exons encode at least a portion of a carboxy-terminal domain of the NHR. In specific embodiments, the variant binds to NF-κB, AP-1, or both, and reduces transcription of one or more of their pro-inflammatory target genes.

In certain embodiments, the oligomer agonizes a transactivational transcriptional activity of the NHR. In other embodiments, the oligomer antagonizes a transactivational transcriptional activity of the NHR. In certain embodiments, the oligomer agonizes a transrepression activity of the NHR. In other embodiments, the oligomer antagonizes a transrepression activity of the NHR. In specific embodiments, the oligomer antagonizes a transactivational transcriptional activity of the NHR and agonizes a transrepression activity of the NHR. (See, e.g., U.S. Appn. Num. 61/313,652, which is incorporated herein by reference.)

EXAMPLES

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO and PMO containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

Example 1

Tert-Butyl 4-(2,2,2-Trifluoroacetamido)Piperidine-1-Carboxylate

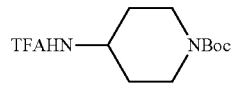

To a suspension of tert-butyl 4-aminopiperidine-1-carboxylate (48.7 g, 0.243 mol) and DIPEA (130 mL, 0.749 mol) in DCM (250 mL) was added ethyl trifluoroacetate (35.6 mL, 0.300 mol) dropwise while stirring. After 20 hours, the solution was washed with citric acid solution (200 mL×3, 10% w/v aq) and sodium bicarbonate solution (200 mL×3, conc aq), dried (MgSO$_4$), and filtered through silica (24 g). The silica was washed with DCM and the combined eluant was partially concentrated (100 mL), and used directly in the next step. APCI/MS calcd. for $C_{12}H_{19}F_3N_2O_3$ 296.1, found m/z=294.9 (M−1).

Example 2

2,2,2-Trifluoro-N-(Piperidin-4-Yl)Acetamide Hydrochloride

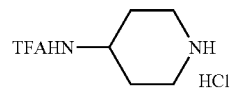

To a stirred DCM solution of the title compound of Example 1 (100 mL) was added dropwise a solution of hydrogen chloride (250 mL, 1.0 mol) in 1,4-dioxane (4 M). Stirring was continued for 6 hours, then the suspension was filtered, and the solid washed with diethyl ether (500 mL) to afford the title compound (54.2 g, 96% yield) as a white solid. APCI/MS calcd. for $C_7H_{11}F_3N_2O$, 196.1, found m/z=196.9 (M+1).

Example 3

(4-(2,2,2-Trifluoroacetamido)Piperidin-1-Yl)Phosphonic Dichloride

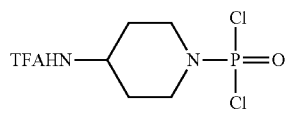

To a cooled (ice/water bath) suspension of the title compound of Example 2 (54.2 g, 0.233 mol) in DCM (250 mL) was added dropwise phosphorus oxychloride (23.9 mL, 0.256 mol) and DIPEA (121.7 mL, 0.699 mol) and stirred. After 15 minutes, the bath was removed and with continued stirring the mixture allowed to warm to ambient temperature. After 1 hour, the mixture was partially concentrated (100 mL), the suspension filtered, and the solid washed with diethyl ether to afford the title compound (43.8 g, 60% yield) as a white solid. The elutant was partially concentrated (100 mL), the resulting suspension filtered, and the solid washed with diethyl ether to afford additional title compound (6.5 g, 9% yield). ESI/MS calcd. for 1-(4-nitrophenyl)piperazine derivative $C_{17}H_{22}ClF_3N_5O_4P$, 483.1, found m/z=482.1 (M−1).

Example 4

((2S,6S)-6-((R)-5-Methyl-2,6-Dioxo-1,2,3,6-Tetrahydropyridin-3-Yl)-4-Tritylmorpholin-2-Yl)Methyl (4-(2,2,2-Trifluoroacetamido)Piperidin-1-Yl) Phosphonochloridate

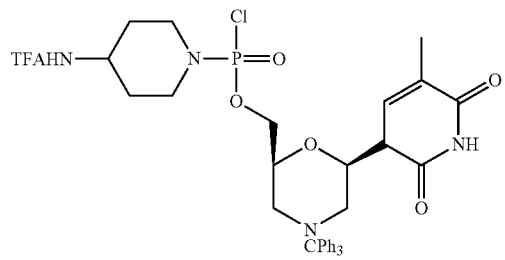

To a stirred, cooled (ice/water bath) solution of the title compound of Example 3 (29.2 g, 93.3 mmol) in DCM (100 mL) was added dropwise over 10 minutes a DCM solution (100 mL) of Mo(Tr)T # (22.6 g, 46.7 mmol), 2,6-Lutidine (21.7 mL, 187 mmol), and 4-(dimethylamino)pyridine (1.14 g, 9.33 mmol). The bath was allowed to warm to ambient temperature. After 15 hours, the solution was washed with a citric acid solution (200 mL×3, 10% w/v aq), dried (MgSO₄), concentrated, and the crude oil was loaded directly onto column. Chromatography [SiO₂ column (120 g), hexanes/EtOAc eluant (gradient 1:1 to 0:1), repeated x 3] fractions were concentrated to provide the title compound (27.2 g, 77% yield) as a white solid. ESI/MS calcd. for the 1-(4-nitrophenyl)piperazine derivative $C_{46}H_{50}F_3N_8O_8P$, 930.3, found m/z=929.5 (M−1).

Example 5

((2S,6R)-6-(6-Benzamido-9H-Purin-9-Yl)-4-Tritylmorpholin-2-Yl)Methyl (4-(2,2,2-Trifluoroacetamido)Piperidin-1-Yl)Phosphonochloridate

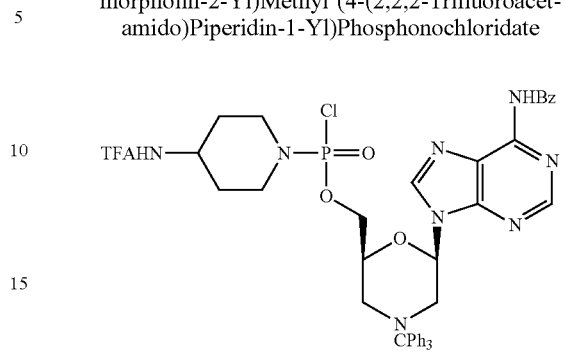

The title compound was synthesized in a manner analogous to that described in Example 4 to afford the title compound (15.4 g, 66% yield) as a white solid. ESI/MS calcd. for 1-(4-nitrophenyl)piperazine derivative $C_{53}H_{53}F_3N_{11}O_7P$, 1043.4, found m/z=1042.5 (M−1).

Example 6

(R)-Methyl(1-Phenylethyl)Phosphoramidic Dichloride

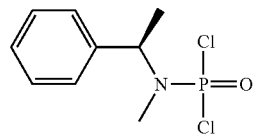

To a cooled (ice/water bath) solution of phosphorus oxychloride (2.83 mL, 30.3 mmol) in DCM (30 mL) was added sequentially, dropwise, and with stirring 2,6-lutidine (7.06 mL, 60.6 mmol) and a DCM solution of (R)-(+)-N,a-dimethylbenzylamine (3.73 g, 27.6 mmol). After 5 minutes, the bath was removed and reaction mixture allowed to warm to ambient temperature. After 1 hour, the reaction solution was washed with a citric acid solution (50 mL×3, 10% w/v aq), dried (MgSO₄), filtered through SiO₂ and concentrated to provide the title compound (3.80 g) as a white foam. ESI/MS calcd. for 1-(4-nitrophenyl)piperazine derivative $C_{19}H_{25}N_4O_4P$, 404.2, found m/z=403.1 (M−1).

Example 7

(S)-Methyl(1-Phenylethyl)Phosphoramidic Dichloride

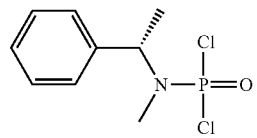

The title compound was synthesized in a manner analogous to that described in Example 6 to afford the title compound (3.95 g) as a white foam. ESI/MS calcd. for 1-(4-nitrophenyl)piperazine derivative $C_{19}H_{25}N_4O_4P$, 404.2, found m/z=403.1 (M−1).

Example 8

((2S,6R)-6-(5-Methyl-2,4-Dioxo-3,4-Dihydropyrimidin-1(2H)-Yl)-4-Tritylmorpholin-2-Yl)Methyl Methyl((R)-1-Phenylethyl)Phosphoramidochloridate

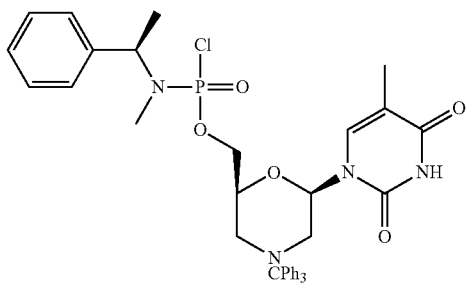

The title compound was synthesized in a manner analogous to that described in Example 4 to afford the title chlorophosphoroamidate (4.46 g, 28% yield) as a white solid. ESI/MS calcd. for $C_{38}H_4OClN_4O_5P$, 698.2, found m/z=697.3 (M−1).

Example 9

((2S,6R)-6-(5-Methyl-2,4-Dioxo-3,4-Dihydropyrimidin-1(2H)-Yl)-4-Tritylmorpholin-2-Yl)Methyl Methyl((S)-1-Phenylethyl)Phosphoramidochloridate

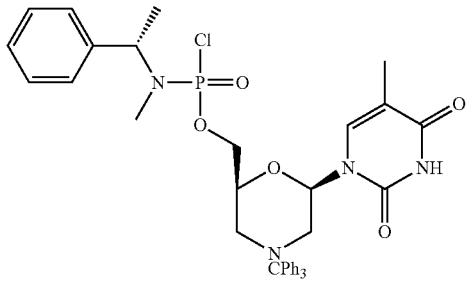

The title compound was synthesized in a manner analogous to that described in Example 4 to afford the title chlorophosphoroamidate (4.65 g, 23% yield) as a white solid. ESI/MS calcd. for $C_{38}H_4OClN_4O_5P$, 698.2, found m/z=697.3 (M−1).

Example 10

(4-(Pyrrolidin-1-Yl)Piperidin-1-Yl)Phosphonic Dichloride Hydrochloride

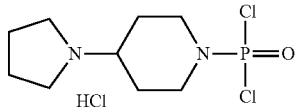 [SMILES: O=P(Cl)(Cl)N1CCC(N2CCCC2)CC1 ; Cl]

To a cooled (ice/water bath) solution of phosphorus oxychloride (5.70 mL, 55.6 mmol) in DCM (30 mL) was added 2,6-lutidine (19.4 mL, 167 mmol) and a DCM solution (30 mL) of 4-(1-pyrrolidinyl)-piperidine (8.58 g, 55.6 mmol) and stirred for 1 hour. The suspension was filtered and solid washed with excess diethyl ether to afford the title pyrrolidine (17.7 g, 91% yield) as a white solid. ESI/MS calcd. for 1-(4-nitrophenyl)piperazine derivative $C_{19}H_{30}N_5O_4P$, 423.2, found m/z=422.2 (M−1).

Example 11

((2S,6R)-6-(5-Methyl-2,4-Dioxo-3,4-Dihydropyrimidin-1(2H)-Yl)-4-Tritylmorpholin-2-Yl)Methyl (4-(Pyrrolidin-1-Yl)Piperidin-1-Yl)Phosphonochloridate Hydrochloride

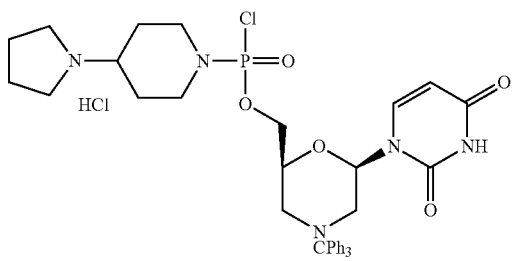

To a stirred, cooled (ice/water bath) solution of the dichlorophosphoramidate 8 (17.7 g, 50.6 mmol) in DCM (100 mL) was added a DCM solution (100 mL) of Mo(Tr)T # (24.5 g, 50.6 mmol), 2,6-Lutidine (17.7 mL, 152 mmol), and 1-methylimidazole (0.401 mL, 5.06 mmol) dropwise over 10 minutes. The bath was allowed to warm to ambient temperature as suspension was stirred. After 6 hours, the suspension was poured onto diethyl ether (1 L), stirred 15 minutes, filtered and solid washed with additional ether to afford a white solid (45.4 g). The crude product was purified by chromatography [$SiO_2$ column (120 gram), DCM/MeOH eluant (gradient 1:0 to 6:4)], and the combined fractions were poured onto diethyl ether (2.5 L), stirred 15 min, filtered, and the resulting solid washed with additional ether to afford the title compound (23.1 g, 60% yield) as a white solid. ESI/MS calcd. for 1-(4-nitrophenyl)piperazine derivative $C_{48}H_{57}N_8O_7P$, 888.4, found m/z=887.6 (M−1).

Example 12

3-(Tert-Butyldisulfanyl)-2-(Isobutoxycarbonylamino)Propanoic Acid

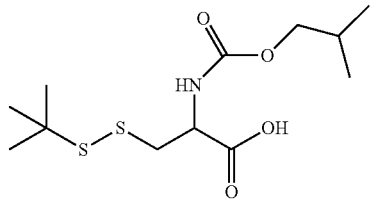

To S-tert-butylmercapto-L-cysteine (10 g, 47.8 mmol) in $CH_3CN$ (40 mL) was added $K_2CO_3$ (16.5 g, 119.5 mmol) in $H_2O$ (20 mL). After stirring for 15 minutes, iso-butyl chloroformate (9.4 mL, 72 mmol) was injected slowly. The reaction was allowed to run for 3 hours. The white solid was filtered through Celite; the filtrate was concentrated to remove $CH_3CN$. The residue was dissolved in ethyl acetate (200 mL), washed with 1N HCl (40 mL×3), brine (40×1), dried over $Na_2SO_4$. Desired product (2) was obtained after chromatography (5% MeOH/DCM).

Example 13

Tert-Butyl 4-(3-(Tert-Butyldisulfanyl)-2-(Isobutoxycarbonylamino)Propanamido)Piperidine-1-Carboxylate

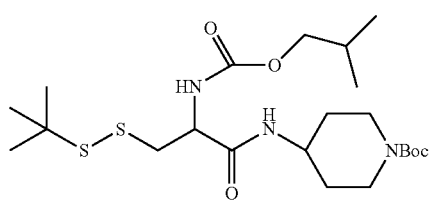

3

To the acid (compound 2 from Example 12, 6.98 g, 22.6 mmol) in DMF (50 ml was added HATU (8.58 g, 22.6 mmol). After 30 min, Hunig base (4.71 ml, 27.1 mmol) and 1-Boc-4-amino piperidine (5.43 g, 27.1 mmol) were added to the mixture. The reaction was continued stirring at RT for another 3 h. DMF was removed at high vacuum, the crude residue was dissolved in EtAc (300 ml), washed with H₂O (50 ml×3). The final product (3) was obtained after ISCO purification (5% MeOH/DCM).

Example 14

Isobutyl 3-(Tert-Butyldisulfanyl)-1-Oxo-1-(Piperidin-4-Ylamino)Propan-2-Ylcarbamate

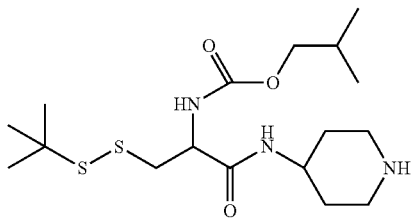

4

To compound 3 prepared in Example 13 (7.085 g, 18.12 mmol) was added 30 ml of 4M HCl/Dioxane. The reaction was completed after 2 h at RT. The HCl salt (4) was used for the next step without further purification.

Example 15

Isobutyl 3-(Tert-Butyldisulfanyl)-1-(1-(Dichlorophosphoryl)Piperidin-4-Ylamino)-1-Oxopropan-2-Ylcarbamate

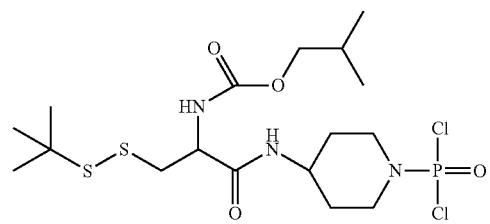

5

To compound 4 prepared in Example 15 (7.746 g, 18.12 mmol) in DCM (200 ml) at −78° C. was slowly injected POCl₃ (1.69 ml, 18.12 mmol) under Ar, followed by the addition of Et₃N (7.58 ml, 54.36 mmol). The reaction was stirred at RT for 5 h, concentrated to remove excess base and solvent. The product (5) was given as white solid after ISCO purification (50% EtAc/Hexane).

Example 16

Isobutyl 3-(Tert-Butyldisulfanyl)-1-(1-(Chloro(((2S,6R)-6-(5-Methyl-2,4-Dioxo-3,4-Dihydropyrimidin-1(2H)-Yl)-4-Tritylmorpholin-2-Yl)Methoxy)Phosphoryl)Piperidin-4-Ylamino)-1-Oxopropan-2-Ylcarbamate

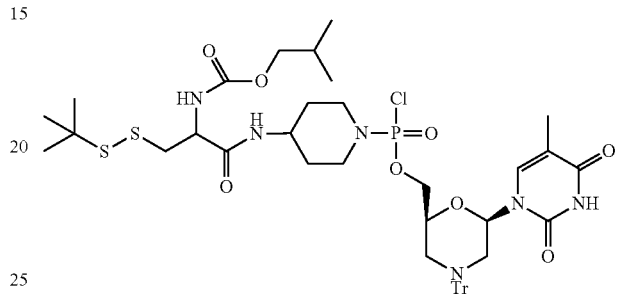

6

To 1-((2R,6S)-6-(hydroxymethyl)-4-tritylmorpholin-2-yl)-5-methylpyrimidine-2,4(1H,3H)-dione (moT(Tr)) (5.576 g, 10.98 mmol) in DCM (100 ml) at 0° C., was added lutidine (1.92 ml, 16.47 mmol) and DMAP (669 mg, 5.5 mmol), followed by the addition of 4 (6.13 g, 12.08 mmol). The reaction was left stirring at RT for 18 h. The desired product (6) was obtained after ISCO purification (50% EtAc/Hexane).

Example 17

((2S,6R)-6-(5-Methyl-2,4-Dioxo-3,4-Dihydropyrimidin-1(2H)-Yl)-4-Tritylmorpholin-2-Yl)Methyl Hexyl(Methyl)Phosphoramidochloridate

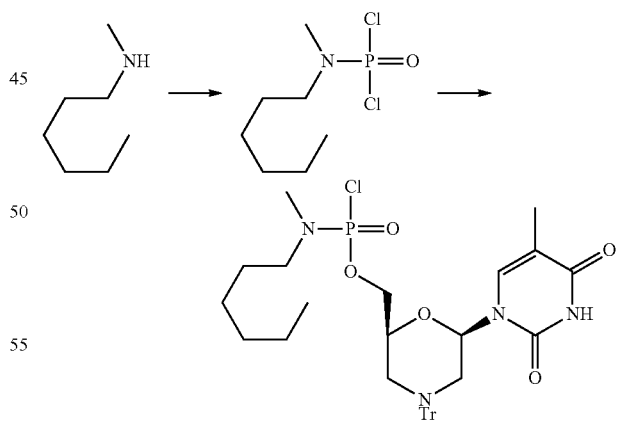

A DCM (80 ml) solution of N-hydroxylmethylamine (4.85 ml, 32 mmol) was cooled down to −78° C. under N2. A solution of phosphoryl chloride (2.98 ml, 32 mmol) in DCM (10 ml), followed by a solution of Et₃N (4.46 ml, 32 mmol) in DCM (10 ml), was added slowly. The stirring was continued while the reaction was allowed to warm to RT overnight. The desired product (1) was given as clear oil after ISCO purification (20% EtAc/Hexane).

To moT(Tr) (5.10 g, 10.54 mmol) in DCM (100 ml) at 0° C., was added lutidine (3.68 ml, 31.6 mmol) and DMAP (642 mg, 5.27 mmol), followed by the addition of 1 (4.89 g, 21.08 mmol). The reaction was left stirring at RT for 18 h. The desired product (2) was obtained after ISCO purification (50% EtOAc/Hexane).

Example 18

((2S,6R)-6-(5-Methyl-2,4-Dioxo-3,4-Dihydropyrimidin-1(2H)-Yl)-4-Tritylmorpholin-2-Yl)Methyl Dodecyl(Methyl)Phosphoramidochloridate

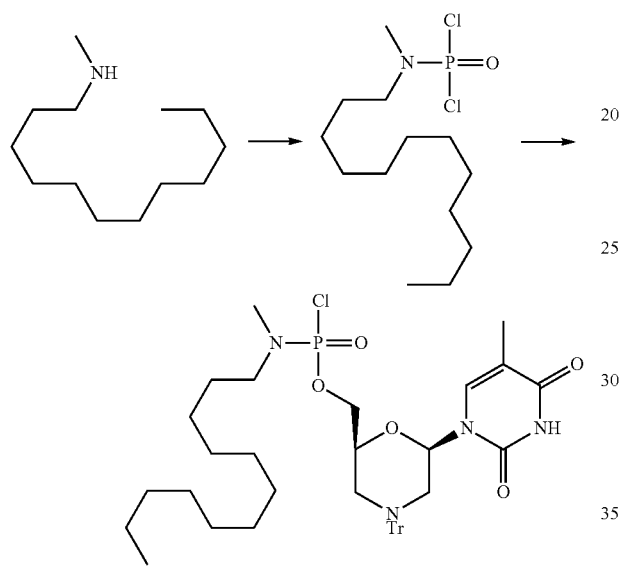

The title compound was prepared according to the general procedures described in Examples 6 and 8.

Example 19

((2S,6R)-6-(5-Methyl-2,4-Dioxo-3,4-Dihydropyrimidin-1(2H)-Yl)-4-Tritylmorpholin-2-Yl)Methyl Morpholinophosphonochloridate

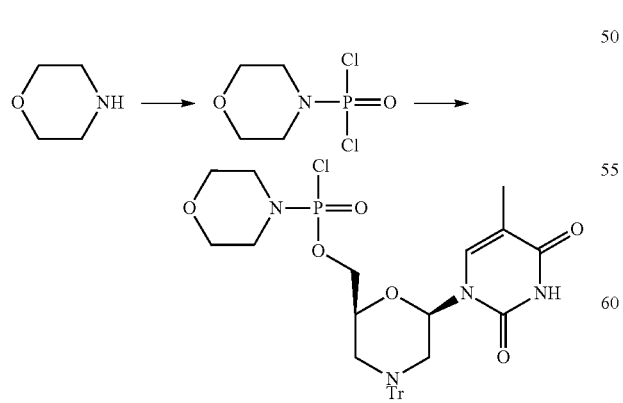

The title compound was prepared according to the general procedures described in Examples 6 and 8.

Example 20

((2S,6R)-6-(5-Methyl-2,4-Dioxo-3,4-Dihydropyrimidin-1(2H)-Yl)-4-Tritylmorpholin-2-Yl)Methyl (S)-2-(Methoxymethyl)Pyrrolidin-1-Ylphosphonochloridate

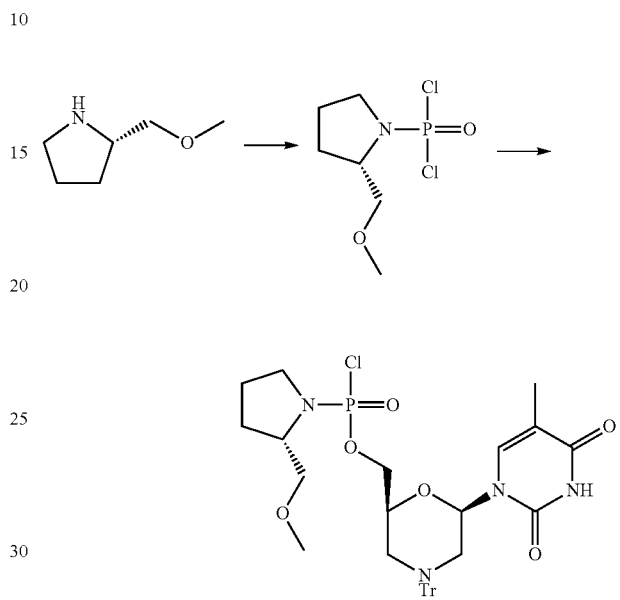

The title compound was prepared according to the general procedures described in Examples 6 and 8.

Example 21

((2S,6R)-6-(5-Methyl-2,4-Dioxo-3,4-Dihydropyrimidin-1(2H)-Yl)-4-Tritylmorpholin-2-Yl)Methyl 4-(3,4,5-Trimethoxybenzamido)Piperidin-1-Ylphosphonochloridate

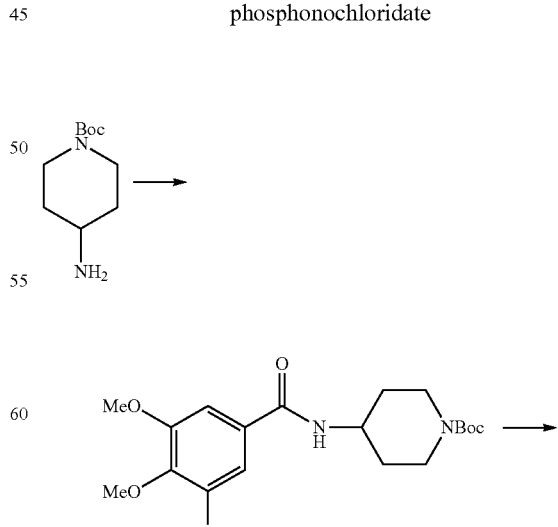

101

-continued

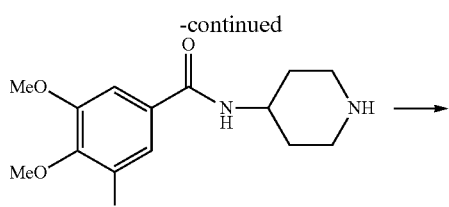

8

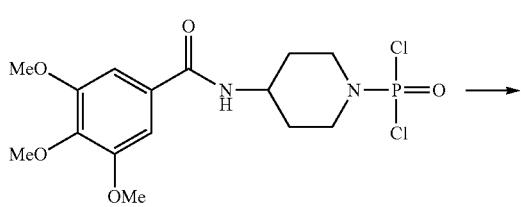

9

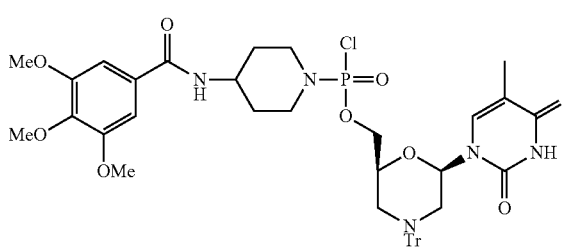

10

To 1-Boc-4-piperidine (1 g, 5 mmol) in DCM (20 ml) was added Hunig base (1.74 ml, 10 mmol), followed by the addition of 3,4,5-trimethoxybenzoyl chloride (1.38 g, 6 mmol). The reaction was run at RT for 3 h, concentrated to remove solvent and excess base. The residue was dissolved in EtAc (100 ml), washed with 0.05N HCl (3×15 ml), sat. NaHCO$_3$ (2×15 ml), dried over Na$_2$SO$_4$. Product (1) was obtained after ISCO purification (5% MeOH/DCM).

To 7 was added 15 ml of 4N HCl/Dioxane, reaction was terminated after 4 h. 8 was obtained as white solid.

A DCM (20 ml) solution of 8 (1.23 g, 4.18 mmol) was cooled down to −78° C. under N$_2$. A solution of phosphoryl chloride (0.39 ml, 4.18 mmol) in DCM (2 ml), followed by a solution of Et$_3$N (0.583 ml, 4.18 mmol) in DCM (2 ml), was added slowly. The stirring was continued while the reaction was allowed to warm to RT overnight. The desired product (9) was obtained after ISCO purification (50% EtAc/Hexane).

To moT(Tr) (1.933 g, 4.0 mmol) in DCM (20 ml) at 0° C., was added lutidine (0.93 ml, 8 mmol) and DMAP (49 mg, 0.4 mmol), followed by the addition of 9 (1.647 g, 4 mmol). The reaction was left stirring at RT for 18 h. The desired product (10) was obtained after ISCO purification (50% EtAc/Hexane).

102

Example 22

Synthesis of Cyclophosphoramide Containing Subunit ($^{CP}$T)

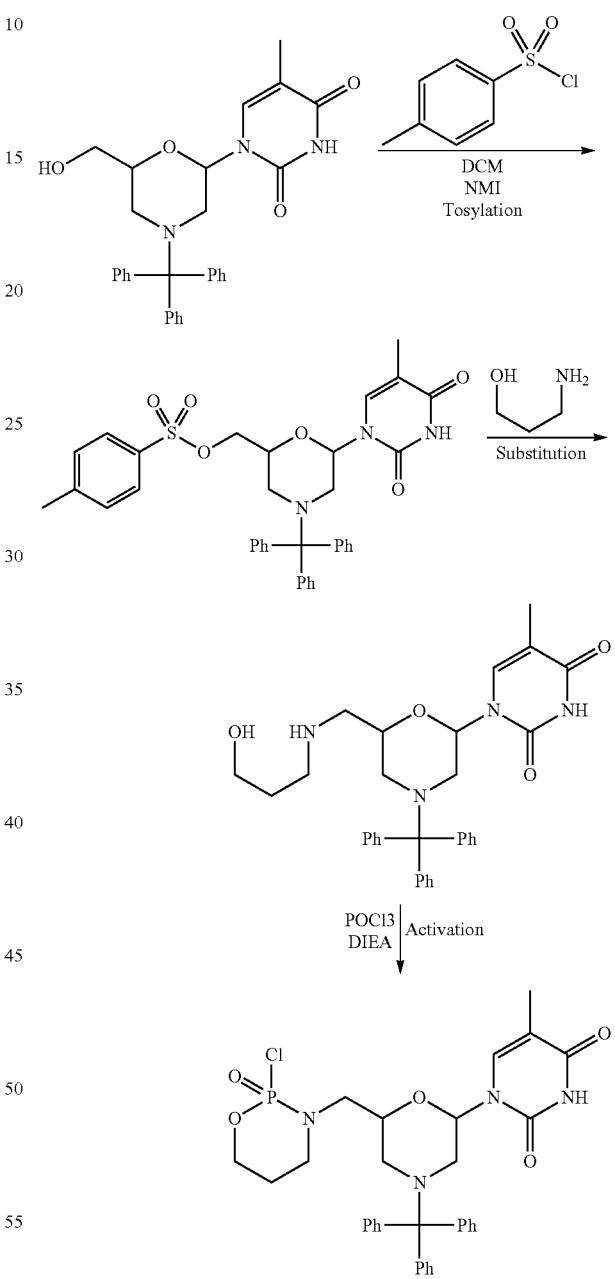

The moT subunit (25 g) was suspended in DCM (175 ml) and NMI (N-methylimidazole, 5.94 g, 1.4 eq.) was added to obtain a clear solution. Tosyl chloride was added to the reaction mixture, and the reaction progress was monitored by TLC until done (about 2 hours). An aqueous workup was performed by washing with 0.5 M citric acid buffer (pH=5), followed by brine. The organic layer was separated and dried over Na2SO4. Solvent was removed with a rotavaporator to obtain the crude product which was used in the next step without further purification.

The moT Tosylate prepared above was mixed with propanolamine (1 g/10 ml). The reaction mixture was then placed in an oven at 45° C. overnight followed by dilution with DCM (10 ml). An aqueous workup was performed by washing with 0.5 M citric acid buffer (pH=5), followed by brine. The organic layer was separated and dried over $Na_2SO_4$. Solvent was removed with a rotavaporator to obtain the crude product. The curde product was analyzed by NMR and HPLC and determined to be ready for the next step without further purification.

The crude product was dissolved in DCM (2.5 ml DCM/g, 1 eq.) and mixed with DIEA (3 eq.). This solution was cooled with dry ice-acetone and $POCl_3$ was added dropwise (1.5 eq.). The resultant mixture was stirred at room temperature overnight. An aqueous workup was performed by washing with 0.5 M citric acid buffer (pH=5), followed by brine. The organic layer was separated and dried over $Na_2SO_4$. Solvent was removed with a rotavaporator to obtain the crude product as a yellowish solid. The crude product was purified by silica gel chromatography (crude product/silica=1 to 5 ratio, gradient DCM to 50% EA/DCM), and fractions were pooled according to TLC analysis. Solvent was removed to obtain the desired product as a mixture of diastereomers. The purified product was analyzed by HPLC (NPP quench) and NMR (H-1 and P-31).

The diastereomeric mixture was separated according to the following procedure. The mixture (2.6 g) was dissolved in DCM. This sample was loaded on a RediSepRf column (80 g normal phase made by Teledyne Isco) and eluted with 10% EA/DCM to 50% EA/DCM over 20 minutes. Fractions were collected and analyzed by TLC. Fractions were pooled according to TLC analysis, and solvent was removed with a rotavaporator at room temperature. The diastereomeric ratio of ther pooled fractions was determined by P-31 NMR and NPP-TFA analysis. If needed, the above procedure was repeated until the diastereomeric ratio reached 97%.

Example 23

Global Cholic Acid Modification of PMOplus

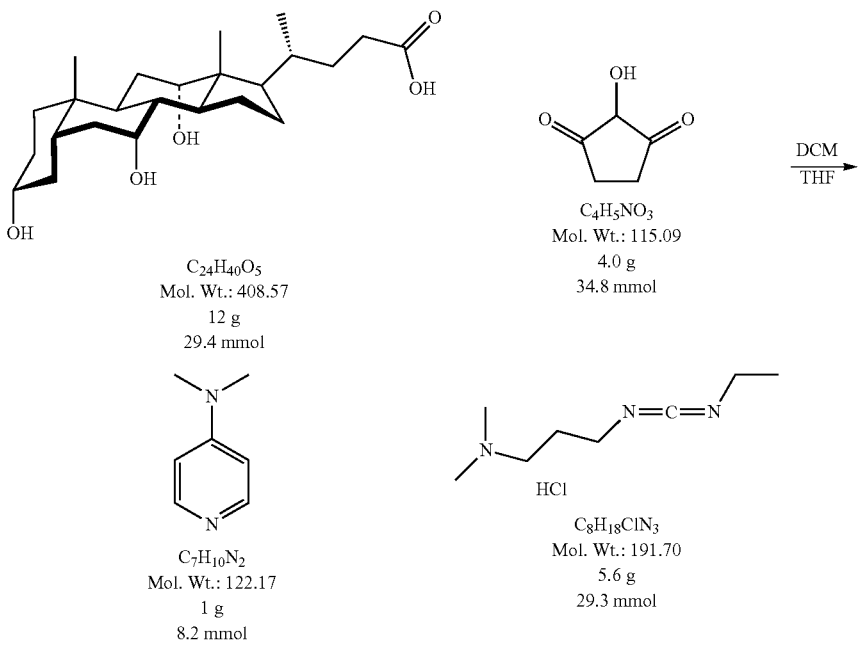

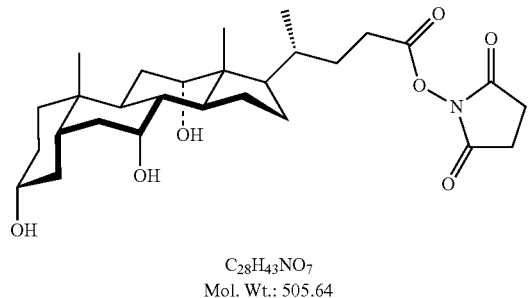

-continued

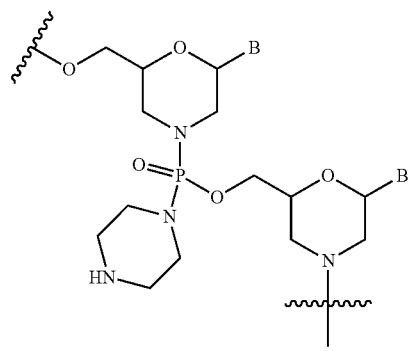
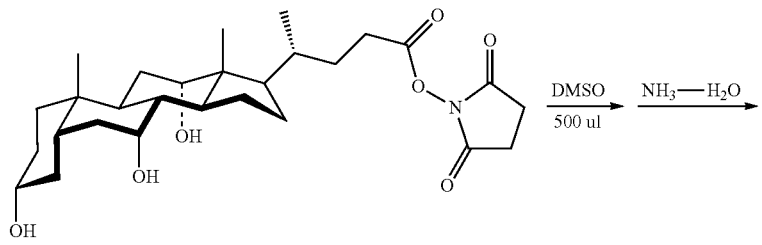

MW: 7076
09DE14-J(A7 to F7)
NG-09-0367
3 plus site
3'-end H
20 mg
2.8 umol

Chemical Formula: $C_{28}H_{43}NO_7$
Molecular Weight: 505.64352
404-152
13 mg
25 ummol

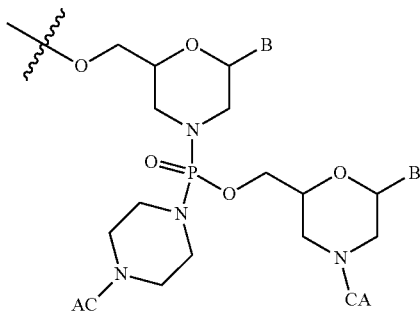

Molecular Weight: 391.56
7076 + 4 * 391
7467
7858
8249
7640

The succinimide activated cholic acid derivative was prepared according to the following procedure. Cholic acid (12 g, 29.4 mmol), N-hydroxysuccinimide (4.0 g, 34.8 mmol), EDCI (5.6 g, 29.3 mmol), and DMAP (1 g, 8.2 mmol) were charged to a round bottom flask. DCM (400 ml) and THF (40 ml) were added to dissolve. The reaction mixture was stirred at room temperature overnight. Water (400 ml) was then added to the reaction mixture, the organic layer separated and washed with water (2×400 ml), followed by sat. NaHCO$_3$ (300 ml) and brine (300 ml). The organic layer was then dried over Na$_2$SO$_4$. Solvent was removed with rotavaporator to obtain a white solid. The curde product was dissolved in chloroform (100 ml) and precipitated into heptane (1000 ml). The solid was collected by filtration, analyzed by HPLC and NMR and used without further purification.

An appropriate amount of PMOplus (20 mg, 2.8 μmol) was weighed into a vial (4 ml) and dissolved in DMSO (500 ul). The activated cholate ester (13 mg, 25 μmol) was added to the reaction mixture according to the ratio of two equivalent of active ester per modification site followed by stirring at room temperature overnight. Reaction progress was determined by MALDI and HPLC (C-18 or SAX).

After the reaction was complete (as determined by disappearance of starting PMOplus), 1 ml of concentrated ammonia was added to the reaction mixture once the reaction is complete. The reaction vial was then placed in an oven (45° C.) overnight (18 hours) followed by cooling to room temperature and dilution with 1% ammonia in water (10 ml). This sample was loaded on to an SPE column (2 cm), and the vial rinsed with 1% ammonia solution (2×2 ml). The SPE column was washed with 1% ammonia in water (3×6 ml), and the product eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

This same procedure is applicable to deoxycholic acid activation and conjugation to a PMO$^+$.

Example 24

Global Guanidinylation of PMOplus

An appropriate amount of PMOplus (25 mg, 2.8 μmol) was weighed into a vial (6 ml). 1H-Pyrozole-1-carboxamidine chloride (15 mg, 102 μmol) and potassium carbonate (20 mg, 0.15 mmol) were added to the vial. Water was added (500 ul), and the reaction mixture was stirred at room temperature overnight (about 18 hours). Reaction completion was determined by MALDI.

Once complete, the reaction was diluted with 1% ammonia in water (10 ml) and loaded on to an SPE column (2 cm). The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 25
Global Thioacetyl Modification of PMOplus (M23D)
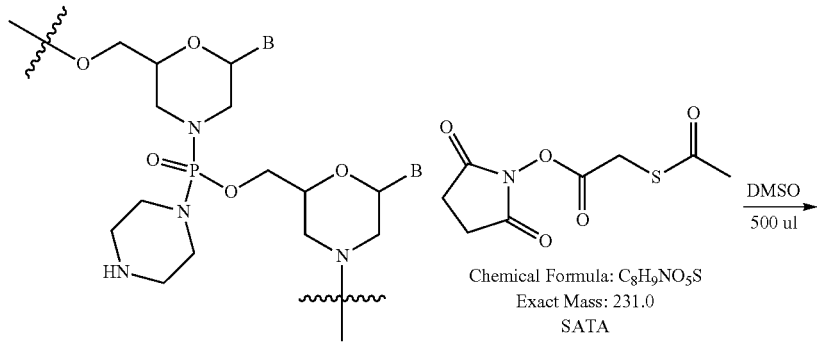
MW: 8710
10 Feb. 2016-J(D1)
NG-09-0719
M23D
3 plus site
3'-end H
20 mg
2.3 umol
Chemical Formula: $C_8H_9NO_5S$
Exact Mass: 231.0
SATA
N-succinimidyl-S-acetylthioacetate
7 mg
28 umol
3 eq.
$\xrightarrow{\text{DMSO}}{500 \text{ ul}}$
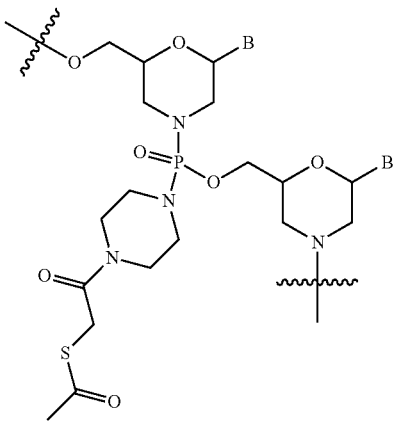
Exact Mass: 117.0
MW: 8710 * 117n
8827
8944
9061
9178
↓ Ammonolysis
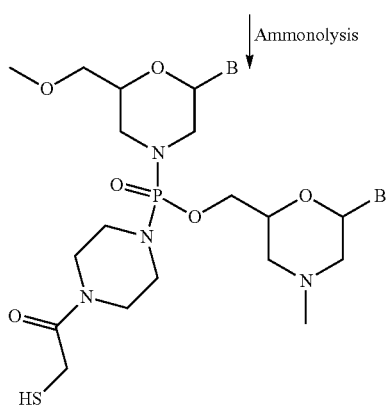
Exact Mass: 75.0
8710 + n * 75
8785
8860
8935
9010

An appropriate amount of PMOplus (20 mg, 2.3 µmol) was weighed in to a vial (4 ml) and dissolved in DMSO (500 ul). N-succinimidyl-S-acetylthioacetate (SATA) (7 mg, 28 mol) was added to the reaction mixture, and it was allowed to stir at room temperature overnight. Reaction progress was monitored by MALDI and HPLC.

Once complete, 1% ammonia in water was added to the reaction mixture, and it was stirred at room temperature for 2 hours. This solution was loaded on to an SPE column (2 cm), The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 26

Global Succinic Acid Modification of Pmoplus

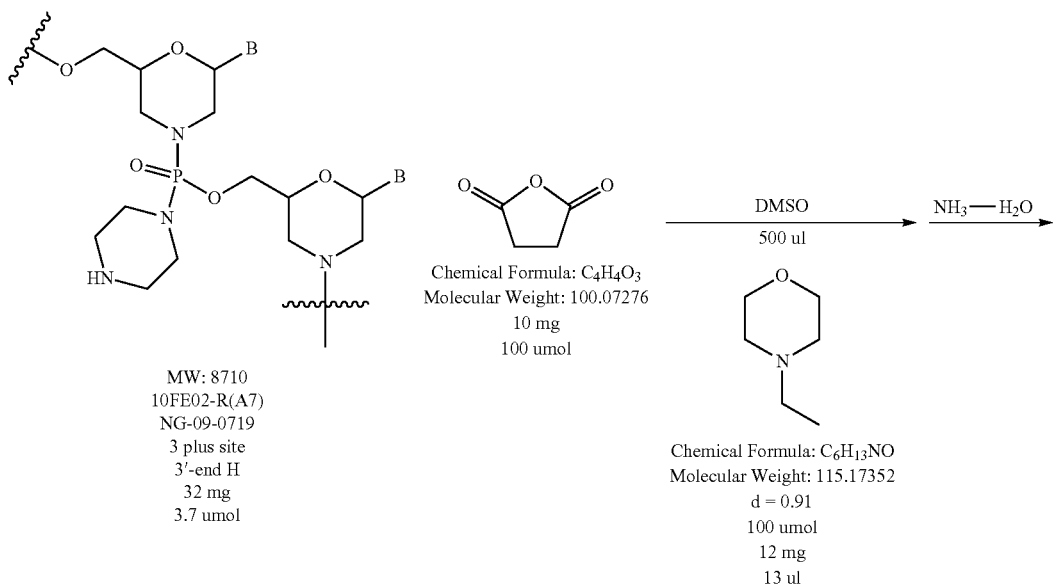

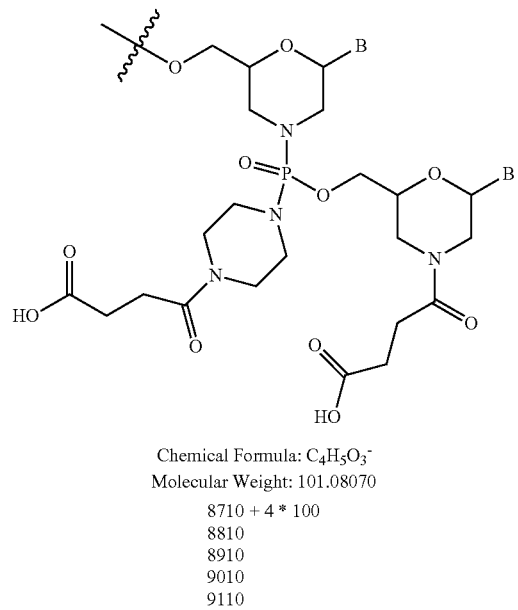

An appropriate amount of PMOplus (32 mg, 3.7 μmol) was weighed in to a vial (4 ml) and dissolved in DMSO (500 ul). N-ethyl morpholino (12 mg, 100 μmol) and succinic anhydride (10 mg, 100 μmol) were added to the reaction mixture, and it was allowed to stir at room temperature overnight. Reaction progress was monitored by MALDI and HPLC.

Once complete, 1% ammonia in water was added to the reaction mixture, and it was stirred at room temperature for 2 hours. This solution was loaded on to an SPE column (2 cm), The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

The above procedure is applicable to glutartic acid (glutaric anhydride) and tetramethyleneglutaric acid (tetramethyleneglutaric anhydride) modification of PMOplus as well.

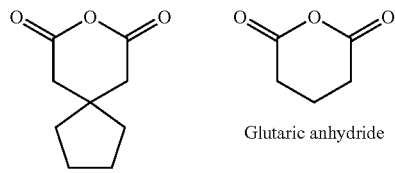

Tetramethylenglutaric anhydride    Glutaric anhydride

Example 27

Treatment of MDX Mice with Exemplary PMO Oligomers of the Invention

Figure 5:
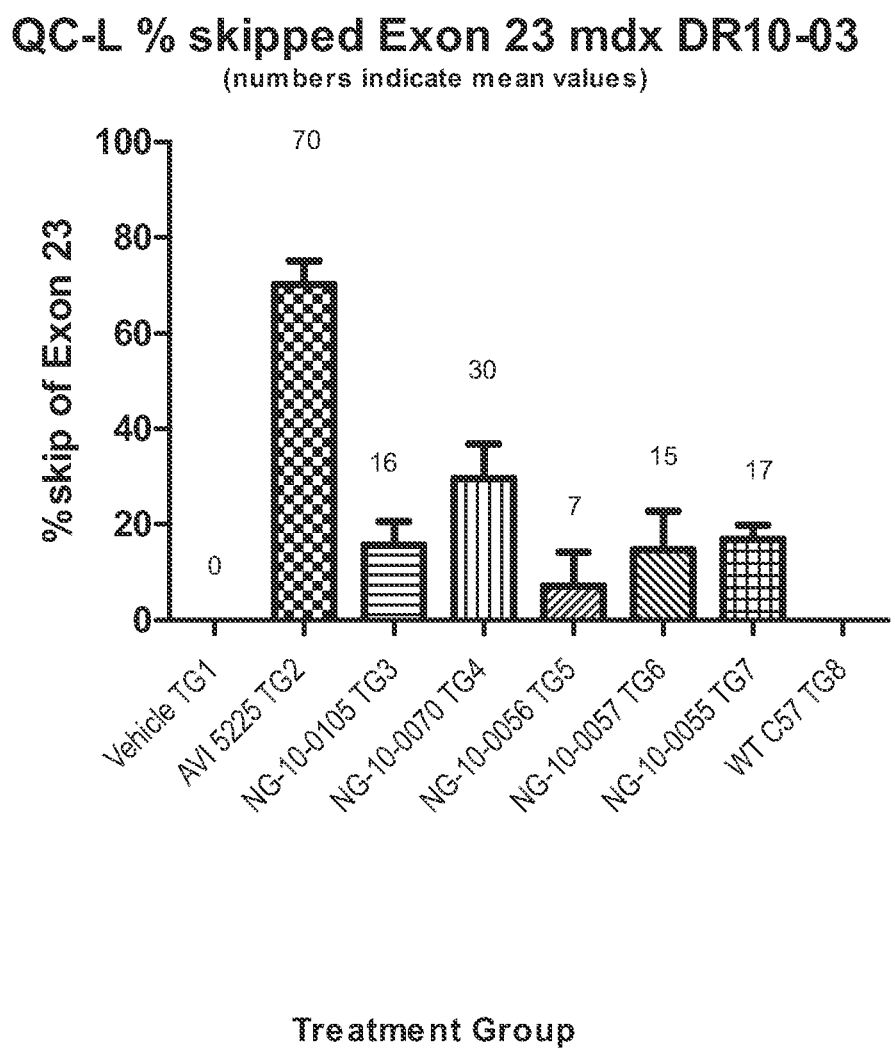
FIG. 5 shows exon skipping activity of representative oligomers.

The MDX mouse is an accepted and well-characterized animal model for Duchene muscular dystrophy (DMD) containing a mutation in exon 23 of the dystrophin gene. The M23D antisense sequence (SEQ ID NO:15) is known to induce exon 23 skipping and restoration of functional dystrophin expression. MDX mice were dosed once (50 mg/kg) by tail vein injection with either M23D PMO+ oligomers (NG-09-0711, NG-10-0055, NG-10-0056) or two PMO compounds containing either the 4-aminopiperidinyl linkage (NG-10-0070 containing the PMO$^{apn}$ linkage described above and shown in FIG. 2) and the 4-succinamidopiperazinyl linkage (NG-10-0105 containing the PMO$^{suc}$ linkage described above and shown in FIG. 2). A peptide-conjugated PMO (PPMO) was used as a positive control in the experiment (AVI-5225; SEQ ID NO: 16). All tested oligomer has the same antisense sequence, but varied by type of linkage or a peptide (in the case of AVI-5225, see Table 8)). One week post-injection, the MDX mice were sacrificed and RNA was extracted from various muscle tissues. End-point PCR was used to determine the relative abundance of dystrophin mRNA containing exon 23 and mRNA lacking exon 23 due to antisense-induced exon skipping. Percent exon 23 skipping is a measure of antisense activity in vivo. FIG. 5 shows the results from the quadriceps one week post-treatment. NG-10-0070 containing four cationic 4-aminopiperidinyl linkages shows a two-fold increase in activity compared to any of the PMO+ compounds (NG-10-0055, -0056 and -0057). The NG-10-0105 compound containing four anionic 4-succinamidopiperazinyl linkages was equally active compared to the PMO+ oligomers. As expected the AVI-5225 PPMO (peptide conjugated) compound was most effective due to the cell penetrating delivery peptide. The vehicle and WT C57 (wild-type mice) treatments were negative controls and did not express exon 23 skipped dystrophin mRNA.

TABLE 8

Sequences of Example 27

| Name | Sequence (5' to 3') | SEQ ID NO |
|---|---|---|
| M23D | GGCCAAACCTCGGCTTACCTGAAAT | 15 |
| NG-09-0711 | GGC CAA ACC +TCG GC+T TAC C+TG AAA +T | N/A |
| NG-10-0055 | GGC C+AA +ACC +TCG GC+T TAC C+TG AAA T | N/A |
| NG-10-0056 | GGC C+A+A ACC TCG GCT TAC CTG AAA T | N/A |
| NG-10-0057 | GGC CAA ACC TCG GCT TAC CTG +AAA T | N/A |
| NG-10-0070 | GGC CAA ACC $^{apn}$TCG GC$^{apn}$T TAC C$^{apn}$TG AAA $^{apn}$T | N/A |
| NG-10-0105 | GGC CAA ACC $^{suc}$TCG GC$^{suc}$T TAC C$^{suc}$TG AAA T | N/A |
| AVI-5225 | GGCCAAACCTCGGCTTACCTGAAAT-RAhxRRBRRAhxRRBRAhxB | 16 |

Figure 6:
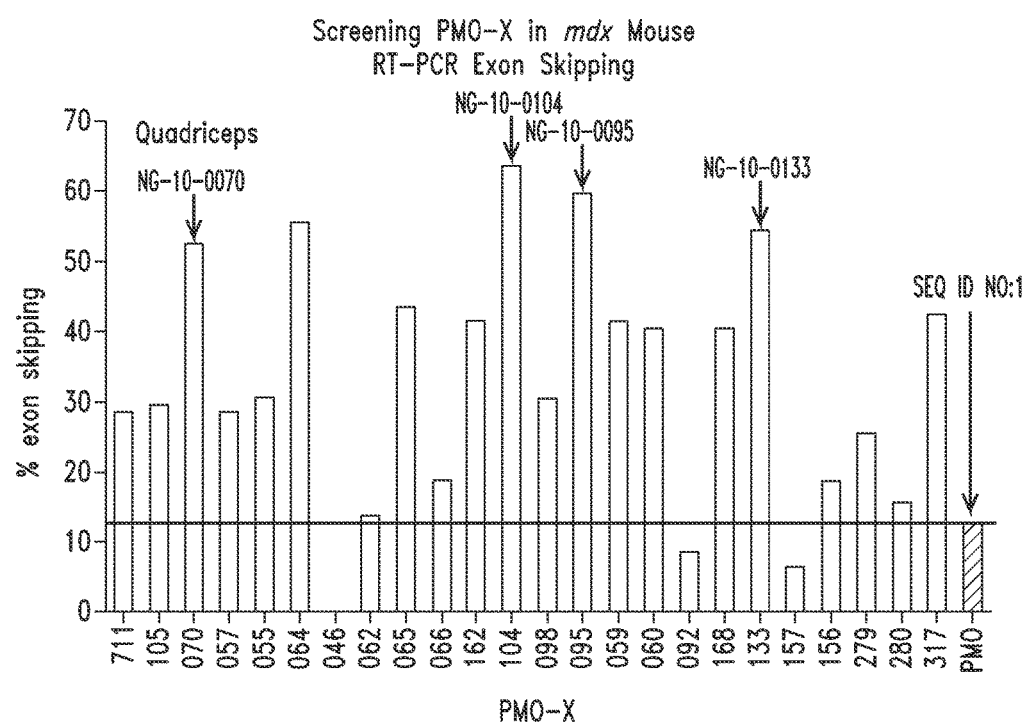
FIG. 6 is a bar graph showing exon skipping in the mdx mouse model.

Additional experiments in support of the invention were performed using a wider range of modified intersubunit linkages within the M23D PMO and used in the MDX mouse model as described above. A subset of the oligomers with the linkages are listed as above in Table 7. FIG. 6 shows the results from this expanded screen and shows the M23D oligomers with the highest activity are NG-10-0070, NG-10-0104, NG-10-0095 and NG-10-0133 comprising linkages b10, b54, b10 and b10, respectively (in FIG. 6, the labels on the x axis correspond to the last 3 digits of the compound ID#). The MDX mice received a single injection intravenously at a 50 mg/kg dose. Other active compounds shown in FIG. 6 are M23D PMO comprising terminal modifications and are described above in Table 6. All the compounds were compared to a PMO without any intersubunit or terminal modifications (SEQ ID NO:15).

Additional experiments in support of the invention used an even greater expansion of compounds with intersubunit and terminal linkages. Intersubunit linkage modifications are shown above in Table 9. Results using those compounds are shown below in Table 9. The results are ordered with the most active compounds at the top of the table.

TABLE 9

Exon 23 skipping in quadricep and diaphram tissue from MDX mice treated with PMO-X compounds of the invention

| NG # | PMO-X modification | Dose mg/kg | Exon skip % Quads | Exon skip % Diaph |
|---|---|---|---|---|
| NG-10-0383 | PMO | 30 | 61 | 20 |
| NG-10-0325 | triphenylphos | 30 | 54 | 46 |
| NG-10-0272 | PMO-farnesyl | 30 | 48 | 14 |
| NG-10-0102 | PMO | 30 | 44 | 23 |
| NG-10-0330 | trimethoxybenzoyl | 30 | 40 | 7 |
| NG-10-0056 | PMOplus 5'-pol | 23 | 40 | 13 |
| NG-07-0064 | PMO-3'-trityl | 30 | 37 | 24 |
| NG-10-0382 | PMO | 30 | 36 | 18 |
| NG-10-0278 | PMOpyr | 26 | 35 | 29 |
| NG-10-0210 | PMOapn | 31 | 34 | 19 |
| NG-10-0098 | PMOpyr | 30 | 31 | 19 |
| NG-10-0070 | PMOapn | 30 | 30 | 10 |
| NG-10-0095 | PMOapn | 30 | 30 | 11 |
| NG-10-0317 | PMO | 30 | 30 | 17 |
| NG-10-0477 | PMO triMe Gly | 30 | 28 | 32 |
| NG-10-0133 | PMOapn | 30 | 28 | 17 |
| NG-10-0387 | PMO | 30 | 28 | 25 |
| NG-10-0104 | PMOguan | 30 | 27 | 14 |
| NG-10-0420 | PMOplus methyl | 29 | 27 | 25 |
| NG-10-0065 | PMOtri | 30 | 26 | 2 |
| NG-10-0607 | PMO-X | 30 | 25 | 19 |
| NG-10-0060 | PMOcp | 30 | 25 | 6 |
| NG-10-0162 | PMO-COCH$_2$SH | 30 | 25 | 8 |
| NG-10-0328 | diphenylacetyl | 30 | 25 | 20 |
| NG-10-0134 | PMOapnPMOtri | 30 | 23 | 2 |
| NG-10-0386 | PMO | 30 | 22 | 11 |
| NG-07-0064 | PMO-3'-trityl | 30 | 22 | 23 |
| NG-10-0059 | PMOcp | 30 | 22 | 9 |
| NG-10-0135 | PMOtri | 30 | 21 | 19 |
| NG-10-0168 | PMOapn PMOcys | 30 | 21 | 6 |
| NG-10-0113 | PMOapnPMOtri | 30 | 20 | 20 |
| NG-10-0385 | PMO | 30 | 20 | 32 |
| NG-10-0279 | PMO | 30 | 19 | 22 |
| NG-10-0055 | PMOplus disp | 30 | 17 | 11 |
| NG-10-0105 | PMOsucc | 30 | 16 | 4 |
| NG-10-0805 | PMO-X | 30 | 16 | 21 |
| NG-10-0811 | PMO-X | 32 | 16 | 6 |
| NG-10-0057 | PMOplus 3'-pol | 30 | 15 | 16 |
| NG-10-0625 | PMO-X | 28 | 15 | 11 |
| NG-10-0804 | Dimer | 35 | 15 | 11 |
| NG-10-0066 | PMOtri | 30 | 12 | 1 |
| NG-10-0280 | PMO disulfide | 30 | 12 | 14 |
| NG-10-0212 | PMOapn | 20 | 11 | 15 |
| NG-10-0156 | 3'-MeOtrityl | 30 | 10 | 22 |
| NG-10-0062 | PMOhex | 30 | 9 | 10 |
| NG-11-0043 | PMO-X | 30 | 9 | 16 |
| NG-10-0206 | PMOplus | 31 | 8 | 10 |

Example 28

Treatment of Transgenic eGFP Mice with Exemplary PMO Oligomers of the Invention

Experiments in support of the invention used an eGFP-based assay for in vivo antisense activity and was used to evaluate oligomers comprising the modified intersubunit linkages of the invention. The transgenic eGFP mouse model in which the eGFP-654 transgene, is expressed uniformly throughout the body has been described (Sazani, Gemignani et al. 2002). This model uses a splicing assay for activity in which the modified oligomers of the present invention block aberrant splicing and restore correct splicing of the modified enhanced green fluorescent protein (eGFP) pre-mRNA. In this approach, antisense activity of each oligomer is directly proportional to up-regulation of the eGFP reporter. As a result, the functional effects of the same oligomer can be monitored in almost every tissue. This is in contrast to oligomers targeted to genes whose expression is restricted to or is phenotypically relevant in only certain tissues. In the eGFP-654 mice, the pre-mRNA was readily detectable in all tissues although smaller amounts were found in the bone marrow, skin and brain. The level of translated eGFP is proportional to the potency of the antisense oligomers and their concentration at the site of action. RT-PCR of total RNA isolated from various tissues showed expression of eGFP-654 transcript in all tissues surveyed.

Figure 7A:
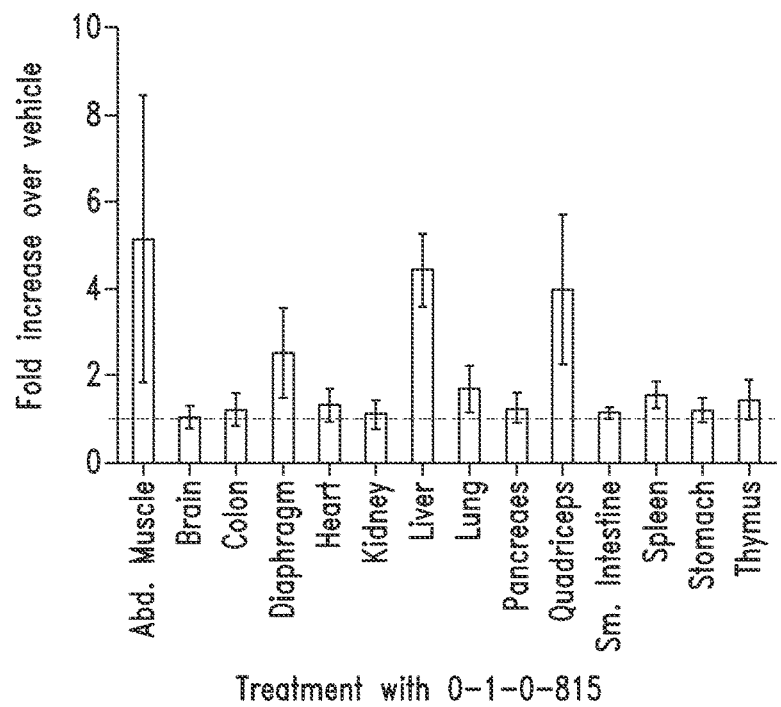
FIGS. 7A-7C provides results of reatment of transgenic eGFP mice with exemplary oligomers.
Figure 7B:
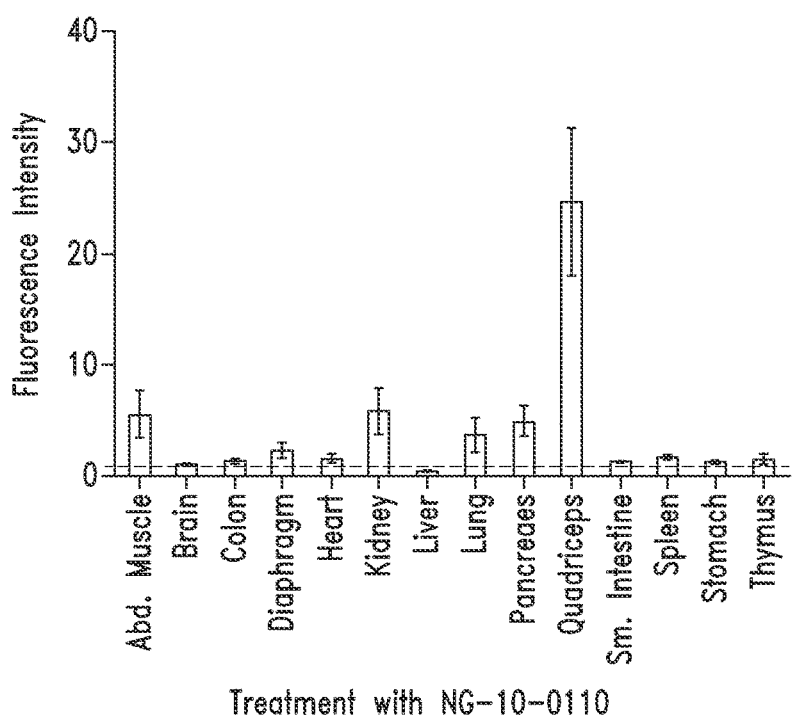
Figure 7C:
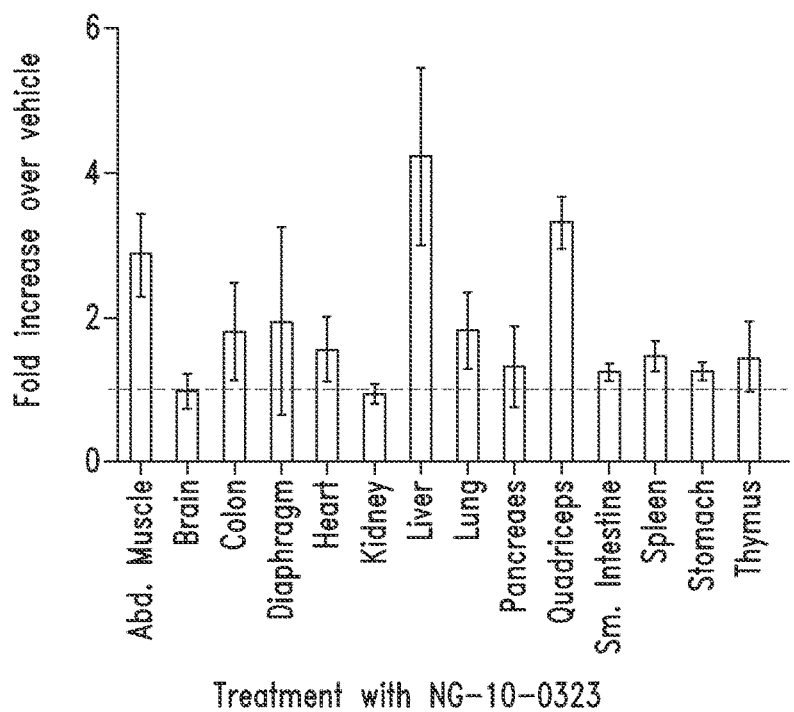

Tissues from eGFP-654 mice (n=6) treated with compound ranging from 5 to 150 mg/kg were collected 8 days post-dosing and frozen at −80° C. Tissues were thawed immediately prior to imaging on a GE Typhoon Trio, misted with PBS, and arrayed directly on the glass platen of the scanner. 50 micron scans to collect eGFP fluorescence were performed using the 488 nm excitation laser and 520 nm BP 40 emission filter with the focal plane at the platen surface. Tissue scans were analyzed using ImageQuant to determine average fluorescence across each tissue. Tissue fluorescence from 3-5 mice treated with vehicle only were averaged to yield an intrinsic background fluorescence measurement for each tissue type. Fold-fluorescence values of the corresponding tissues from compound-treated mice were calculated as the fraction of the vehicle tissue fluorescence. FIGS. 7B-C show the tissue specific activity in the eGFP-654 mouse model of two PMO containing exemplary intersubunit linkages of the invention, NG-10-0110 and NG-10-0323-, containing linkages b54 and b1, respectively. All of the oligomers tested are derived from the eGFP654 sequence (SEQ ID NO: 17). For comparison, results using a PMO having the same sequence, but lacking any intersubunit modifications is shown in FIG. 7A. NG-10-0110 (SEQ ID NO: 17) had high activity in quadriceps and poor activity in liver (FIG. 7B) whereas NG-10-0323 had improved liver activity and muscle delivery (FIG. 7C).

Figure 11:
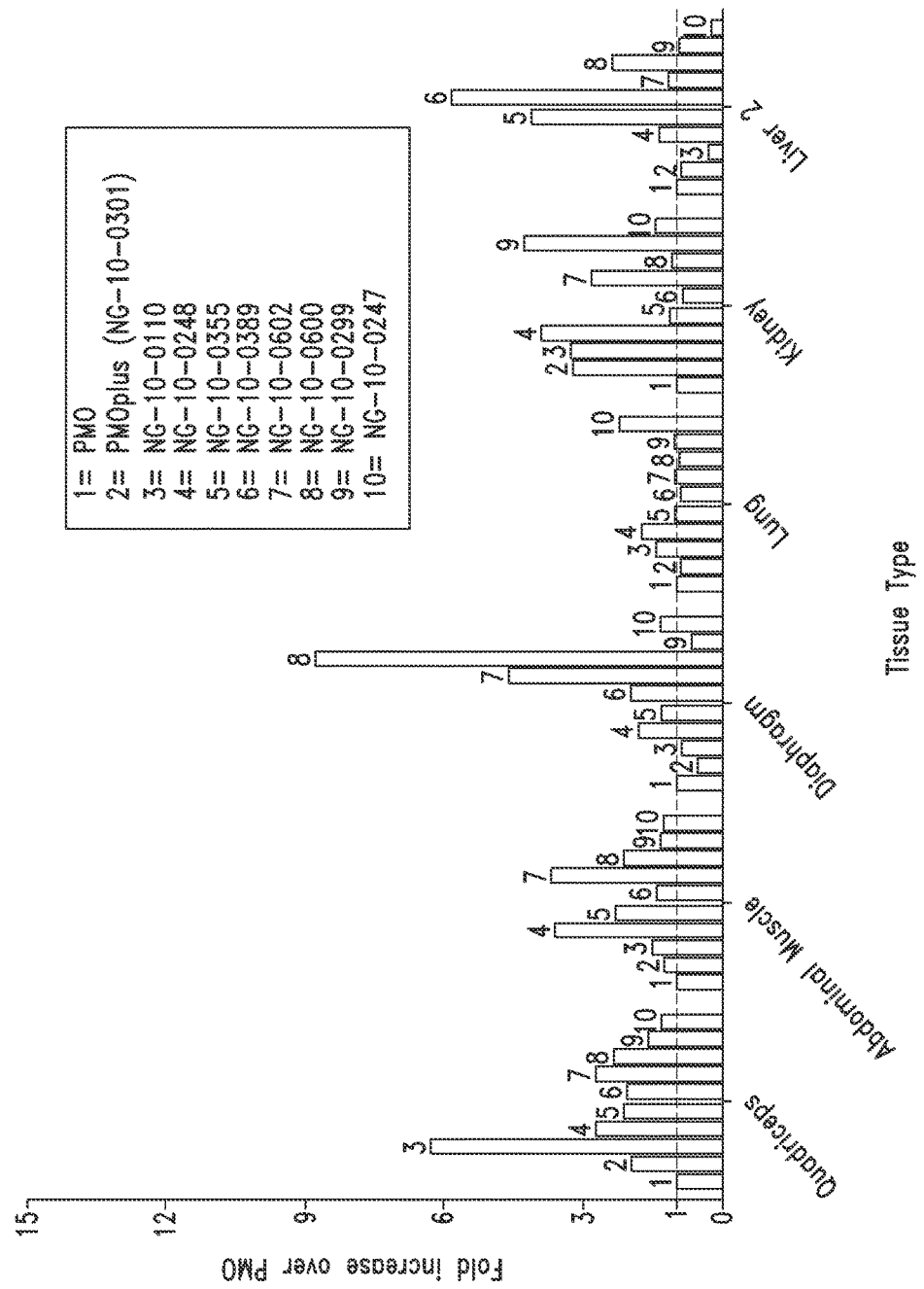
FIG. 11 is eGFP splice-correction activity data in various tissues from mice treated with exemplary oligomers compared to PMO and PMO+ oligomers.
Figure 12:
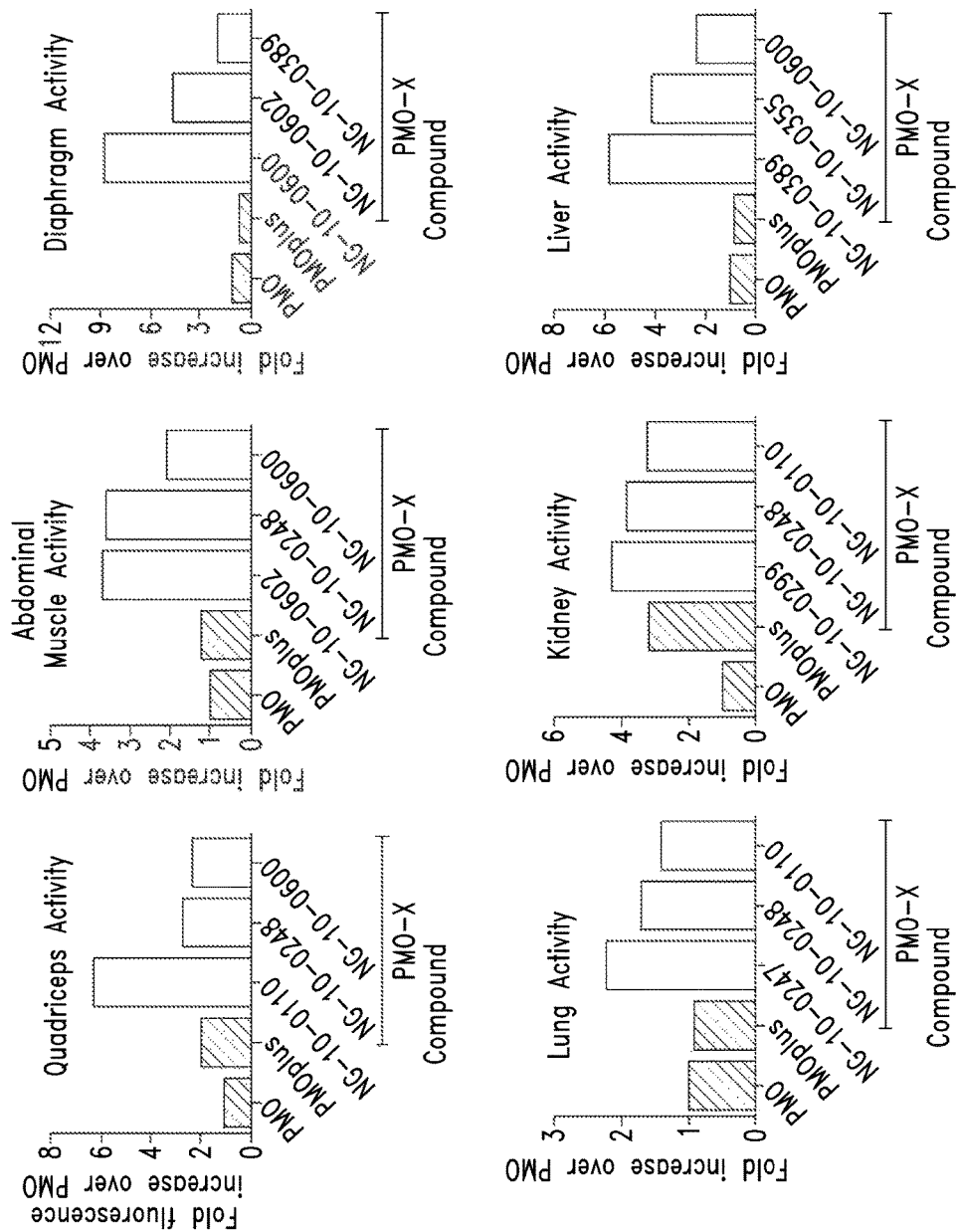
FIG. 12 shows a subset of eGFP splice-correction activity data in various tissues from mice treated with exemplary oligomers compared to PMO and PMO+ oligomers.

Additional examples in support of the invention included experiments using eGFP (SEQ ID NO:17) oligomers modified using the linkages and terminal groups of the invention. As shown in FIGS. 11 and 12, compared to PMO and PMOplus oligomers, several modified oligomers showed improved eGFP splice-correction activity in various tissues from mice treated as described above.

The specific PMO-X modifications of the compounds described in this example are shown below in Table 10.

TABLE 10

Sequences Used in Example 28 Showing Linkage Type

| NG-10-0110 | GC$^{guan}$T AT$^{guan}$T ACC T$^{guan}$TA ACC CAG |
|---|---|
| NG-10-0323 | GC$^{pyr}$T AT$^{pyr}$T ACC T$^{pyr}$TA ACC CAG |

TABLE 10-continued

Sequences Used in Example 28 Showing Linkage Type

| | |
|---|---|
| PMOplus; NG-10-0301 | GC+T AT+T ACC +TTA ACC CAG |
| NG-10-0248 | GCaT AaTaT ACC aTaTA ACC CAG |
| NG-10-0600 * | GCaT ATaT ACC TaTA ACC CAG |
| NG-10-0602 ** | GCpT ATpT ACC TpTA ACC CAG |
| NG-10-0389 | GCX ATX ACC TXA ACC CAG |
| NG-10-0247 | GCpT ApTpT ACC TpTA ACC CAG |
| NG-10-0299 | GCaT ATaT ACC TaTA ACC CAG |
| NG-10-0355 *** | GCaT ATaT ACC TaTA ACC CAG |

\* trimethyl glycine acylated product from NG-10-0299;
\*\* pT = PMOpyr methylated to quaternary amine from NG-10-0323;
X = PMOapn;
\*\*\* 3' trityl

Example 29

Treatment of Influenza A Virus Infected Cells with Exemplary PMO Oligomers of the Invention A series of PMO containing various modified intersubunit linkages was prepared and used to treat influenza A virus-infected cells in culture. The PMO and PMO containing the modified intersubunit linkages of the present inventions were all designed to target the viral M1/M2 segment at the AUG start codon and have one of two base sequences (SEQ ID NOs: 3 and 4). PMO with the modified intersubunit linkages of the present invention are listed in Table 4 and identified by the NG number designation in the Sequence Listing Table below. Inhibition of influenza A virus replication by antisense targeting of multiple sites within the M1/M2 segment is described in co-owned and co-pending U.S. application Ser. No. 12/945,081 which is incorporated herein by reference in its entirety. In addition to inhibition of translation by targeting the common M1/M2 AUG start site, splice donor and splice acceptor sites can also be targeted using compounds of the invention.

An alveolar murine macrophage cell line (ATCC; AMJ2-C11) was infected at 0.1 MOI with H1N1 (strain PR8) and 1 hour post-infection PMO were added. Cells were incubated at 35 degrees C. overnight. Viral supernatant was then taken and incubated with VNAR protease to release viral RNA. HA RNA was quantified by quantitative real-time PCR (qRT-PCR). Cells were washed, fixed, and permeabilized. M1 and M2 proteins were then probed with monoclonal antibodies for 30 min at 37 degrees C. Cells were washed and anti-mouse IgG conjugated with Alexa 646 was added for 15 min at room temperature. M1 and M2 were then assayed by flow cytometry. To determine M1 and M2 protein levels, the percent of M1 or M2 positive cells was multiplied by the mean flourescent intensity of M1 or M2. Each sample was then divided by the untreated control to generate the percent of M1 or M2 compared to untreated scramble controls.

Figure 8:
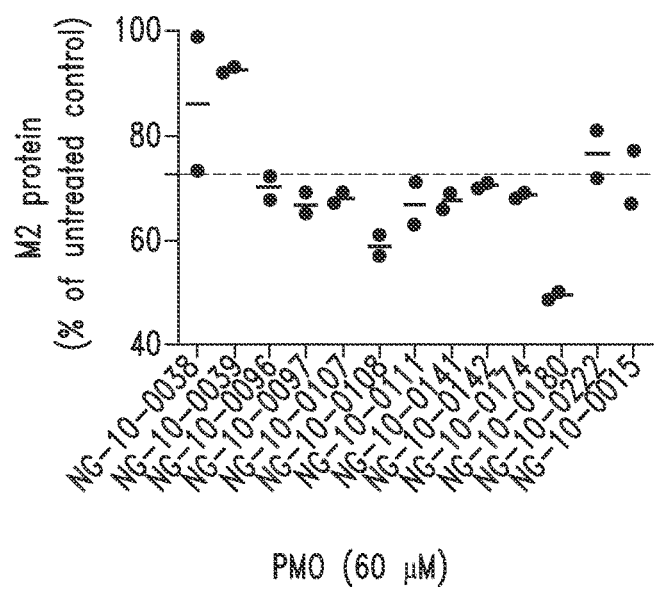
FIG. 8 shows reduction in viral M2 protein levels from cells treated with exemplary oligomers.

FIG. 8 shows the reduction in viral M2 protein levels from cells treated with various compounds of the disclosure. The flow cytometry method described above was used to determine relative M2 protein expression after treatment at 60 micromolar. The oligomers inhibited the production of the M2 protein to varying degrees with NG-10-180 (SEQ ID NO: 3) containing linkage b1 being the most active. Results using PMO without any intersubunit modifications is shown in FIG. 8 as NG-10-0015 (SEQ ID NO:3) for comparison.

Example 30

Treatment of Influenza A Virus Infected Mice In Vivo with Exemplary PMO Oligomers of the Invention Additional experiments in support of the invention were performed using Balb/c mice infected with the PR8 strain of influenza A. Mice were infected with 3.5 $TCID_{50}$ via an intranasal inoculation after being treated 4 hours prior with PMO-X compounds of the invention. In some experiments an additional dose of PMO-X was administered at 96 hr post-infection. All doses consisted of 100 micrograms of test compound in 50 microliters of PBS and were administered by intranasal insufflation. The weight of the animals were monitored daily and was used as a clinical endpoint for antiviral drug activity. At day 7 post-infection the animals were sacrificed and lungs were harvested for viral load determinations using the qRT-PCR method described above in Example 29.

$TCID_{50}$ determinations were made using half-log serial dilutions of the lung homogenates and plated onto AMJ-C12 macrophage cells. After 24 hr at 35 degrees C., the media was changed and incubated for an additional 72 h at 35 degrees C. 50 mL of a solution of 0.5% chicken RBC in PBS was added and incubated for 1 h at 4 degrees C. Hemagglutination pattern was read and $TCID_{50}$ were calculated using the Reed and Muench method. TCID50 values were then normalized to input tissue weight.

Figure 9:
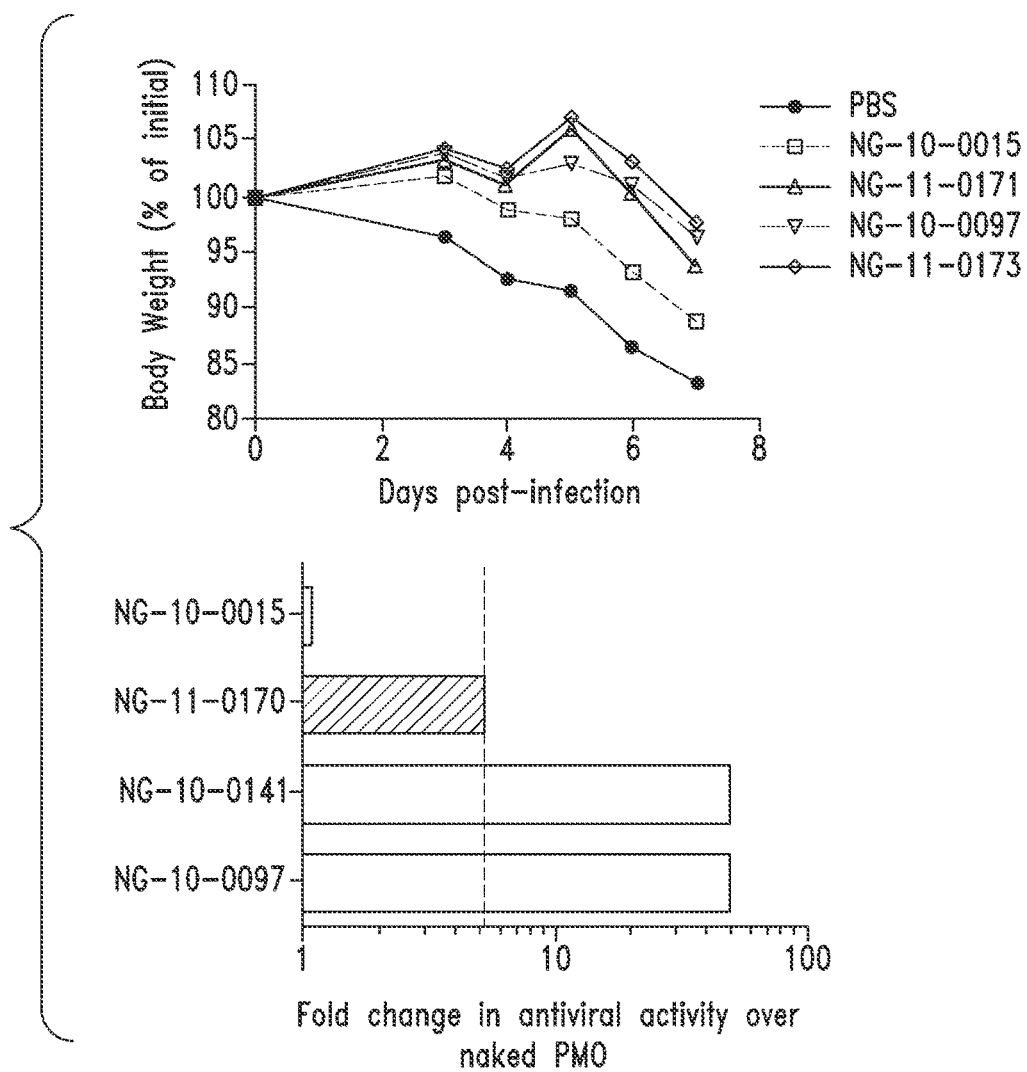
FIG. 9 shows antiviral activity and weight loss in mice treated with exemplary oligomers.

As shown in FIG. 9, PMO-X compounds show increased antiviral activity and decreased weight loss compared to a PMOplus compound after H1N1 infection. Balb/c mice (n=4) were infected with H1N1 and given a single 100 microgram dose of PMO 4 hours prior to infection. Mice were weighed daily and percent weight loss was determined from pre-infection weight. Lungs were harvested day 7 post-infection and assayed for viral load by $TCID_{50}$. Results are presented as the fold increase in antiviral activity over naked PMO. This experiment shows approximately 50-fold increased antiviral activity of two PMO-X compounds (NG-10-0097 and NG-11-0173; SEQ ID NO:3) compared to un-modified PMO (NG-10-0015; SEQ ID NO: 3) and approximately 10-fold higher activity compared to a PMOplus compound (NG-11-0170; SEQ ID NO: 3).

Figure 10:
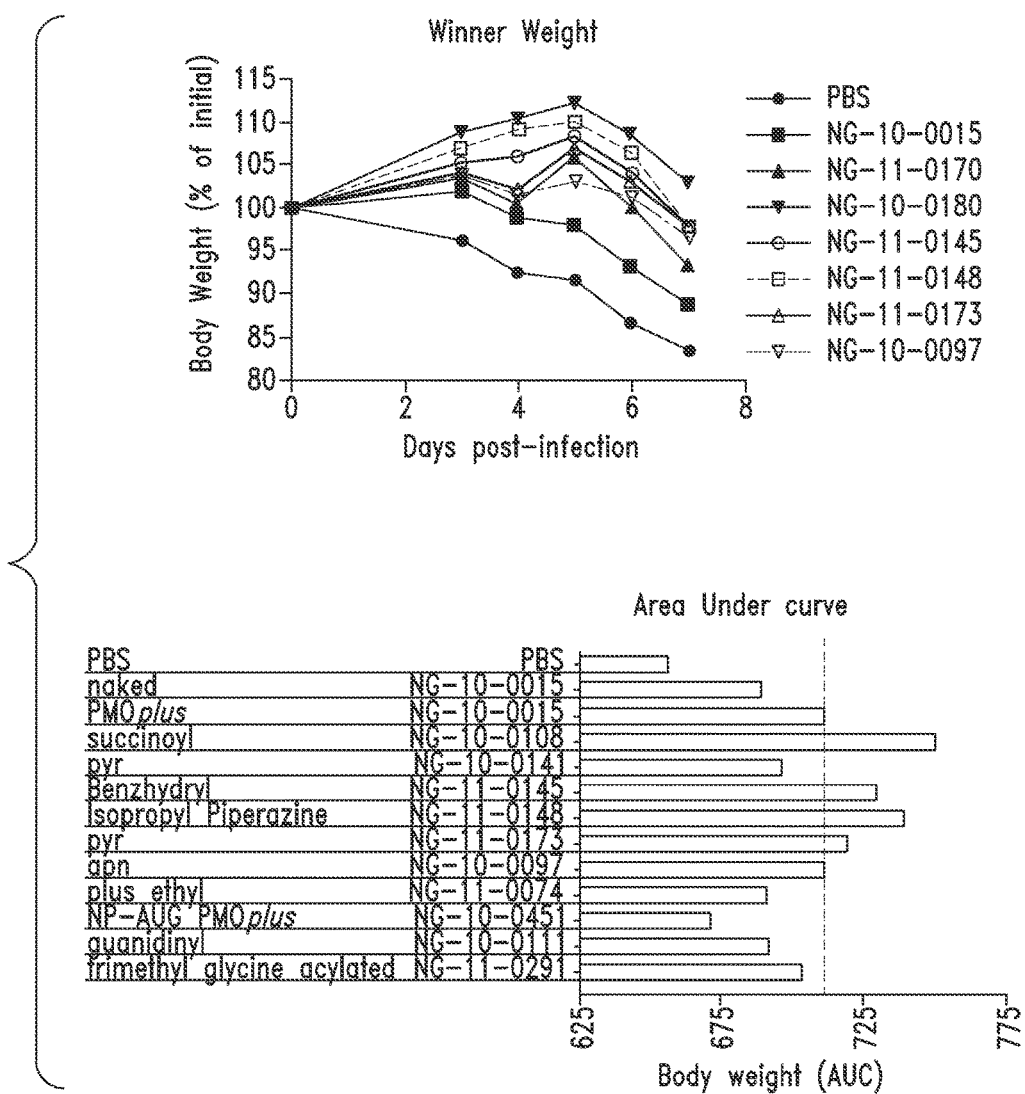
FIG. 10 provides body weight data of mice treated with exemplary oligomers.

FIG. 10 shows a similar experiment to that described for FIG. 9 using body weight as a clinical measurement of antiviral activity. Relative to the PMOplus compound (NG-11-0170) several PMO-X compounds showed superior results including compounds containing succinoyl (NG-10-0108), isopropyl piperazine (NG-11-0148) and pyrollidone (NG-11-0173) linkages and a PMOplus compound modified with a 3' terminal benzhydryl group (NG-11-0145).

Example 31

Preparation of an Oligonucleotide Analogue Comprising a Modified Terminal Group

To a solution of a 25-mer PMO containing a free 3'-end (27.7 mg, 3.226 μmol) in DMSO (300 μL) was added farnesyl bromide(1.75 μl, 6.452 μmol) and diisopropylethylamine (2.24 μL, 12.9 μmol). The reaction mixture was stirred at room temperature for 5 hours. The crude reaction mixture was diluted with 10 mL of 1% aqueous NH$_4$OH, and then loaded onto a 2 mL Amberchrome CG300M column. The column was then rinsed with 3 column volumes of water, and the product was eluted with 6 mL of 1:1 acetonitrile and water (v/v). The solution was then lyophilized to obtain the title compound as a white solid.

Example 32

Preparation of Morpholino Oligomers

Preparation of trityl piperazine phenyl carbamate 35 (see FIG. 3): To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO3. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 38 from compound 36. Introduction of the activated "Tail" onto the disulfide anchor-resin was performed in NMP by the procedure used for incorporation of the subunits during solid phase synthesis.

Preparation of the Solid Support for Synthesis of Morpholino Oligomers: This procedure was performed in a silanized, jacketed peptide vessel (custom made by Chem-Glass, NJ, USA) with a coarse porosity (40-60 μm) glass frit, overhead stirrer, and 3-way Teflon stopcock to allow N2 to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 (see FIG. 4) was dried under a N2 stream for 1-3 hr and then under vacuum to constant weight (+2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient ($\varepsilon$: 41 µmol-1 cm-1) and resin weight. The assay is performed in triplicate and an average loading calculated.

The resin loading procedure in this example will provide resin with a loading of approximately 500 µmol/g. A loading of 300-400 in mol/g was obtained if the disulfide anchor incorporation step is performed for 24 hr at room temperature.

Tail loading: Using the same setup and volumes as for the preparation of aminomethylpolystyrene-disulfide resin, the Tail can be introduced into the molecule. For the coupling step, a solution of 38 (0.2 M) in NMP containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:

Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
|---|---|---|---|
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 µL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Initial Oligomer Isolation: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M $H_3PO_4$ to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% NH4OH/ 80% acetonitrile; 0.5M NaOH/20% ethanol; water; 50 mM H3PO4/80% acetonitrile; water; 0.5 NaOH/20% ethanol; water; 0.28% NH4OH.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM KH2PO4 25% acetonitrile at pH=3.5 (buffer A) and 25 mM KH2PO4 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Purification of Morpholino Oligomers by Cation Exchange Chromatography: The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

TABLE 11

Sequence Listing

| Name | Sequence (5' to 3') | SEQ ID NO |
|---|---|---|
| Dengue | CGGTCCACGTAGACTAACAACT | 1 |
| JEV | GAAGTTCACACAGATAAACTTCT | 2 |
| M1/M2AUG.20.22 | CGGTTAGAAGACTCATCTTT | 3 |
| M1/M2AUG.25.26 | TTTCGACATCGGTTAGAAGACTCAT | 4 |
| NP-AUG | GAGACGCCATGATGTGGATGTC | 5 |
| Picornavirus | GAAACACGGACACCCAAAGTAGT | 6 |
| Dengue 3'-CS | TCCCAGCGTCAATATGCTGTTT | 7 |
| Arenaviruses | GCCTAGGATCCACGGTGCGC | 8 |
| RSV-L target | GGGACAAAATGGATCCCATTATTAATGGAAATTCTGCTAA | 9 |
| RSV-AUG-2 | TAATGGGATCCATTTTGTCCC | 10 |
| RSV-AUG3 | AATAATGGGATCCATTTTGTCCC | 11 |
| RSV-AUG4 | CATTAATAATGGGATCCATTTTGTCCC | 12 |
| RSV-AUG5 | GAATTTCCATTAATAATGGGATCCATTTTG | 13 |
| RSV-AUG6 | CAGAATTTCCATTAATAATGGGATCCATT | 14 |
| M23D | GGCCAAACCTCGGCTTACCTGAAAT | 15 |
| AVI-5225 | GGCCAAACCTCGGCTTACCTGAAAT - RAhxRRBRRAhxRRBRAhxB | 16/79 |
| eGFP654 | GCTATTACCTTAACCCAG | 17 |
| huMSTN target | GAAAAAGATTATATTGATTTTAAAATCATGCAAAAAC TGCAACTCTGTGTT | 18 |
| muMSTN25-104 | CATACATTTGCAGTTTTTGCATCAT | 19 |
| muMSTN25-183 | TCATTTTTAAAAATCAGCACAATCTT | 20 |

TABLE 11-continued

Sequence Listing

| Name | Sequence (5' to 3') | SEQ ID NO |
|---|---|---|
| muMSTN25-194 | CAGTTTTTGCATCATTTTTAAAAATC | 21 |
| Exon44-A | GATCTGTCAAATCGCCTGCAGGTAA | 22 |
| Exon44-B | AAACTGTTCAGCTTCTGTTAGCCAC | 23 |
| Exon44-C | TTGTGTCTTTCTGAGAAACTGTTCA | 24 |
| Exon45-A | CTGACAACAGTTTGCCGCTGCCCAA | 25 |
| Exon45-B | CCAATGCCATCCTGGAGTTCCTGTAA | 26 |
| Exon45-C | CATTCAATGTTCTGACAACAGTTTGCCGCT | 27 |
| Exon50-A | CTTACAGGCTCCAATAGTGGTCAGT | 28 |
| Exon50-B | CCACTCAGAGCTCAGATCTTCTAACTTCC | 29 |
| Exon50-C | GGGATCCAGTATACTTACAGGCTCC | 30 |
| Exon51-A | ACATCAAGGAAGATGGCATTTCTAGTTTGG | 31 |
| Exon51-B | CTCCAACATCAAGGAAGATGGCATTTCTAG | 32 |
| Exon51-C | GAGCAGGTACCTCCAACATCAAGGAA | 33 |
| Exon53-A | CTGAAGGTGTTCTTGTACTTCATCC | 34 |
| Exon53-B | TGTTCTTGTACTTCATCCCACTGATTCTGA | 35 |
| SMN2-A | CTTTCATAATGCTGGCAG | 36 |
| SMN2-B | CATAATGCTGGCAG | 37 |
| SMN2-C | GCTGGCAG | 38 |
| CAG 9 mer | CAG CAG CAG | 39 |
| CAG 12 mer | CAG CAG CAG CAG | 40 |
| CAG 15 mer | CAG CAG CAG CAG CAG | 41 |
| CAG 18 mer | CAG CAG CAG CAG CAG CAG | 42 |
| AGC 9 mer | AGC AGC AGC | 43 |
| AGC 12 mer | AGC AGC AGC AGC | 44 |
| AGC 15 mer | AGC AGC AGC AGC AGC | 45 |
| AGC 18 mer | AGC AGC AGC AGC AGC AGC | 46 |
| GCA 9 mer | GCA GCA GCA | 47 |
| GCA 12 mer | GCA GCA GCA GCA | 48 |
| GCA 15 mer | GCA GCA GCA GCA GCA | 49 |
| GCA 18 mer | GCA GCA GCA GCA GCA GCA | 50 |
| AGC 25 mer | AGC AGC AGC AGC AGC AGC AGC AGC A | 51 |
| CAG 25 mer | CAG CAG CAG CAG CAG CAG CAG CAG C | 52 |
| CAGG 9 mer | CAG GCA GGC | 53 |
| CAGG 12 mer | CAG GCA GGC AGG | 54 |
| CAGG 24 mer | CAG GCA GGC AGG CAG GCA GGC AGG | 55 |

Arginine-Rich Cell Penetrating Peptides

| rTAT | RRRQRRKKR | 56 |
| Tat | RKKRRQRRR | 57 |

TABLE 11-continued

Sequence Listing

| Name | Sequence (5' to 3') | SEQ ID NO |
|---|---|---|
| $R_9F_2$ | RRRRRRRRRFF | 58 |
| $R_5F_2R_4$ | RRRRRFFRRRR | 59 |
| $R_4$ | RRRR | 60 |
| $R_5$ | RRRRR | 61 |
| $R_6$ | RRRRRR | 62 |
| $R_7$ | RRRRRRR | 63 |
| $R_8$ | RRRRRRRR | 64 |
| $R_9$ | RRRRRRRRR | 65 |
| $(RAhxR)_4$; (P007) | RAhxRRAhxRRAhxRRAhxR | 66 |
| $(RAhxR)_5$; (CP04057) | RAhxRRAhxRRAhxRRAhxRRAhxR | 67 |
| $(RAhxRRBR)_2$; (CP06062) | RAhxRRBRRAhxRRBR | 68 |
| $(RAR)_4F_2$ | RARRARRARRARFFC | 69 |
| $(RGR)_4F_2$ | RGRRGRRGRRGRFFC | 70 |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An oligomer comprising a backbone, the backbone comprising a sequence of morpholino ring structures joined by intersubunit linkages of type (A), (B), or combinations thereof, wherein each morpholino ring structure supports a base-pairing moiety, such that the oligomer compound can bind in a sequence-specific manner to a target nucleic acid, and wherein the oligomer comprises a 3' terminus, a 5' terminus and has the following structure (XVII):

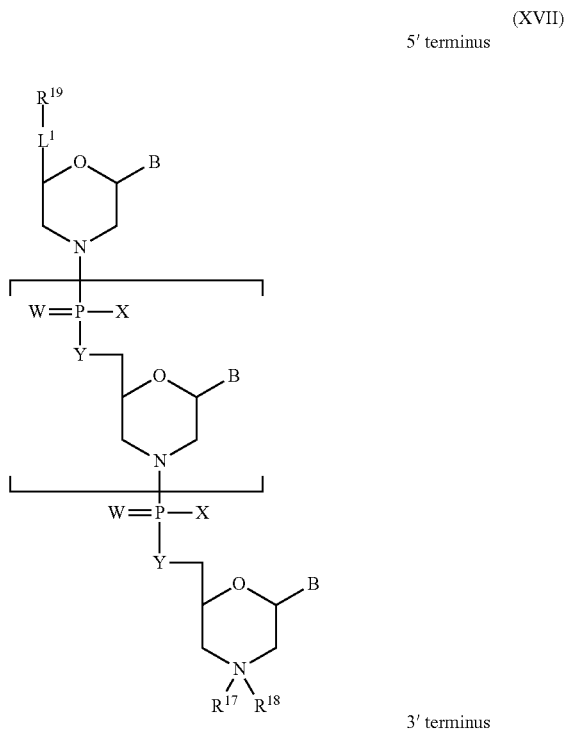

or a salt thereof, and
wherein for linkage (A):
W is, at each occurrence, independently S or O;
X is, at each occurrence, independently —N(CH$_3$)$_2$, —NR$^1$R$^2$, —OR$^3$ or;

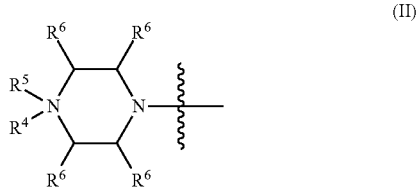

Y is, at each occurrence, independently O or —NR$^2$,
R$^1$ is, at each occurrence, independently hydrogen or methyl;
R$^2$ is, at each occurrence, independently hydrogen or -LNR$^4$R$^5$R$^7$;
R$^3$ is, at each occurrence, independently hydrogen or C$_1$-C$_6$ alkyl;
R$^4$ is, at each occurrence, independently hydrogen, methyl, —C(=NH)NH$_2$, —Z-L-NHC(=NH)NH$_2$ or —[C(O)CHR'NH]$_m$H, where Z is carbonyl (C(O)) or a direct bond, R' is a side chain of a naturally occurring amino acid or a one- or two-carbon homolog thereof, and m is 1 to 6,
R$^5$ is, at each occurrence, independently hydrogen, methyl or an electron pair;
R$^6$ is, at each occurrence, independently hydrogen or methyl;
R$^7$ is, at each occurrence, independently hydrogen C$_1$-C$_6$ alkyl or C$_1$-C$_6$ alkoxyalkyl;
L is an optional linker up to 18 atoms in length comprising alkyl, alkoxy or alkylamino groups, or combinations thereof; and
wherein for linkage (B):
W is, at each occurrence, independently S or 0;
X is, at each occurrence, independently —NR$^8$R$^9$ or —OR$^3$; and
Y is, at each occurrence, independently O or —NR$^{10}$,
R$^8$ is, at each occurrence, independently hydrogen or C$_2$-C$_{12}$ alkyl;
R$^9$ is, at each occurrence, independently hydrogen, C$_1$-C$_{12}$ alkyl, C$_1$-C$_{12}$ aralkyl or aryl;
R$^{10}$ is, at each occurrence, independently hydrogen, C$_1$-C$_{12}$ alkyl or -LNR$^4$R$^5$R$^7$;
wherein R$^8$ and R$^9$ may join to form a 5-18 membered optionally substituted mono or bicyclic heterocycle or R$^8$, R$^9$ or R$^3$ may join with R$^{10}$ to form a 5-7 membered heterocycle, and wherein when X is 4-piperazino, X has the following structure (Ill):

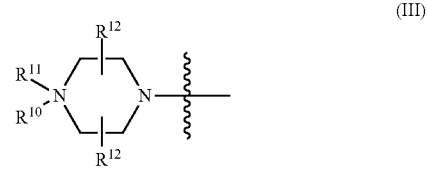

wherein:
R$^{10}$ is, at each occurrence, independently C$_2$-C$_{12}$ alkyl, C$_1$-C$_{12}$ aminoalkyl, C$_1$-C$_{12}$ alkylcarbonyl, aryl, heteroaryl or heterocyclyl; and
R$^{11}$ is, at each occurrence, independently an electron pair, hydrogen or C$_1$-C$_{12}$ alkyl;
R$^{12}$ is, at each occurrence, independently, hydrogen, C$_1$-C$_{12}$ alkyl, C$_1$-C$_{12}$ aminoalkyl, —NH$_2$, —CONH$_2$, —NR$^{13}$R$^{14}$, —NR$^{13}$R$^{14}$R$^{15}$, alkylcarbonyl, —CN, trifluoromethyl, amidyl, amidinyl, amidinylalkyl, amidinylalkylcarbonyl, guanidinyl, guanidinylalkyl, guanidinylalkylcarbonyl, cholate, deoxycholate, aryl, heteroaryl, heterocycle, —SR$^{13}$ or C$_1$-C$_{12}$ alkoxy, wherein R$^{13}$, R$^{14}$ and R$^{15}$ are, at each occurrence, independently C$_1$-C$_{12}$ alkyl; and
R$^{17}$ is, at each occurrence, independently absent, hydrogen or C$_1$-C$_6$ alkyl;
R$^{18}$ and R$^{19}$ are, at each occurrence, independently absent, hydrogen, a cell-penetrating peptide, a natural or non-natural amino acid, C$_2$-C$_{30}$ alkylcarbonyl, —C(=O)OR$^{21}$ or R$^{20}$;
R$^{21}$ is C$_1$-C$_{30}$ alkyl comprising one or more oxygen or hydroxyl moieties or combinations thereof;
each R$^{22}$ is independently C$^6$-C$^{12}$ aryloxy; and
B is, at each occurrence, independently a base-pairing moiety;
L$^1$ is an optional linker up to 18 atoms in length comprising bonds selected from alkyl, hydroxyl, alkoxy, alkylamino, amide, ester, disulfide, carbonyl, carbamate, phosphorodiamidate, phosphoroamidate, phosphorothioate, piperazine and phosphodiester;

x is an integer of 0 or greater; and wherein at least one of $R^{18}$ or $R^{19}$ is $R^{20}$ and provided that both of $R^{17}$ and $R^{18}$ are not absent;

wherein if $R^{18}$ is $R^{20}$, $R^{20}$ is, at each occurrence, guanidinyl, heterocyclyl, $C_1$-$C_{30}$ alkyl, $C_3$-$C_8$ cycloalkyl, $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)($R^{22}$)$_2$; or wherein if $R^{19}$ is $R^{20}$, $R^{20}$ is, at each occurrence, guanidinyl, heterocyclyl, $C_1$-$C_{30}$ alkyl, $C_3$-$C_8$ cycloalkyl, $C_6$-$C_{30}$ aryl, $C_7$-$C_{30}$ aralkyl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)($R^{22}$)$_2$.

2. The oligomer of claim 1, wherein $R^{20}$ is $C_7$-$C_{30}$ arylcarbonyl.

3. The oligomer of claim 1, wherein $R^{20}$ is $C_7$-$C_{30}$ aralkylcarbonyl.

4. The oligomer of claim 1, wherein $R^{20}$ is $C_6$-$C_{30}$ aryl.

5. The oligomer of claim 1, wherein $R^{20}$ is $C_1$-$C_{30}$ alkyl.

6. The oligomer of claim 1, wherein $R^{20}$ is $C_3$-$C_{30}$ alkylcarbonyl.

7. The oligomer of claim 1, wherein $R^{20}$ is —C(=O)(CH$_2$)$_p$SH or —C(=O)(CH$_2$)$_p$SSHet, wherein p is an integer from 3 to 6 and Het is a heteroaryl.

8. The oligomer of claim 1, wherein $R^{20}$ is $C_3$-$C_8$ cycloalkylcarbonyl.

9. The oligomer of claim 1, wherein $R^{20}$ is —C(=O)(CH$_2$)$_n$CO$_2$H, where n is 3 to 6.

10. The oligomer of claim 1, wherein $R^{20}$ is guanidinyl.

11. The oligomer of claim 1, wherein $R^{19}$ is —C(=O)OR$^{21}$.

12. The oligomer of claim 1, wherein $R^{20}$ is —P(=O)(R$^{22}$)$_2$.

13. The oligomer of claim 1, wherein $R^{18}$ is trimethylglycine.

14. The oligomer of claim 1, wherein $R^{18}$ is a cell-penetrating peptide and $R^{19}$ is $R^{20}$.

15. The oligomer of claim 1, wherein $R^{19}$ is a cell-penetrating peptide and $R^{18}$ is $R^{20}$.

16. The oligomer of claim 1, wherein $L^1$ has the following structure (XXIX):

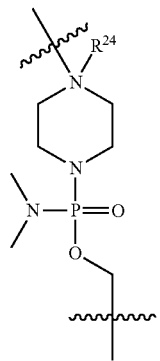

(XXIX)

wherein $R^{24}$ is absent, H or $C_1$-$C_6$ alkyl.

17. The oligomer of claim 1, wherein $R^{29}$ has the following structure (XXX):

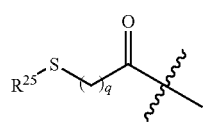

(XXX)

wherein $R^{25}$ is hydrogen or —SR$^{26}$, wherein $R^{26}$ is hydrogen, $C_1$-$C_{30}$ alkyl, heterocyclyl, aryl or heteroaryl, and q is an integer from 3 to 6.

18. The oligomer of claim 1, wherein $R^{19}$ has the following structure:

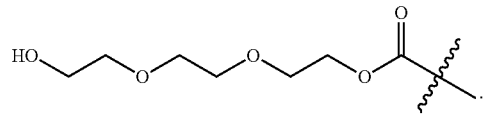 [SMILES: *C(=O)OCCOCCOCCO]

19. The oligomer of claim 1, wherein $R^{20}$ has one of the following structures:

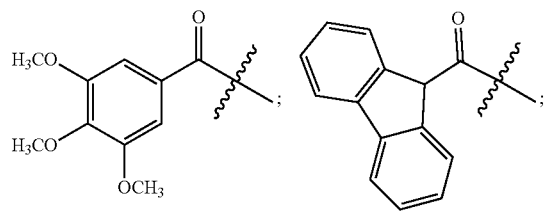

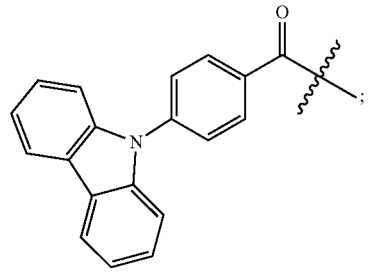

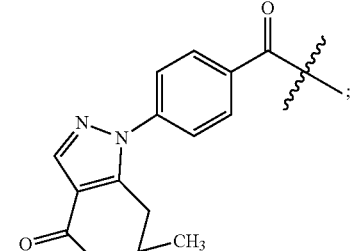

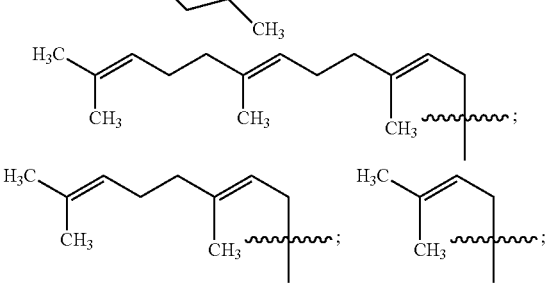

-continued

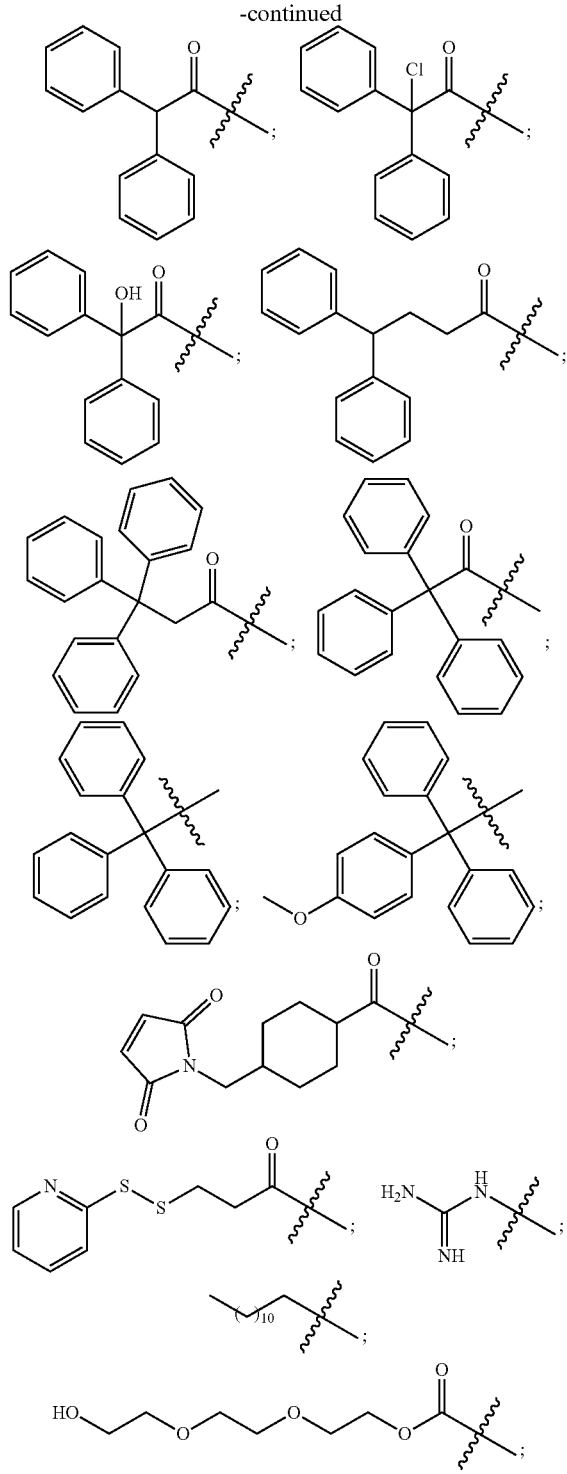

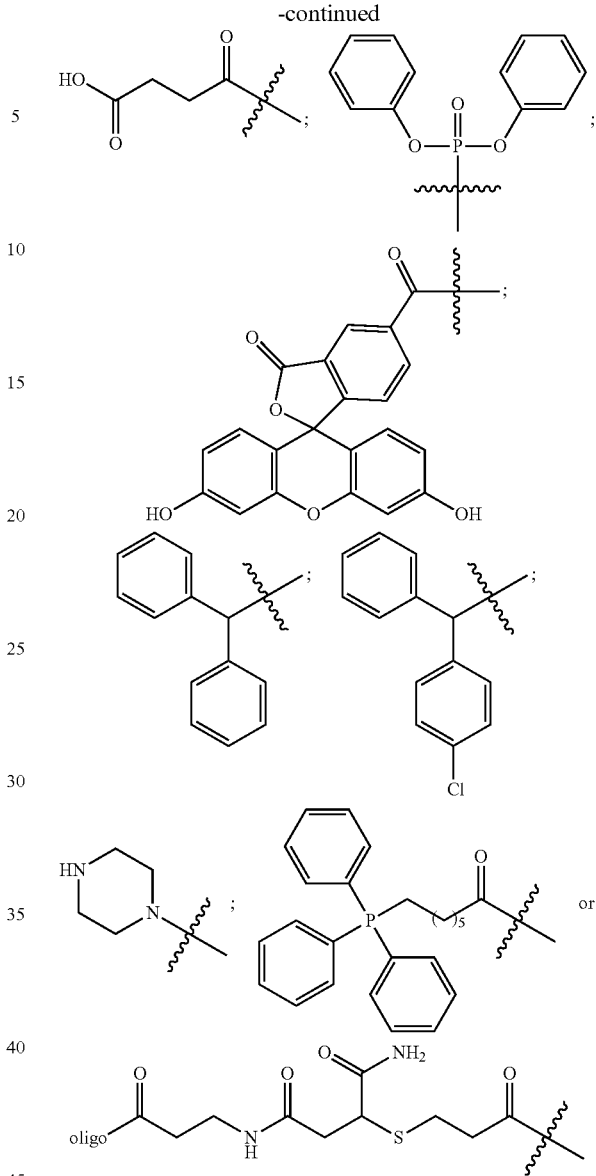

where oligo represents a further oligomer.

20. A composition comprising the oligomer of claim 1 and a pharmaceutically acceptable vehicle.

21. A method of treating a viral infection, a neuromuscular disease, a bacterial infection, inflammation or polycystic kidney disease in a subject, the method comprising administering a therapeutically effective amount of an oligomer of claim 1 to a subject in need thereof.

* * * * *

SEQUENCE LISTING

```
<160> NUMBER OF SEQ ID NOS: 88

<210> SEQ ID NO 1
<211> LENGTH: 22
<212> TYPE: DNA
<213> ORGANISM: Artificial Sequence
<220> FEATURE:
<223> OTHER INFORMATION: Antisense oligomer

<400> SEQUENCE: 1
cggtccacgt agactaacaa ct                                              22

<210> SEQ ID NO 2
<211> LENGTH: 23
<212> TYPE: DNA
<213> ORGANISM: Artificial Sequence
<220> FEATURE:
<223> OTHER INFORMATION: Antisense oligomer

<400> SEQUENCE: 2
gaagttcaca cagataaact tct                                             23

<210> SEQ ID NO 3
<211> LENGTH: 20
<212> TYPE: DNA
<213> ORGANISM: Artificial Sequence
```

```
<220> FEATURE:
<223> OTHER INFORMATION: Antisense oligomer

<400> SEQUENCE: 3
cggttagaag actcatcttt                                            20

<210> SEQ ID NO 4
<211> LENGTH: 25
<212> TYPE: DNA
<213> ORGANISM: Artificial Sequence
<220> FEATURE:
<223> OTHER INFORMATION: Antisense oligomer

<400> SEQUENCE: 4
tttcgacatc ggttagaaga ctcat                                      25

<210> SEQ ID NO 5
<211> LENGTH: 22
<212> TYPE: DNA
<213> ORGANISM: Artificial Sequence
<220> FEATURE:
<223> OTHER INFORMATION: Antisense oligomer

<400> SEQUENCE: 5
gagacgccat gatgtggatg tc                                         22

<210> SEQ ID NO 6
<211> LENGTH: 23
<212> TYPE: DNA
<213> ORGANISM: Artificial Sequence
<220> FEATURE:
<223> OTHER INFORMATION: Antisense oligomer

<400> SEQUENCE: 6
gaaacacgga cacccaaagt agt                                        23

<210> SEQ ID NO 7
<211> LENGTH: 22
<212> TYPE: DNA
<213> ORGANISM: Artificial Sequence
<220> FEATURE:
<223> OTHER INFORMATION: Antisense oligomer

<400> SEQUENCE: 7
tcccagcgtc aatatgctgt tt                                         22

<210> SEQ ID NO 8
<211> LENGTH: 20
<212> TYPE: DNA
<213> ORGANISM: Artificial Sequence
<220> FEATURE:
<223> OTHER INFORMATION: Antisense oligomer

<400> SEQUENCE: 8
gcctaggatc cacggtgcgc                                            20

<210> SEQ ID NO 9
<211> LENGTH: 40
<212> TYPE: DNA
<213> ORGANISM: Artificial Sequence
<220> FEATURE:
<223> OTHER INFORMATION: Antisense oligomer

<400> SEQUENCE: 9
gggacaaaat ggatcccatt attaatggaa attctgctaa                      40
```

```
<210> SEQ ID NO 10
<211> LENGTH: 21
<212> TYPE: DNA
<213> ORGANISM: Artificial Sequence
<220> FEATURE:
<223> OTHER INFORMATION: Antisense oligomer

<400> SEQUENCE: 10
taatgggatc cattttgtcc c                                               21

<210> SEQ ID NO 11
<211> LENGTH: 23
<212> TYPE: DNA
<213> ORGANISM: Artificial Sequence
<220> FEATURE:
<223> OTHER INFORMATION: Antisense oligomer

<400> SEQUENCE: 11
aataatggga tccattttgt ccc                                             23

<210> SEQ ID NO 12
<211> LENGTH: 27
<212> TYPE: DNA
<213> ORGANISM: Artificial Sequence
<220> FEATURE:
<223> OTHER INFORMATION: Antisense oligomer

<400> SEQUENCE: 12
cattaataat gggatccatt ttgtccc                                         27

<210> SEQ ID NO 13
<211> LENGTH: 30
<212> TYPE: DNA
<213> ORGANISM: Artificial Sequence
<220> FEATURE:
<223> OTHER INFORMATION: Antisense oligomer

<400> SEQUENCE: 13
gaatttccat taataatggg atccattttg                                      30

<210> SEQ ID NO 14
<211> LENGTH: 29
<212> TYPE: DNA
<213> ORGANISM: Artificial Sequence
<220> FEATURE:
<223> OTHER INFORMATION: Antisense oligomer

<400> SEQUENCE: 14
cagaatttcc attaataatg ggatccatt                                       29

<210> SEQ ID NO 15
<211> LENGTH: 25
<212> TYPE: DNA
<213> ORGANISM: Artificial Sequence
<220> FEATURE:
<223> OTHER INFORMATION: Antisense oligomer

<400> SEQUENCE: 15
ggccaaacct cggcttacct gaaat                                           25

<210> SEQ ID NO 16
<211> LENGTH: 25
<212> TYPE: DNA
<213> ORGANISM: Artificial Sequence
<220> FEATURE:
<223> OTHER INFORMATION: Antisense oligomer
```

```
<400> SEQUENCE: 16
ggccaaacct cggcttacct gaaat                                           25

<210> SEQ ID NO 17
<211> LENGTH: 18
<212> TYPE: DNA
<213> ORGANISM: Artificial Sequence
<220> FEATURE:
<223> OTHER INFORMATION: Antisense oligomer

<400> SEQUENCE: 17
gctattacct taacccag                                                   18

<210> SEQ ID NO 18
<211> LENGTH: 52
<212> TYPE: DNA
<213> ORGANISM: Artificial Sequence
<220> FEATURE:
<223> OTHER INFORMATION: Antisense oligomer

<400> SEQUENCE: 18
gaaaaaagat tatattgatt ttaaaatcat gcaaaaactg caactctgtg tt             52

<210> SEQ ID NO 19
<211> LENGTH: 25
<212> TYPE: DNA
<213> ORGANISM: Artificial Sequence
<220> FEATURE:
<223> OTHER INFORMATION: Antisense oligomer

<400> SEQUENCE: 19
catacatttg cagttttgc atcat                                            25

<210> SEQ ID NO 20
<211> LENGTH: 26
<212> TYPE: DNA
<213> ORGANISM: Artificial Sequence
<220> FEATURE:
<223> OTHER INFORMATION: Antisense oligomer

<400> SEQUENCE: 20
tcatttttaa aaatcagcac aatctt                                          26

<210> SEQ ID NO 21
<211> LENGTH: 26
<212> TYPE: DNA
<213> ORGANISM: Artificial Sequence
<220> FEATURE:
<223> OTHER INFORMATION: Antisense oligomer

<400> SEQUENCE: 21 cagttttgc atcattttta aaaatc                                           26

<210> SEQ ID NO 22
<211> LENGTH: 25
<212> TYPE: DNA
<213> ORGANISM: Artificial Sequence
<220> FEATURE:
<223> OTHER INFORMATION: Antisense oligomer

<400> SEQUENCE: 22
gatctgtcaa atcgcctgca ggtaa                                           25
```

```
<210> SEQ ID NO 23
<211> LENGTH: 25
<212> TYPE: DNA
<213> ORGANISM: Artificial Sequence
<220> FEATURE:
<223> OTHER INFORMATION: Antisense oligomer

<400> SEQUENCE: 23
aaactgttca gcttctgtta gccac                                         25

<210> SEQ ID NO 24
<211> LENGTH: 25
<212> TYPE: DNA
<213> ORGANISM: Artificial Sequence
<220> FEATURE:
<223> OTHER INFORMATION: Antisense oligomer

<400> SEQUENCE: 24
ttgtgtcttt ctgagaaact gttca                                         25

<210> SEQ ID NO 25
<211> LENGTH: 25
<212> TYPE: DNA
<213> ORGANISM: Artificial Sequence
<220> FEATURE:
<223> OTHER INFORMATION: Antisense oligomer

<400> SEQUENCE: 25
ctgacaacag tttgccgctg cccaa                                         25

<210> SEQ ID NO 26
<211> LENGTH: 26
<212> TYPE: DNA
<213> ORGANISM: Artificial Sequence
<220> FEATURE:
<223> OTHER INFORMATION: Antisense oligomer

<400> SEQUENCE: 26
ccaatgccat cctggagttc ctgtaa                                        26

<210> SEQ ID NO 27
<211> LENGTH: 30
<212> TYPE: DNA
<213> ORGANISM: Artificial Sequence
<220> FEATURE:
<223> OTHER INFORMATION: Antisense oligomer

<400> SEQUENCE: 27
cattcaatgt tctgacaaca gtttgccgct                                    30

<210> SEQ ID NO 28
<211> LENGTH: 25
<212> TYPE: DNA
<213> ORGANISM: Artificial Sequence
<220> FEATURE:
<223> OTHER INFORMATION: Antisense oligomer

<400> SEQUENCE: 28
cttacaggct ccaatagtgg tcagt                                         25

<210> SEQ ID NO 29
<211> LENGTH: 29
<212> TYPE: DNA
<213> ORGANISM: Artificial Sequence
<220> FEATURE:
<223> OTHER INFORMATION: Antisense oligomer
```

<400> SEQUENCE: 29
ccactcagag ctcagatctt ctaacttcc                                          29

<210> SEQ ID NO 30
<211> LENGTH: 25
<212> TYPE: DNA
<213> ORGANISM: Artificial Sequence
<220> FEATURE:
<223> OTHER INFORMATION: Antisense oligomer

<400> SEQUENCE: 30
gggatccagt atacttacag gctcc                                              25

<210> SEQ ID NO 31
<211> LENGTH: 30
<212> TYPE: DNA
<213> ORGANISM: Artificial Sequence
<220> FEATURE:
<223> OTHER INFORMATION: Antisense oligomer

<400> SEQUENCE: 31
acatcaagga agatggcatt tctagtttgg                                         30

<210> SEQ ID NO 32
<211> LENGTH: 30
<212> TYPE: DNA
<213> ORGANISM: Artificial Sequence
<220> FEATURE:
<223> OTHER INFORMATION: Antisense oligomer

<400> SEQUENCE: 32
ctccaacatc aaggaagatg gcatttctag                                         30

<210> SEQ ID NO 33
<211> LENGTH: 26
<212> TYPE: DNA
<213> ORGANISM: Artificial Sequence
<220> FEATURE:
<223> OTHER INFORMATION: Antisense oligomer

<400> SEQUENCE: 33
gagcaggtac ctccaacatc aaggaa                                             26

<210> SEQ ID NO 34
<211> LENGTH: 25
<212> TYPE: DNA
<213> ORGANISM: Artificial Sequence
<220> FEATURE:
<223> OTHER INFORMATION: Antisense oligomer

<400> SEQUENCE: 34
ctgaaggtgt tcttgtactt catcc                                              25

<210> SEQ ID NO 35
<211> LENGTH: 30
<212> TYPE: DNA
<213> ORGANISM: Artificial Sequence
<220> FEATURE:
<223> OTHER INFORMATION: Antisense oligomer

<400> SEQUENCE: 35
tgttcttgta cttcatccca ctgattctga                                         30

<210> SEQ ID NO 36
<211> LENGTH: 18
<212> TYPE: DNA
<213> ORGANISM: Artificial Sequence
<220> FEATURE:
<223> OTHER INFORMATION: Antisense oligomer

<400> SEQUENCE: 36
ctttcataat gctggcag                                                 18

<210> SEQ ID NO 37
<211> LENGTH: 14
<212> TYPE: DNA
<213> ORGANISM: Artificial Sequence
<220> FEATURE:
<223> OTHER INFORMATION: Antisense oligomer

<400> SEQUENCE: 37
cataatgctg gcag                                                     14

<210> SEQ ID NO 38
<211> LENGTH: 8
<212> TYPE: DNA
<213> ORGANISM: Artificial Sequence
<220> FEATURE:
<223> OTHER INFORMATION: Antisense oligomer

<400> SEQUENCE: 38 gctggcag                                                             8

<210> SEQ ID NO 39
<211> LENGTH: 9
<212> TYPE: DNA
<213> ORGANISM: Artificial Sequence
<220> FEATURE:
<223> OTHER INFORMATION: Antisense oligomer

<400> SEQUENCE: 39 cagcagcag                                                            9

<210> SEQ ID NO 40
<211> LENGTH: 12
<212> TYPE: DNA
<213> ORGANISM: Artificial Sequence
<220> FEATURE:
<223> OTHER INFORMATION: Antisense oligomer

<400> SEQUENCE: 40
cagcagcagc ag                                                       12

<210> SEQ ID NO 41
<211> LENGTH: 15
<212> TYPE: DNA
<213> ORGANISM: Artificial Sequence
<220> FEATURE:
<223> OTHER INFORMATION: Antisense oligomer

<400> SEQUENCE: 41
cagcagcagc agcag                                                    15

<210> SEQ ID NO 42
<211> LENGTH: 18
<212> TYPE: DNA
<213> ORGANISM: Artificial Sequence
<220> FEATURE:
<223> OTHER INFORMATION: Antisense oligomer

```
<400> SEQUENCE: 42
cagcagcagc agcagcag                                                18

<210> SEQ ID NO 43
<211> LENGTH: 9
<212> TYPE: DNA
<213> ORGANISM: Artificial Sequence
<220> FEATURE:
<223> OTHER INFORMATION: Antisense oligomer

<400> SEQUENCE: 43 agcagcagc                                                           9

<210> SEQ ID NO 44
<211> LENGTH: 12
<212> TYPE: DNA
<213> ORGANISM: Artificial Sequence
<220> FEATURE:
<223> OTHER INFORMATION: Antisense oligomer

<400> SEQUENCE: 44
agcagcagca gc                                                      12

<210> SEQ ID NO 45
<211> LENGTH: 15
<212> TYPE: DNA
<213> ORGANISM: Artificial Sequence
<220> FEATURE:
<223> OTHER INFORMATION: Antisense oligomer

<400> SEQUENCE: 45
agcagcagca gcagc                                                   15

<210> SEQ ID NO 46
<211> LENGTH: 18
<212> TYPE: DNA
<213> ORGANISM: Artificial Sequence
<220> FEATURE:
<223> OTHER INFORMATION: Antisense oligomer

<400> SEQUENCE: 46
agcagcagca gcagcagc                                                18

<210> SEQ ID NO 47
<211> LENGTH: 9
<212> TYPE: DNA
<213> ORGANISM: Artificial Sequence
<220> FEATURE:
<223> OTHER INFORMATION: Antisense oligomer

<400> SEQUENCE: 47 gcagcagca                                                           9

<210> SEQ ID NO 48
<211> LENGTH: 12
<212> TYPE: DNA
<213> ORGANISM: Artificial Sequence
<220> FEATURE:
<223> OTHER INFORMATION: Antisense oligomer

<400> SEQUENCE: 48
gcagcagcag ca                                                      12
```

```
<210> SEQ ID NO 49
<211> LENGTH: 15
<212> TYPE: DNA
<213> ORGANISM: Artificial Sequence
<220> FEATURE:
<223> OTHER INFORMATION: Antisense oligomer

<400> SEQUENCE: 49
gcagcagcag cagca                                                      15

<210> SEQ ID NO 50
<211> LENGTH: 18
<212> TYPE: DNA
<213> ORGANISM: Artificial Sequence
<220> FEATURE:
<223> OTHER INFORMATION: Antisense oligomer

<400> SEQUENCE: 50
gcagcagcag cagcagca                                                   18

<210> SEQ ID NO 51
<211> LENGTH: 25
<212> TYPE: DNA
<213> ORGANISM: Artificial Sequence
<220> FEATURE:
<223> OTHER INFORMATION: Antisense oligomer

<400> SEQUENCE: 51
agcagcagca gcagcagcag cagca                                           25

<210> SEQ ID NO 52
<211> LENGTH: 25
<212> TYPE: DNA
<213> ORGANISM: Artificial Sequence
<220> FEATURE:
<223> OTHER INFORMATION: Antisense oligomer

<400> SEQUENCE: 52
cagcagcagc agcagcagca gcagc                                           25

<210> SEQ ID NO 53
<211> LENGTH: 9
<212> TYPE: DNA
<213> ORGANISM: Artificial Sequence
<220> FEATURE:
<223> OTHER INFORMATION: Antisense oligomer

<400> SEQUENCE: 53 caggcaggc                                                              9

<210> SEQ ID NO 54
<211> LENGTH: 12
<212> TYPE: DNA
<213> ORGANISM: Artificial Sequence
<220> FEATURE:
<223> OTHER INFORMATION: Antisense oligomer

<400> SEQUENCE: 54
caggcaggca gg                                                         12

<210> SEQ ID NO 55
<211> LENGTH: 24
<212> TYPE: DNA
<213> ORGANISM: Artificial Sequence
<220> FEATURE:
<223> OTHER INFORMATION: Antisense oligomer
```

<400> SEQUENCE: 55
caggcaggca ggcaggcagg cagg                                                24

<210> SEQ ID NO 56
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 56

Arg Arg Arg Gln Arg Arg Lys Lys Arg
 1               5

<210> SEQ ID NO 57
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 57

Arg Lys Lys Arg Arg Gln Arg Arg Arg
 1               5

<210> SEQ ID NO 58
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 58

Arg Arg Arg Arg Arg Arg Arg Arg Arg Phe Phe
 1               5                   10

<210> SEQ ID NO 59
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 59

Arg Arg Arg Arg Arg Phe Phe Arg Arg Arg Arg
 1               5                   10

<210> SEQ ID NO 60
<211> LENGTH: 4
<212> TYPE: PRT
<213> ORGANISM: Artificial Sequence
<220> FEATURE:
<223> OTHER INFORMATION: Cell penetrating peptide

<400> SEQUENCE: 60

Arg Arg Arg Arg
 1

<210> SEQ ID NO 61
<211> LENGTH: 5
<212> TYPE: PRT
<213> ORGANISM: Artificial Sequence
<220> FEATURE:
<223> OTHER INFORMATION: Cell penetrating peptide

```
<400> SEQUENCE: 61

Arg Arg Arg Arg Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Cell penetrating peptide

<400> SEQUENCE: 62

Arg Arg Arg Arg Arg Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Cell penetrating peptide

<400> SEQUENCE: 63

Arg Arg Arg Arg Arg Arg Arg
1               5

<210> SEQ ID NO 64
<211> LENGTH: 8
<212> TYPE: PRT
<213> ORGANISM: Artificial Sequence
<220> FEATURE:
<223> OTHER INFORMATION: Cell penetrating peptide

<400> SEQUENCE: 64

Arg Arg Arg Arg Arg Arg Arg Arg
1               5

<210> SEQ ID NO 65
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 65

Arg Arg Arg Arg Arg Arg Arg Arg Arg
1               5

<210> SEQ ID NO 66
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11
<223> OTHER INFORMATION: Acp

<400> SEQUENCE: 66

Arg Xaa Arg Arg Xaa Arg Arg Xaa Arg Arg Xaa Arg
1               5                   10

<210> SEQ ID NO 67
<211> LENGTH: 15
<212> TYPE: PRT
<213> ORGANISM: Artificial Sequence
```

```
<220> FEATURE:
<223> OTHER INFORMATION: Cell penetrating peptide
<220> FEATURE:
<221> NAME/KEY: MOD_RES
<222> LOCATION: 2, 5, 8, 11, 14
<223> OTHER INFORMATION: Acp

<400> SEQUENCE: 67

Arg Xaa Arg Arg Xaa Arg Arg Xaa Arg Arg Xaa Arg Arg Xaa Arg
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 8
<223> OTHER INFORMATION: Acp
<220> FEATURE:
<221> NAME/KEY: MOD_RES
<222> LOCATION: 5, 11
<223> OTHER INFORMATION: bAla

<400> SEQUENCE: 68

Arg Xaa Arg Arg Xaa Arg Arg Xaa Arg Arg Xaa Arg
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Cell penetrating peptide

<400> SEQUENCE: 69

Arg Ala Arg Arg Ala Arg Arg Ala Arg Arg Ala Arg Phe Phe Cys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Cell penetrating peptide

<400> SEQUENCE: 70

Arg Gly Arg Arg Gly Arg Arg Gly Arg Arg Gly Arg Phe Phe Cys
1               5                   10                  15

<210> SEQ ID NO 71
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 71

Arg Arg Arg Gln Arg Arg Lys Lys Arg Cys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Cell penetrating peptide
```

```
<400> SEQUENCE: 72

Arg Arg Arg Arg Arg Arg Arg Arg Arg Phe Phe Cys
 1               5                   10

<210> SEQ ID NO 73
<211> LENGTH: 13
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 3, 6, 9, 12
<223> OTHER INFORMATION: Acp
<220> FEATURE:
<221> NAME/KEY: MOD_RES
<222> LOCATION: 13
<223> OTHER INFORMATION: bAla

<400> SEQUENCE: 73

Arg Arg Xaa Arg Arg Xaa Arg Arg Xaa Arg Arg Xaa Xaa
 1               5                   10

<210> SEQ ID NO 74
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11, 13
<223> OTHER INFORMATION: Acp
<220> FEATURE:
<221> NAME/KEY: MOD_RES
<222> LOCATION: 14
<223> OTHER INFORMATION: bAla

<400> SEQUENCE: 74

Arg Xaa Arg Arg Xaa Arg Arg Xaa Arg Arg Xaa Arg Xaa Xaa
 1               5                   10

<210> SEQ ID NO 75
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 1, 4, 7, 10, 13
<223> OTHER INFORMATION: Acp
<220> FEATURE:
<221> NAME/KEY: MOD_RES
<222> LOCATION: 14
<223> OTHER INFORMATION: bAla

<400> SEQUENCE: 75

Xaa Arg Arg Xaa Arg Arg Xaa Arg Arg Xaa Arg Arg Xaa Xaa
 1               5                   10

<210> SEQ ID NO 76
<211> LENGTH: 13
<212> TYPE: PRT
<213> ORGANISM: Artificial Sequence
<220> FEATURE:
<223> OTHER INFORMATION: Cell penetrating peptide
```

```
<220> FEATURE:
<221> NAME/KEY: MOD_RES
<222> LOCATION: 2, 4, 6, 8, 10, 12
<223> OTHER INFORMATION: Acp
<220> FEATURE:
<221> NAME/KEY: MOD_RES
<222> LOCATION: 13
<223> OTHER INFORMATION: bAla

<400> SEQUENCE: 76

Arg Xaa Arg Xaa Arg Xaa Arg Xaa Arg Xaa Arg Xaa Xaa
 1               5                  10

<210> SEQ ID NO 77
<211> LENGTH: 15
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 4, 6, 8, 10, 12, 14
<223> OTHER INFORMATION: Acp
<220> FEATURE:
<221> NAME/KEY: MOD_RES
<222> LOCATION: 15
<223> OTHER INFORMATION: bAla

<400> SEQUENCE: 77

Arg Xaa Arg Xaa Arg Xaa Arg Xaa Arg Xaa Arg Xaa Arg Xaa Xaa
 1               5                  10                  15

<210> SEQ ID NO 78
<211> LENGTH: 17
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11, 14, 16
<223> OTHER INFORMATION: Acp
<220> FEATURE:
<221> NAME/KEY: MOD_RES
<222> LOCATION: 17
<223> OTHER INFORMATION: bAla

<400> SEQUENCE: 78

Arg Xaa Arg Arg Xaa Arg Arg Xaa Arg Arg Xaa Arg Arg Xaa Arg
 1               5                  10                  15

Xaa

<210> SEQ ID NO 79
<211> LENGTH: 14
<212> TYPE: PRT
<213> ORGANISM: Artificial Sequence
<220> FEATURE:
<223> OTHER INFORMATION: Cell penetrating peptide
```

```
<220> FEATURE:
<221> NAME/KEY: MOD_RES
<222> LOCATION: 2, 8, 13
<223> OTHER INFORMATION: Acp
<220> FEATURE:
<221> NAME/KEY: MOD_RES
<222> LOCATION: 5, 11, 14
<223> OTHER INFORMATION: bAla

<400> SEQUENCE: 79

Arg Xaa Arg Arg Xaa Arg Arg Xaa Arg Xaa Arg Xaa Xaa
 1               5                  10

<210> SEQ ID NO 80
<211> LENGTH: 7
<212> TYPE: PRT
<213> ORGANISM: Artificial Sequence
<220> FEATURE:
<223> OTHER INFORMATION: Cell penetrating peptide

<400> SEQUENCE: 80

Arg Arg Arg Arg Arg Arg Gly
 1               5

<210> SEQ ID NO 81
<211> LENGTH: 8
<212> TYPE: PRT
<213> ORGANISM: Artificial Sequence
<220> FEATURE:
<223> OTHER INFORMATION: Cell penetrating peptide

<400> SEQUENCE: 81

Arg Arg Arg Arg Arg Arg Arg Gly
 1               5

<210> SEQ ID NO 82
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 82

Arg Arg Arg Arg Arg Arg Arg Arg Gly
 1               5

<210> SEQ ID NO 83
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 83

Arg Arg Arg Arg Arg Gly Arg Arg Arg Arg Gly
 1               5                  10

<210> SEQ ID NO 84
<211> LENGTH: 12
<212> TYPE: PRT
<213> ORGANISM: Artificial Sequence
<220> FEATURE:
<223> OTHER INFORMATION: Cell penetrating peptide
```

```
<400> SEQUENCE: 84

Arg Arg Arg Arg Arg Phe Phe Arg Arg Arg Gly
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 85

Arg Lys Lys Arg Arg Gln Arg Arg Arg Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 86

Arg Arg Arg Gln Arg Arg Lys Lys Arg Gly
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: VARIANT
<222> LOCATION: 2, 8
<223> OTHER INFORMATION: Xaa = Ala, beta-alanine, Val, Leu, Ile, Ser,
      Gly, Thr, Phe, Trp, and 6-aminohexanoic acid

<400> SEQUENCE: 87

Arg Xaa Arg Arg Gly Gly Arg Xaa Arg Arg Gly Gly
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Cell penetrating peptide
<220> FEATURE:
<221> NAME/KEY: VARIANT
<222> LOCATION: 2, 6, 8, 12
<223> OTHER INFORMATION: Xaa = Ala, beta-alanine, Val, Leu, Ile, Ser,
      Gly, Thr, Phe, Trp, and 6-aminohexanoic acid

<400> SEQUENCE: 88

Arg Xaa Arg Arg Arg Xaa Arg Xaa Arg Arg Arg Xaa Gly
1               5                   10
```